US006803379B2

(12) United States Patent
Fernandez-Pol et al.

(10) Patent No.: US 6,803,379 B2
(45) Date of Patent: Oct. 12, 2004

(54) PHARMACOLOGICAL AGENTS AND METHODS OF TREATMENT THAT INACTIVATE PATHOGENIC PROKARYOTIC AND EUKARYOTIC CELLS AND VIRUSES BY ATTACKING HIGHLY CONSERVED DOMAINS IN STRUCTURAL METALLOPROTEIN AND METALLOENZYME TARGETS

(76) Inventors: Jose A. Fernandez-Pol, 437 Hunters Hill Dr., Chesterfield, MO (US) 63017-3446; Sebastian Fernandez-Pol, 437 Hunters Hill Dr., Chesterfield, MO (US) 63017-3446

( * ) Notice: Subject to any disclaimer, the term of this patent is extended or adjusted under 35 U.S.C. 154(b) by 0 days.

(21) Appl. No.: 10/161,981

(22) Filed: Jun. 4, 2002

(65) Prior Publication Data

US 2003/0225155 A1 Dec. 4, 2003

(51) Int. Cl.[7] ........................ A61K 31/41; C07D 291/00
(52) U.S. Cl. ........................................ 514/360; 548/122
(58) Field of Search ............................ 548/122; 514/360

(56) References Cited

U.S. PATENT DOCUMENTS

| | | | |
|---|---|---|---|
| 4,006,174 A | | 2/1977 | Calderazzo et al. |
| 4,293,547 A | | 10/1981 | Lewis et al. |
| 4,780,238 A | | 10/1988 | Premuzic |
| 4,797,264 A | | 1/1989 | Inoue et al. |
| 5,281,597 A | * | 1/1994 | McCall et al. |
| 5,506,191 A | * | 4/1996 | Anderson et al. |
| 5,641,776 A | * | 6/1997 | Missbach |
| RE35,585 E | | 8/1997 | Fernandez-Pol |
| 5,668,016 A | | 9/1997 | Fernandez-Pol |
| 5,767,135 A | | 6/1998 | Fernandez-Pol |
| 5,854,215 A | | 12/1998 | Findeis et al. |
| 5,955,287 A | | 9/1999 | Fernandez-Pol |
| 5,994,323 A | | 11/1999 | Gerolymatos |
| 6,001,555 A | | 12/1999 | Henderson et al. |
| 6,001,852 A | | 12/1999 | Gerolymatos |
| 6,127,393 A | | 10/2000 | Fernandez-Pol |
| 6,140,466 A | | 10/2000 | Barbas, III et al. |
| 6,329,378 B1 | * | 12/2001 | Mei et al. |

OTHER PUBLICATIONS

Please see attached Exhibit "Other References", paper 1 to 8.
Fernandez–Pol, J. A., et. al., "Essential Viral and Cellulaar Zinc and Iron Containing Metalloproteins as Targets for Novel Antiviral and Anticancer Agents: Implications for Prevention and Therapy of Viral Disease and Cancer", Anticancer Research vol. 21:931–958, 2001.
Fernandez–Pol, J.A., "Regulation of Apoptosis by Viruses and Zinc Chelators Antiviral Agents: Implications for Prevention and Therapy of Viral Deseases and Cancer", Jouranl of AIDS, vol. May 26: 1999, Abs. 12.
Ganger, R.G., et. al., "Differential Expression of Metallopanstimulin/S27 Ribosomal Protein in Hepatic Regeneration and Neoplasia". Cancer Detection and Prevention, vol. 25:241–246, 2001.

Fernandez–Pol, J.A., et. al., "Antiviral, Cytotoxic and Apoptotic Activities of Picolinic Acid on Human Immunodeficiency Virus–1 and Human Herpes Simplex Virus–2 Infected Cells". Anticancer Research, vol. 22:1–4, 2002.
Fernandez–Pol J.A., "Oxidative DNA damage mediated by hormone and growth factor regulated iron finger proteins: implications for prevention of cancer and aging", Annals of Oncology, vol. 9: 33–34, 1998.
Fernandez–Pol, J. A., et. al., "Molecular Interactions of Cancer and Age", Hematology/Oncology Clinics of North America, vol.14: 25–44, 2000.
Fernandez–Pol, JA., "Modulation of EGF receptor protooncogene expression by growth factors and hormones in human breast carcinoma cells", CRC Critical Reviews in Oncogenesis, vol. 2:173–185, 1991.
Fernandez–Pol JA et. al., "Transcriptional regulation of proto–oncogene expression by epidermal growth factor, transforming growth factor beta–1, and triiodothyronine in MDA–468 cells", Journal of Biological Chemistry, 264:4151–4156, 1989.
Fernandez–Pol, JA et. al., "Modulation of Transforming Growth Factor Alpha–Dependent Expression of Epidermal Growth Factor Receptor Gene by Transforming Growth Factor Beta, Triiodothyronine, and Retinoic Acid", Journal of Cellular Biochemistry, 41:159–170, 1989.
Fernandez–Pol JA, et. al., "A Growth Factor–inducible gene encodes a novel nuclear protein with zinc–finger structure", Journal of Biological Chemistry, vol. 268:21198–21204, 1993.
Fernandez–Pol J.A., et. al., "Metallopanstimulin gene product produced in a Baculovirus expression system is a nuclear phosphoprotein that binds to DNA", Cell Growth & Differentiation, vol. 5:811–825, 1994.

(List continued on next page.)

Primary Examiner—Deborah C. Lambkin
(74) Attorney, Agent, or Firm—Henry W. Cummings

(57) ABSTRACT

The invention relates to the treatment of viral, bacterial, parasitic, proliferative diseases, neurodegenerative diseases, inflammatory diseases, immunological diseases, transplanted organ rejection, and diseases produced by intoxication with heavy metals. The invention relates to the use of specific metal chelating agents including, furoic acid, 2-thiophenecarboxylic acid and their derivatives, analogs and structurally related chemicals as pharmacological agents that can be used effectively to disrupt and inactivate specific transition metal ion containing zinc finger structural motifs in metalloproteins and specific transition metal ion containing catalytic sites in metalloproteinases, which in turn, inactivate the pathogenic virus, pathogenic prokaryotic or eukaryotic cells which produces disease conditions. The preparations can be administered topically or for systemic use. The preparations are novel wide-spectrum antibiotics which have antiviral, antiproliferative, antineoplastic, antiangiogenic, antibacterial, antiparasitic, antiinfective, and anti-inflammatory effects and can be used in the treatment and prevention of diseases such as AIDS, cancers, untoward angiogenesis, pulmonary anthrax, malaria, inflammatory responses, Alzheimer's disease and other diseases.

9 Claims, 17 Drawing Sheets

OTHER PUBLICATIONS

Xynos, F.P., et. al., "Expression of Metallopanstimulin in Condylomata Acuminata of the Female Anogenital Region Induced by Papilloma Virus", Anticancer Research, vol. 4:773–786, 1994.

Fernandez-Pol J.A., et. al., "Correlation Between the Loss of the Transformed Phenotype and an Increase in Superoxide Dismutase Activity in a Revertant Subclone of Sarcoma Virus–Infected Mammalian Cells", Cancer Research, vol. 42: 609–617, 1982.

Collins, J. J., et. al., "Transient growth inhibition of *Escherichia coli* K–12 by ion chelators: "In vivo" inhibition of ribonucleic acid synthesis", Journal of Bacteriology, vol. 138: 923–932, 1979.

Santa Cruz, D. J., et. al., "Differential expression of metallopanstimulin/S27 ribosomal protein in melanocytic lesions of the skin", Journal of Cutaneous Pathology, vol. 24:533–542, 1997.

Brugge, J., et. al. (Eds.), "Origins of Human Cancer: A Comprehensive Review", Cold Spring Harbor Laboratory Press, pp 1–883, 1991.

Watson, J. D. et. al., "Molecular Biology of Gene Regulation", 4th edition, The Benjamin Cummings Publishing Co., Menlo Park, pp 494–496, 1988.

Berg, J.M., "Zinc fingers and other metal–binding domains", Journal of Biological Chemistry, vol. 265:6513–6516, 1990.

Berg, J.M., "Zinc finger domains: hypothesis and current knowledge", Annual. Review of. Biophysics.and Chemistry, vol. 19: 405–421, 1990.

Johnson, P.F, and McKnight, S.L., "Eukaryotic transcriptional regulatory proteins", Annual Review of Biochemistry, vol. 58:799–839, 1989.

Chan, et. al., "Zinc finger–like motifs in rat ribosomal proteins S27 and S29", Nucleic Acids Researcg, .vol., 21:649–655, 1993.

Grant, G.A. (Ed.), "Synthetic Peptides", WH Freeman and Co., New York, pp. 1–366, 1992.

Majno, G. and Joris, I. "Apoptosis, oncosis, and necrosis. An overview of cell death", American Journal of Pathology, vol. 146: 3–15, 1995.

Varesio, L., et al., "Ribosomal RNA metabolism in macrophages", Current Topics in Micorbiology and Immunology, vol. 181: 209–235, 1992.

Bosco, M.C., et al., "The Tryptophan Catabolite Picolinic Acid Selectively Induces the Chemokines Macrophage Inflammatory Protein–1α and – 1β in Macrophages", Journal of Immunology, vol., 164:3283–3291, 2000.

Wool, I.G., "Extraribosomal Functions of Ribosomal Proteins", Trends in Biochemical Sciences, vol. 21:165–165, 1996.

Bukau, B. and Horwich, A.L., "The Hsp70 and Hsp60 Chaperone Machines", Cell, vol 92: 351–366, 1998.

Howley, P.M., "The role of papillomaviruses in human cancer", Important Advances in Oncology,: vol. 1:55–73, 1987.

Chinami, M. et. al., "Nucleic acid binding by zinc finger––like motif of human papillomavirus type 16 E7 oncoprotein", Journal of Virological Methods, vol. 59: 173–176, 1996.

Alani, R.M., and Munger, K., "Human Papillomaviruses", Science and Medicine, vol. 5:28–35, 1998.

Collier, L., et. al. (Eds), "Topley & Wilson: Microbiology and Microbial Infections", vol. 1, Virology: vol. 2, Systemic Bacteriology; vol. 3, Bacterial Infections; vol. 4, Medical Mycology; vol, 5 Parasitology; $9^{th}$ edition, Publisher: Arnold, London, 1998, pp. 1–1025.

Lammers, M. and Follmann, H., "The Ribonucleotide Reductases—a unique group of metalloenzymes essential for cell proliferation", Structure and Bonding, vol. 54: 27–91, 1983.

Lien, E. J., "Ribonucleotide reductase inhibitors as anticancer and antiviral agents", Progress in Drug Research, vol. 31: 101–126, 1987.

Iordanov, M.S., etl al., "Ultraviolet radiation triggers the ribotoxic stress response in mammalian cells", Journal of Biological Chemistry, vol. 273: 15794–15803, 1998.

Mazurek, S., et. al., "The role of phosphometabolites in cell proliferation, energy metabolism, and tumor therapy", Journal of Bioenergetics and Biomemebranes, vol. 29: 315–330, 1997.

Saul, R. L., et. al., "Free Radicals, DNA Damage, and Aging", In: H. R. Warner, R. L., et. al., (Eds.), Modern Biological Theories of Aging, 1987; vol. 31, pp. 113–129. New York: Raven Press.

Nagase, H., and Woessner, J.F., "Matrix Metalloproteinases", Journal of Biological Chemistry, vol. 274;21491–21494, 1999.

Bauer, G., "Reactive. Oxygen and Nitrogen Species: Efficient, Selective, and Interactive Signals During Intracellular Induction of Apoptosis", Anticancer Research, vol. 20:4115–4140, 2000.

Arnold, R.S., et. al., "Hydrogen peroxide mediates the cell growth and transformation caused by the mitogenic oxidase Nox1", Proceeding of the National. Academy of Sciences, USA, vol. 98: 5550–5555, 2001.

Wang, X., "A chelate theory for the mechanism of action of aspirin–like drugs", Medical Hypothesis, vol. 50: 239–251, 1998.

Hendrickson, J.B., et. al., "Organic Chemistry", 3r Ed. McGraw–Hill Book Co. New York. Pp. 1–756, 1970.

Ege, N. S., "Organic Chemistry", $2^{nd}$ Ed., D.C. Heath and Co., Lexinton, pp1–450, 1989.

Knipe, D.M., et. al. (Eds), "Fields Virology", $4^{th}$, vol. 1 & 2, Lippincott Williams & Wilkins, Philadelphia, pp 1–850, 2001.

Avalos, J. and Maibach H.I., "Dermatological Botany", CRC Press, Boca Raton, pp 1–610, 2000.

Muro, O. et al., "Phytogrowth–inhibitory activities of 2–thiophenecarboxylic acid and its related compounds", Biological and Pharmaceutical Bulletin, vol. 17:160–162, 1994.

Louie, A.Y., and Meade, T.J., "Metal Complexes as enzyme inhibitors", Chemistry Review, vol. 99:2711–2734, 1999.

NCI, Federal Register, Antiviral Agents Bulletin: "HIV zinc finger therapeutics Screening and Development Opportunity", Aug. 10, 1995.

Koff, R.S., "Hepatitis C", Science & Medicine, vol. Jul./Aug.:16–25, 1998.

Lewis, L.D., et al., "Future options for the management of Hepatitis C", Seminars in Liver Disease. vol. 19 (Suppl. 1):103–112, 1999.

Lehman, I.R., and Boehmer, G., "Replication of Herpex Simplex Virus DNA", The Journal of Biological Chemistry, vol. 274:28059–28062, 1999.

Jeang, K–T, et. al., "Multifaceted activities of the HIV–1 transactivator of transcription, Tat", The Journal of Biological Chemistry, vol. 274: 28837–28840, 1999.

Lovejoy, D. et. al., "Structure activity relationship of novel chelators with anti–cancer activity: the "NT" series", In: Metal ions in Biology and Medicine, vol. 6. Eds. J.A. Centeno et al., John Libbey Eurotext, Paris, pp. 224–226, 2000.

Iordanov, S.M., et al., "Ultraviolet radiation triggers the ribotoxic stress response in mammalian cells", The Journal of Biological Chemistry, vol. 273:15794–15803, 1998.

Conte, D., et al., "In vivo and In vitro iron–replace zinc finger generates free radicals and causes DNA damage", The Journal of Biological Chemistry, vol. 271:5125–5130, 1996.

Thanh, X.D. et al., "Stability, toxicity and cytotoxicity of a cupric complex towards cultured Ca Co–2 cells", Anticancer Research, vol. 20:4639–4642, 2000.

Sakagami, E., et al., "Effect of cobalt ion on radical intensity and cytotoxic activity of antioxidants", Anticancer Research, vol. 20:3143–3150, 2000.

Feger, F., et. al., "Role of iron in tumor cell protection from the pro–apoptotic effect of nitric oxide", Cancer Reseach, vol. 61: 5289–5294, 2001.

Fan, L., et. al., "Inhibition of N–myc expression and induction of apoptosis by iron chelation in human neuroblastoma cells", vol. 61: 1073–1079, 2001.

Burns, E.A., and Leventhal, E.A., "Aging, immunity and cancer", Cancer Control, vol. 77:513–521, 2000.

Hall, I.H., et al., "Antitumor activity of mono– and dimetallic transition metal carborane complexex of Ta, Fe, Co, Mo, or W", Anticancer Research, vol. 20:2345–54, 2000.

D'Amore, P.A., et. al., "Angiogenesis", Science & Medicine, vol., May/Jun.: 44–53, 1999.

Carter, S.K., "Clinical Strategy for the Development of Angiogenesis Inhibitors", The Oncologist, vol. 5: 51–54, 2000.

Rosen, L., "Antiangiogenic Strategies and Agents in Clinical Trials", The Oncologist, vol. 5: 20–27, 2000.

Lush, R.M. et. al., "Review of Three New Agents that target Angiogenesis, Matrix Metalloproteinases, and Cyclin–Dependent Kinases", Cancer Control, vol. 6:459–465, 1999.

Brem, S., "Angiogenesis and Cancer Control: From Concept to Therapeutic Trial", Cancer Control, vol. 6: 436–458, 1999.

Jain, R.K., and Carmeliet, P.F., "Vessels of death or life", Scientific American, vol. Dec.: 40–45, 2001.

Bradley, K.A., et. al., "Identification of the cellular receptor for anthrax toxin", Nature, vol. 414: Nov. 8, 2001.

Pannifer, A.D. et al, "Crystal structure of anthrax lethal factor", Nature, vol. 414: Nov. 8, 2001.

Kochi, S.K., et. al., "Zinc content of the Bacillus anthracis lethal factor", FEMS Microbiology Letters, vol. 124:343–8, 1994.

Klimpel, K.R., et al., "Anthrax toxin lethal factor contains a zinc metalloprotease consensus sequence which is required for lethal toxin activity", Molecular Microbiology, vol. 13:1093–100, 1994.

Ronald, W. (Ed.), "Amyloid, prions and other protein aggreagates", Methods in Enzymology, vol. 309: 1–746, 1999.

Bush, A.I., et. al., "Rapid induction of Alzheimer Abeta amyloid formation by zinc", Science, vol. 265:1464–1467, 1994.

Breitner, A.I., et. al., "Inverse association of anti–inflammatory treatments and Alzheimer's disease: Initial results of co–twin control study", Neurology, vol. 44: 227–232, 1994.

McGeer, E.G. and McGeer, P.L., "The importance of Inflammatory mechanisms in Alzheimer Disease", Experimental Gerontology, vol. 33:371–378, 1998.

Blasko, I., et al., "Ibuprofen decreases cytokine–induced amyloid beta production in neuronal cells", Neurobiologic Diseases, vol. 6:1094–1101, 2001.

Kaytor, M.D., and Warren, S.T., "Aberrant protein deposition and neurological disease", The Journal of Biological Chemistry, vol. 274:37507–37510, 1999.

Bruce, A. J., et al., "Amyloid beta–Peptide alters the profile of antioxidant enzymes in hippocampal cultures in a manner similar to that observed in Alzheimer's disease", Pathogenesis, vol. 1:15–30, 1997.

Berg, D., et al., "Brain iron pathways and their relevance to Parkinson's disease", Journal of Neurochemistry, vol. 79:225–36, 2001.

Glass, J.D., and Wesselingh, S.L., "Microglia in HIV–associated neurological diseases", Microscopic Res. Tech., vol. 54:95–105, 2001.

Maeda, S.K., et. al., "Inhibition of hereditary hepatitis and liver tumor development in Long–Evans cinnamon rats by the copper–chelating agent trientine dihydrochloride", Hepatology, vol. 23:764–70, 1996.

Fujita, M., et. al., "Metal–chelating inhibitors of a zinc finger protein HIV–EPI: Remarkable potentiation of inhibitory activity by introduction of SH groups", Journal of Medicinal Chemsitry, vol. 39:503–7, 1996.

Scholz, M, et. al., "Immunomodulation and anticytomegalovirus activity of antioxidant metal chelators", Transplantation Proceedings, vol. 29:1272–3, 1997.

Mattsson, J.G., and Soldati, D., "MPS–1: A small, evolutionary conserved zinc finger protein from the protozoan Toxoplasma gondii", FEMS Microbiology Letters, vol. 180:235–239, 1999.

Choi, W.D., and Koh, J.Y., "Zinc and brain injury", Annual Review of Neuroscience, vol. 21:347–75, 1998.

Mueller, M.J., et. al., "Leukotriene $A_4$ hydrolase: Mapping of a henicosapeptide involved in mechanism–based inactivation", Proceeding of the National Academy of Sciences, USA, vol. 92:8383–8387, 1995.

Mueller, M.J., et al., "Analysis of the molecular mechanism of substrate–mediated inactivation of leukotriene $A_4$ hydrolase", The Journal of Biological Chemistry, vol. 273:11570–11575, 1998.

Nagase H, and Woessner J.F., "Matrix Metalloproteinases", Journal of Biological Chemistry vol. 274:21491–21494, 1999.

Nakada, M., et. al., "Suppression of membrane–type 1 matrix metalloproteinase (MMP)–mediated MMP activation and tumor invasion by Testican 3 and its splicing variant gene product, N–Tes", Cancer Research, vol. 61:8896–8902, 2001.

Bello, L., et al., "Simulataneous inhibition of glioma angiogenesis, cell proliferation, and invasion by a naturally occuring fragment of human metalloproteinase–2", Cancer Research, vol. 61:8730–8736, 2001.

Naglich, J.G., et al., "Inhibition of angiogenesis and metastasis in two murine models by the matrix metalloproteinase inhibitor, BMS–275291", Cancer Research, vol. 61: 8480–8485, 2001.

Miller, A.C., et al., "Potential health effects of the heavy metals, depleted uranium and tungsten, used in armor–piercing munitions: Comparison of neoplastic transformationm, mutagenicity, genomic instability, and oncogenesis", In Metal Ions in Biology and Medicine, vol. 6, Eds. Centeno, J. A., et al., John Libbey Eurotext, Paris, 2000, pp. 209–211.

Paulnock, D.M., "Macrophages, a practical approach", Oxford University Press, 2000, pp. 1–201.

Varesio, L., et al., "Ribosomal RNA metabolism macrophages", Current topics in Microbiology and Immunology, vol., 181:209–237, 1992.

Bosco, M.C., et al., "The tryptophan catabolite picolinic acid selectively induces the chemokines macrophage inflammatory protein–lalpha and –1beta in macrophages", The Journal of Immunology, vol. 164:3283–3291, 2000.

Hawk, E.T., et al., "Development of cyclooxygenase inhibitos as cancer chemopreventives", The American Society of Clinical Oncology, Perry, M.C., (Ed.), 2001, pp. 28–32.

Dannenberg, A.J., et al., Selective Inhibitors of COX–2: New applications in oncology, The American Society of Clinical Oncology, Perry, M.C, (Ed.), 2001, pp. 21–27.

DuBois, R.N., "Nonsteroidal anti–inflammatory drugs and colorectal cancer", The American Society of Clinical Oncology, Perry, M.C, (Ed.), 2001, pp. 16–22.

Rodrigues, R.R., et al., "Chelating agent inhibition of Trypanosoma cruzi epimastigotes in vitro", Journal of Inorganic Biochemistry, vol. 60:277–88, 1995.

Golenser, J., et. al., "The treatment of animal models of malaria with iron chelators by use of novel polymeric device for slow drug release", Journal of Pharmacology and Experimental Therapeutics, vol. 281:1127–35, 1997.

Bukau, B., and Horwich, A., "The Hsp70 and Hsp60 chaperone machines", Cell, vol. 92:351–366, 1998.

Snow, E. T., "Metal carcinogenesis: Mechanistic implications", Pharmaceutical Therapy, vol. 53:31–65, 1992.

* cited by examiner

2-TH acid

2-TH hydrazine 3,4,5-trichloro-2-TH acid hydrazone 4-butyl-3-chloro-2-TH acid thiosemicarbazone 2THA, 48 hours HY, 72 hours 3TTA, 72 hours Control, 72 hours BINDING OF 4-PENTYL-2-THIOPHENE CARBOXYLIC
ACID THIOSEMICARBAZONE
TO THE ZINC ATOM OF LTA$_4$ HYDROLASE

PHARMACOLOGICAL AGENTS AND METHODS OF TREATMENT THAT INACTIVATE PATHOGENIC PROKARYOTIC AND EUKARYOTIC CELLS AND VIRUSES BY ATTACKING HIGHLY CONSERVED DOMAINS IN STRUCTURAL METALLOPROTEIN AND METALLOENZYME TARGETS

CROSS-REFERENCE TO RELATED APPLICATIONS

STATEMENT REGARDING FEDERALLY SPONSORED RESEARCH OR DEVELOPMENT

None

BACKGROUND OF THE INVENTION

The invention relates to the treatment of viral, bacterial, parasitic, benign and malignant proliferative diseases, neurodegenerative diseases, inflammatory diseases, immunological diseases, transplanted organ rejection diseases, and diseases produced by intoxication with heavy metals. The invention relates to the use of specific metal chelating agents including, furoic acid, thiophenecarboxylic acid and their derivatives, analogs and structurally related chemicals as pharmacological agents that can be use effectively to disrupt and inactivate specific transition metal ion containing zinc finger structural motifs in metalloproteins and enzymatically active transition metal ion containing sites in metalloproteinases, and other metal containing motifs structural or functional, which in turn, inactivate the pathogenic virus, pathogenic prokaryotic or eukaryotic cells which produces disease conditions. The invention also includes the inactivation of any newly created biological pathogens and their metalloprotein products heretofore not recognized, such as those use in bioterrorism Since radioactive and non-radioactive materials can intoxicate metalloenzyme systems involved in normal physiological functions, the agents of this invention are also intended to be used for decontamination of animals and patients exposed to heavy metals spontaneously or by the use in bioterrorism.

It will be appreciated that hereinafter the use of the following terms: 1) "metalloprotein disrupting agent" encompasses all of the intended functions of the invention and method including antiviral, antiinfective, antiinflammatory, anticancer, and so on; 2) the broad term "antiinfective" is intended to include antiviral, antibacterial, antifungal, antiparasitic activities, as well as actions against any other infective agent or organism whether natural or synthetic; 3) the term "antiinflammatory" is intended to include any inflammatory response; and 4) the term "decontamination of heavy metals" is intended to include any use of these agents in the treatment of stable or radioactive heavy metal poisoning in man or animals. The term "biological response modifier" is intended to encompass any change in the response of a prokaryotic or eukaryotic cell to a second agent after initial treatment with any of the agents of this invention. It will also be appreciated that the term "anti-inflammatory" is intended to include all inflammatory responses of a metazoan organism such as production of stress heat shock proteins, white blood cell infiltrates, swelling, pain, fever and so on. The term "analgesic" refers to a pain reliever agent that functions in inflammatory conditions.

The role of metal ion containing proteins in physiological actions and pathological responses including cancer, inflammation, proliferative diseases and infectious diseases have been intensively study by many researchers. The inventors have studied the important functions of proteins having amino acid sequences which specifically bind transition metal ions. For example, the inventors have determined the role of zinc finger proteins in cancer, proliferative diseases and viral diseases. Moreover, the inventors have determined the role of numerous metalloproteins, such as the role of iron-finger hormone receptor proteins and zinc finger ribosomal proteins in carcinogenesis and aging.

A review of the literature reveals the critical role of metal containing proteins in physiological actions and pathological responses including cancer, inflammation, proliferative, infectious diseases and heavy metal poisoning (Fernandez-Pol, J A, 2001). The inventors have studied the important function of proteins having amino acid sequences which bind metals, particularly transition metal ions. The inventors have determined the important role metalloproteins in proliferative, inflammatory and infectious diseases. In additions, the inventors have determined the role of other metal ion containing protein complexes, such as the role of iron finger proteins in aging and carcinogenesis.

From the evidence reviewed, one can infer that development of a variety of drugs that control or neutralize metalloproteins may lead to a new therapeutic approach directed at controlling and preventing a wide spectrum of viral diseases, bacterial diseases, fungal diseases, cancer and other diseases involving abnormal expression of metalloproteins. Furthermore, the results suggest that these agents may be useful to prevent transmission of viral diseases and prevent the progression of other diseases. This review of the literature not only points out the limits of our understanding of this system, but also indicates the need for the development of new agents to control metalloproteins.

The specific features, objectives, and advantages of the instant invention and its preferred embodiments will become apparent after review and comparison with the prior art as follows. Remarkably, the instant invention provides agents heretofore not recognized, that interact with high specificity with structural metalloproteins and metalloenzymes essential for viral and cellular functions. However, none of these chelators are specific for zinc, in fact, some of them are more specific for iron, and they may have chelated a variety of transition metals (29). Nevertheless, these studies indicate that zinc plays a complex role in a dose and time-dependent manner in apoptosis.

The recent targeting of individuals and groups with the anthrax bacterium (*Bacillus anthracis*) spores is of great concern, particularly because the pulmonary form of this disease is most often fatal. This indicates the need to develop new antibiotics that will rapidly and effectively destroy the *B. anthracis* which proliferates inside lung and lymph node macrophages. This invention contributes new wide-spectrum antibiotics suitable for the destruction of *B. anthracis* inside macrophages which cannot perform their bactericidal functions in the presence of such bacterium.

Although only a limited number of viruses are currently thought to be adequate for biowarfare, such as smallpox or Marburg virus, there is a large number of viruses that can be made suitable and highly dangerous through genetic engineering manipulation or other selection process. There are thousands of animal and human viruses that have the potential to serve that purpose. Those viral agents that have not been recognized previous as credible biowarfare agents pose a present and clear danger, because there is no protection in the form of vaccines for prevention, no credible therapies, and no detection. The potential for destructive pandemic consequences would be far greater than those of the anthrax bacterium and may be similar to that of ancient smallpox pandemics. An opportunity exist to urgently correct and counteract this situation by developing new effective, low toxicity wide-spectrum antiviral agents. This invention contributes new wide-spectrum anti-viral agents suitable for these purposes.

The next sections discuss the background of this invention with special reference to applications to abnormal physiology, infectious diseases, heavy metal toxicity, special applications to enzymes, and metal complexes (Table 1).

ESSENTIAL VIRAL AND CELLULAR ZINC AND IRON CONTAINING METALLOPROTEINS AS TARGETS FOR NOVEL ANTIVIRAL AND ANTICANCER AGENTS

In this section the inventors summarize the experimental data on the role of a selected group of metalloproteins, particularly viral (v) and cellular (c) zinc finger proteins (ZFP) and iron containing proteins which are involved in cell proliferation, neovascularization, apoptosis, and viral infection. Furthermore, this review summarizes the data embracing the hypothesis that disruption of certain metalloproteins by novel pharmacological agents is a key factor in controlling viral and proliferative diseases. The primary goal of this review is to show the potential therapeutic applications of ZFP disrupting agents, zinc chelators and iron chelators in the control of viral diseases and cancer.

It is known that zinc or iron deficiency, resulting from exposure of culture cells to membrane-permeable $Zn^{2+}$ or $Fe^{2+}$-chelators, can induced apoptosis in virally transformed cells while normal cells remain unaffected under these conditions. Apoptosis is possibly due to simultaneous inactivation of vZFP, cZFP, and/or iron containing proteins, which are essential for maintenance of cellular and viral structure and which are activated in virally transformed cells. New insights concerning apoptosis, viral metalloproteins, and novel antiviral agents will also be reviewed.

From the evidence reviewed, one can infer that development of a variety of drugs that control or neutralize vZFP may lead to a new therapeutic approach directed at controlling and preventing a wide spectrum of viral diseases and cancer. Furthermore, the results suggest that these agents may be useful to prevent transmission of viral diseases. Finally, these data not only points out the limits of our understanding of these systems, but also directed the inventors to the creation of the novel agents of the instant invention.

Due to the central importance and essential functions of viral and cellular zinc-finger proteins, the literature on these topics is now rapidly expanding. Different aspects of ZFP functions, for example, in apoptosis induced by viruses, been reviewed in recent years. In this article we will concentrate on the available information about various zinc finger proteins of viruses, the drugs that inhibit their function, and cellular zinc finger proteins induced by virus infection in an attempt to critically evaluate some basic biological consequences of manipulating zinc finger proteins.

The background of the invention is presented as a brief summary of information with some initial hypothesis supported by experimental evidence at the molecular and clinical level. The inventors evaluate the role of a selected group of zinc finger proteins of cells and viruses involved in apoptosis and viral infection. Because of the importance of ribosomal proteins having zinc finger structures in viral replication and cancer, those functions also are reviewed. Moreover, the authors briefly address the role of heat shock zinc finger proteins. Finally, the inventors summarize the data that leads to the known information embracing the hypothesis that disruption of zinc finger proteins by novel antiviral and anticancer agents is a key factor in controlling viral diseases and cancer.

Apoptosis

Apoptosis, or single-cell death, is programmed cell death that occurs during normal homeostasis. Apoptosis is further defined by morphological and biochemical characteristics which are regulated by evolutionary conserved genetic pathways common to metazoan organisms. Apoptosis serves a complementary but opposite role to mitosis in normal homeostasis.

Apoptosis involves a complex network of pathways that interact with each other to be either pro-apoptotic or anti-apoptotic. Developmental or environmental stimuli activate or inactivate specific genes resulting in a series of biochemical degrading reactions that result in orderly cell disintegration. Apoptosis is induced by a variety of events such as viral infection, anticancer agents, radiation, growth factor deprivation, cytokines and hormones. Mutations of genes in this pathway eliminate the apoptotic response and have proven oncogenic. For example, over expressing the gene Bcl-2 or eliminating the gene p53 alters the susceptibility to apoptosis and allows the proliferation of damaged cells which frequently results in cancer.

Zinc Chelating Agents and Apoptosis

A recent review summarizes the evidence that apoptosis is modulated by intracellular excess or deficiency of $Zn^{2+}$ and presents some mechanism by which $Zn^{2+}$ may control apoptosis (Fernandez-Pol, et al, 2001). The major conclusions are: 1) zinc deficiency, resulting from dietary deprivation or exposure of cultured cells to membrane-permeable $Zn^{2+}$ chelators induces apoptosis; 2) zinc supplementation with $Zn^{2+}$ to the media of cell cultures, can prevent apoptosis; and 3) an intracellular pool of chelatable $Zn^{+}$ plays a critical role in apoptosis, possibly by modulating the activity of endonucleases.

There is evidence that apoptosis is modulated by intracellular excess or deficiency of $Zn^{2+}$. Fragmentation of DNA and cytolysis are inhibited in certain systems when Zn2+ (0.8 mM) is added to the culture medium, It is interesting to note that Ca2+/Mg2+-dependent endonuclease activity in isolated nuclei was inhibited when Zn2+ was added to the medium. These studies are consistent with the hypothesis that Zn2+ prevents apoptosis by blocking the activation or inhibiting the activity of Ca2+/Mg2+-dependent endonuclease. Numerous reports have shown that depletion of intracellular Zn2+ by chelation can trigger apoptosis in virally transformed cells. For example, when leukemia cells were exposed to 1,10-phenanthroline, a Zn2+/Fe2+ chelator, DNA fragmentation and cell death occurred, unless the chelator was neutralized by a transition metal ion added to the medium Similarly, picolinic acid (PA) a Zn2+/Fe2+ chelator, induces apoptosis in many cells, including leukemia cells by chelating a pool of intracellular Zn2+/Fe2+, since influx of Zn2+/Fe2+ prevented apoptosis in the presence of PA, while chelation of Zn2+/Fe2+ induced apoptosis.

Because Zn2+ plays a role in many cellular functions, and because it is an structural component of zinc finger proteins which are essential in cell replication, there are many sites in the apoptotic pathway that can be potentially modulate by zinc and zinc chelators. A number of investigators have shown that apoptosis can be induced if the intracellular level of Zn2+ are reduced using chelators. For example, N,N,N', N'-tetrakis-2-pyridyl methyl-ethylene diamine (TPEN) added to cultured cells induces apoptosis. These experiments add additional support to the hypothesis that changes in intra- and extracellular zinc can modulate apoptosis. However, none of these chelators are specific for zinc, in fact, some of them are more specific for iron, and they may have chelated a variety of transition metals. Nevertheless, these studies indicate that zinc plays a complex role in a dose and time-dependent manner in apoptosis.

Viruses relevant to human disease such as Smallpox, Ebola virus, Marburg virus, Lassa virus, Papillomavirus, Herpesvirus, and Retroviruses, including the AIDS virus, are all capable of inducing apoptosis. Viruses encode genes that both stimulate and suppress apoptotic cell death. These viral proteins interact with cellular pro-apoptotic (death factors) and anti-apoptotic (survival factors). Viral (v) and cellular (c) Zinc finger proteins (ZFP) are involved in apoptotic cell death. A pool of chelatable intracellular $Zn^{2+}$ plays a critical role in viral and cellular apoptosis, possibly by modulating ZFP structure. In virally transformed cells apoptosis can be induced by intracellular deficiency of $Zn^{2+}$ while normal non-infected cells remain unaffected.

Since 1980, Fernandez-Pol et al are studying the modulation of both v-ZFP and c-ZFP by a class of novel $Zn^{2+}$/Fe2+ chelating, broad-spectrum antiviral agents which may form ternary complexes with the zinc atoms contained in ZFP (42–60). In numerous experiments, we found that these wide-spectrum antiviral agents block viral replication and induced apoptosis in virally transformed cells in culture. These agents also interfere with abnormally expressed c-ZFP produced by spontaneously or radiation transformed cells in culture. Thus, these studies provide evidence for a close correlation between interference with ZFP of both viral and cellular origins and apoptosis in transformed but not in normal cells.

Iron and Zinc Finger Proteins

Transition metal ions at physiological concentrations, such as chromium, zinc, iron, cobalt, and copper, are essential elements for biological functions; however in higher quantities they are toxic (Fernandez-Pol, et al, 2001). Evidence indicates that elevated levels of iron contribute to carcinogenesis. Two main factors are important in iron induced oncogenesis: 1) The capacity of iron to generate highly reactive free radicals which damage DNA; and 2) the increase iron requirement by rapidly proliferating transformed cells, which is required for DNA replication (ribonucleotide reductase) and energy production (within the mitochondrial in key enzymes of the redox systems of the respiratory chain). Studies with iron chelating agents such as picolinic acid and desferoxamine have contributed significantly to the understanding of differential mechanisms of growth regulation in normal and transformed cells (Fernandez-Pol et al, 2001). It is known that iron induces mutagenesis and/or carcinogenesis, but the detail mechanism of iron-induced oncogenesis is unknown.

Initial in vitro studies have demonstrated the ability of cobalt and cadmium to structurally reconstitute the zinc finger domains in an active form. In contrast, nickel and copper bind to zinc finger proteins, but are unable to restore the DNA binding capacity. These studies suggest that heavy metal incorporation into zinc finger may be important in metal-induced toxicity. Recently, it has been found that an iron-substituted zinc finger may generate free radicals which damage DNA and potentially induced carcinogenesis. The estrogen receptor (ER) is a ligand-activated transcription factor whose DNA-binding domain (ERDBD) is of the type Cys4-Cys4, which coordinate two zinc atoms, forming two zinc finger domains. The capability of iron to replace zinc in zinc finger, denoted the iron finger, was demonstrated in a series of experiments both in vivo and in vitro. Iron has the ability to substitute for zinc in the ERDBD as demonstrated by mobility shift and methylation interference assays of iron finger, which show specific recognition of the estrogen response element. The DNA binding constants for both in vivo and in vitro iron-replaced zinc fingers were similar to that of the native zinc-containing finger. Atomic absorption analysis showed a ratio of 2:1 iron atoms/mol of ERDBD protein. Remarkably, the iron finger in the presence of hydrogen peroxide and ascorbate generates highly reactive free radicals (hydroxyl), producing a reproducible cleavage pattern to the DNA of the estrogen response element. The close proximity of the zinc finger to DNA, as found in the computer modeled structure, suggests that the iron-substituted zinc finger may generate free radicals while bound to genetic regulatory response elements, leading to degradation of DNA and/or carcinogenesis.

Zinc Finger Ribosomal Proteins

Fernandez-Pol et al have shown that human metallopanstimulin (MPS-1)/S27 ribosomal protein is a ubiquitous 9.4-kDa multifunctional "zinc finger" protein which is expressed at high levels in a wide variety of cultured proliferating cells and tumor tissues. The human MPS-1 gene and its relationship to human cancer cell growth was discovered by Fernandez-Pol et al in 1989, using human MDA-MB-468 breast cancer cells stimulated with specific growth factors and serum. Since that time, research has consistently demonstrated that both MPS-1 mRNA and protein are involved in cancer cell growth as demonstrated by increased levels of MPS-1 mRNA and protein found in numerous pathological tissue specimens obtained from various types of human cancers, such as prostate, breast, lung, colon, endometrium, uterine cervix, vulva, and melanoma. These results indicate that the MPS-1 antigen is a ubiquitous tumor marker which may be useful in detection and prognosis of various types of malignant neoplastic conditions. The results of other experiments indicate that MPS-1 is involved in protein synthesis, repair of damaged DNA, digestion of mutated mRNA, anti-apoptosis and rapid cell proliferation. Thus, the information available indicate that MPS-1 is a multifunctional S27 ribosomal protein relevant to numerous oncogenic processes which can be used as a ubiquitous tumor marker in various clinical assays. More recently, MPS-1/S27 ribosomal protein has been shown to be increased in virus infected cells, in parasites such as Toxoplasmosis and Malaria, in yeast proliferative capacity, and in macrophage activation in human melanomas NCBI, National Cancer Institute Data Bank; Fernandez-Pol, 2001).

It is important to note at this point that there are many reports indicating a connection between overexpression of some genes encoding ribosomal proteins and cancer. There is evidence that a number of other ribosomal proteins have additional functions separated from both the ribosome and protein synthesis. Zinc finger motifs are characteristics of numerous ribosomal proteins, allowing them to bind to nucleic acids. This binding ability offers a potential mechanism for ribosomal proteins to interfere in both transcriptional and translational mechanisms. For example, the rat ribosomal protein S3a is identical to the product of the rat Fte-1 gene which encodes the v-fos transformation effector.

S3a is involved in the initiation of protein synthesis and is also related to proteins involved in the regulation of growth and the cell cycle. Rat ribosomal protein L10 is homologous to the Jun-binding protein and to a putative Wilm's tumor suppressor. Taken together, the findings of ribosomal proteins with oncogenic, tumor supressor, or cell cycle functions, indicates extraribosomal functions of certain ribosomal proteins related to oncogenesis.

Zinc Finger Heat Shock Proteins and Viral Activation

The involvement of zinc fingers in protein-protein interactions extends beyond the control of gene expression. In numerous proteins the zinc finger domains have been implicated in mediating homodimerization or heterodimerization (Fernandez-Pol et al, 2001). Prokaryotes and eukaryotes express numerous heat shock proteins (Hsps) in response to stress, including heat shock, exposure to heavy metals, hormones and viral infections.

The stress response which include numerous forms of physiological and pathological stress is involved in viral infection. A prominent feature of this response is the synthesis of a discrete set of zinc finger proteins, known as the heat shock proteins, which at present are denoted molecular chaperons. During infection by certain viruses, heat shock proteins act as intracellular detectors that recognize malfolded proteins. Researchers have found that certain DNA viruses are able to activate heat shock proteins. For example, the Hsp70 (DnaK) is induced by adenovirus, herpes virus, cytomegalovirus, and other viruses.

One of the most interesting proteins involved in the viral infection response is the DnaJ, a heat shock protein which functions in the control of protein folding within the cell. DnaJ proteins contain two CCCC zinc finger motifs, defined by the J domain, which is essential for stimulation of the Hsp70 ATPase activity. Thus, the results indicate that there is a relationship between the stress response and the cytopathic effects of certain viruses such as herpes viruses, poxviruses, and hepatitis C viruses.

The response of cells to stress, such as exposure to UV radiation, chemicals, bacteria, parasites, fungus or viruses is also associated with the induction of heat shock proteins. Hsp70 has a protective role in inflammation, infection, and regulatory roles in cytokine biosynthesis. Hsp70 exists in the cells in equilibrium between its free state, in the cytoplasm, and its bound state, protecting proteins in the nucleolus, interacting with ribosomal proteins to either refold some of the unfolded ribosomal proteins or by solubilizing the denatured ribosomal proteins to facilitate their use and increase the turnover rate. During release as a result of the heat shock, and as the nucleolus begins to recover its normal activities, a significant proportion of Hsp70 returns to the cytoplasm. This protein-protein interaction may have important implications for viral replication.

Thus, cellular inflammatory responses to viral infection are part of the organism defense against viruses. Zinc finger proteins, therefore, may be a key to the control of the cellular inflammatory response. Agents which can modify the zinc finger heat shock proteins may be useful in controlling the stress response.

Viral Zinc Finger Proteins are Highly Conserved Structures

All viruses depend on their ability to infect cells and induce them to make more virus particles. If the virus is successful the cells almost invariably die in the process, and that process have been shown to be apoptosis in numerous instances. Other viruses can integrate its DNA in the cellular DNA and remain inactive for long periods. The nucleic acid genome of viruses is always surrounded by a protein shell, denoted capsid, which is composed of nucleocapsid proteins, and some viruses also have a lipid bilayer membrane, termed an envelope, which enclose the nucleocapsid proteins.

Viral ZFPs have been identified in at least two thirds of all viruses studied (Fernandez-Pol et al, 2001). Examples of families of viruses using metalloproteins such as ZFP, zinc ring proteins or transition metal ion-dependent enzymes for replication, packaging and virulence are Arenaviridae, Reoviridae, Rotaviridae, Retroviridae, Papillomavirinae, Influenza, Adenoviridae, Flaviviridae (Hepatitis C), Herpesviridae, and Orthomyxoviridae (Influenza viruses). Viral ZFP are structural virion proteins essential for viral replication and packaging of the virus inside infected cells. Deletion of zinc finger domains in specific vZFP is lethal to the virus. Since the zinc finger domains of vZFP are essential for viral survival functions, they are conserved throughout evolution and there are no known mutants of the vZFP domain(s). Because the viral zinc finger domain(s) represent indispensable site (s) on the vZFP that can be attacked by one or multiple drugs, vZFP are ideal and primary drug targets for the next generation of antiviral agents (Femandez-Pol et al, 2001).

A computer search of all known viruses reveals highly conserved structures in their nucleocapsid (NC) proteins and other essential viral proteins. All viral NC proteins contain sequences of about 20 amino acids with 4 invariant residues, CCHC or other combinations, which chelate zinc through histidine imidazole and cysteinic thiolates with a Kd les than $10^{-13}$. These structures are denoted viral zinc fingers, and are highly conserved in numerous families of viruses. Examples of viruses which posses zinc finger NC proteins and other zinc binding proteins are show in Table I. These metal binding proteins are highly conserved in nature, and they perform essential functions in viral infectivity. It has been shown that mutations of the chelating residues in the zinc fingers produces a non-infectious virus. Furthermore, chelating agents have been shown to inactivate viruses. Thus, disruption of these proteins by specific agents results in viral inactivation. It has been suggested that the course of numerous viral diseases, such as genital warts, genital herpes, smallpox, chickenpox, influenza, viral hepatitis, etc, can be altered by inhibiting essential viral metalloproteins utilized during the viral infection cycle (Fernandez-Pol et al, 2001).

Papilloma virus infection results in a number of proliferative diseases in humans including warts induced by type 4 human papilloma virus (common warts). Moreover, papilloma virus can cause plantar ulcers as well as plantar warts. Human papilloma virus infection of the uterine cervix is the most common of all sexually transmitted diseases. Commonly know as genital warts, this wide spread virus infection is a serious disease that potentially can develop into cervical cancer. Since the virus is permanently present in cells, infection recurs in a significant percentage of patients.

Condylomata acuninata, also denoted genital warts, are benign epithelial growths that occur in the genital and perianal areas and caused by a number of human papilloma viruses (HPV) including types 6, 11 and 54. These are low risk viruses which rarely progress to malignancy. However, high risk viruses such as HPV-16 and HPV-18 are associated with cervical intraepithelial cancer.

The actions of HPV are mediated by specific viral-encoded proteins which interact and/or modulate cellular DNA and proteins to produce abnormal growth and differentiation of cells. Two proteins of the HPV viral genome, E6 and E7, are well conserved among anogenital HPV's and both contribute to the uncontrolled proliferation of basal cells characteristics of the lesions. The E7 oncoprotein is a multi-functional protein with transcriptional modulatory and cellular transforming properties. The E7 oncoprotein is a zinc finger protein.

A strong correlation between zinc binding and transactivation activity of E7 has been documented. The HPV-16 E6 protein is a zinc finger protein that binds DNA and has transcriptional activity which depends on the formation of the zinc fingers. E6 protein can complex with the cellular tumor suppressor protein p53 and it is necessary with E7 protein for the immortalization of primary human epithelial squamous cells. Only two proteins of HPV are consistently expressed and integrated in keratinocytes, the E6 and E7 zinc finger proteins. The E6 and E7 proteins are responsible for continuous cell proliferation. About twenty HPVs are associated with ano-genital lesions and all transformed keratinocytes of these lesions contain E6 and E7 zinc finger proteins. The E6 and E7 regulate growth and transformation by interfering with cellular p53 and pRb proteins, respectively. Thus, one should be able to control HPV by inactivating E6 and E7, the critical zinc finger proteins which are required for replication. When replication of the virus is halted, apoptosis of the virally-infected cells must occur. Thus, one can alter the epidemiology of, for example, carcinoma of the uterine cervix by interfering with the functions of zinc finger proteins.

Herpes viruses are highly disseminated in nature. Herpes viruses vary greatly in their biological properties and the clinical manifestations of diseases they cause. In humans eight herpes viruses have been isolated to date: 1) herpes simplex virus 1 (HSV-1), herpes simplex virus 2 (H1SV-2), cytomegalovirus (HCMV), varicella-zoster virus (VZV), Epstein-Barr virus (EBV), human herpesvirus 6 and 7 (HHSV6 and HHSV-7). More recently the existence of HHV8 as a causative agent of Kaposi sarcoma has been documented. The known herpesviruses share two significant biological properties relevant to this invention: 1) all herpesviruses specify a large array of enzymes involved in nucleic acid metabolism, including ribonucleotide reductase, an iron containing enzyme; and 2) they possess major zinc finger DNA-binding proteins required for DNA replication.

Retrovirus virions contain a diploid genome consisting of an RNA complex formed by the association of two identical unspliced viral RNA molecules. In mature virions, RNA molecules are tightly bound to viral zinc finger proteins, denoted nucleocapsid proteins (Ncps). Retroviral Ncp is produced after the gag gene product (Pr55gag), has been processed by the viral protease. The Ncps are highly conserved in all known retroviruses. Point mutation of the cysteine and histidine residues of the zinc finger domain of NCp7 results in a radical reduction of genomic RNA packaging, and this results in a drastic decrease in viral infectivity. Further studies indicate that NCp7 plays a key role in several other steps of the viral life cycle.

The human immunodeficiency virus (HIV) encodes several regulatory proteins that are not present in other retroviruses. The nucleocapsid p7 protein of HIV has been targeted by the inventors and other investigators for treatment of UW viral infections. The p7 protein is required for the correct assembly of viral RNA in newly formed virus particles. The p7 protein contains two zinc fingers that are critical for the recognition and packaging of the viral RNA. Thus, agents that effectively attack the two zinc finger domains of the HIV virus nucleocapsid p7 protein inside infected cells will decrease the overall number of viral infective particles.

The influenza virus is not integrated with DNA and thus may be vulnerable to attack by the specific antiviral agents of this invention. The influenza viruses are dependent upon viral $Zn^{2+}$ metalloproteases for specific viral functions. Processing of critical proteins of influenza virus is mediated by virus-encoded $Z^{2+}$ metalloproteases. It is of interest for this invention that the most abundant virion protein and a type specific antigen of influenza viruses, the M1 protein, is a zinc finger protein. Furthermore, this protein is involved in packaging of the influenza virus. Thus, inhibition of influenza virus $Zn^{2+}$ metalloproteinases and/or zinc finger protein M1 by the agents of this invention presents an opportunity for controlling the progression of influenza virus infection.

The poxviridae is a large family of complex DNA viruses that replicate in the cytoplasm of vertebrate and invertebrate cells. The most notorious virus of this family is the variola virus that causes smallpox. Infectious poxvirus particles contain a complex transcription system. A large number of virus-encoded enzymes and factors are packaged in the virus particle. For example, RNA polymerase, a zinc requiring enzyme, is involved in early transcription. Furthermore, both the small catalytic subunit and the large regulatory subunit of ribonucleotide reductase are virus-encoded proteins and closely resemble their eukaryotic counterparts both structurally (80% homology) and functionally. The synthesis of ribonucleotide reductase, is induced rapidly after vaccinia virus infection. Catalytic activity of the small subunit is inhibited by hydroxyurea. Furthermore, some of the early viral and cellular transcription factors utilized by the smallpox virus are zinc finger proteins.

Filoviruses, which cause deadly haemorragic fevers, are a large group of viruses that have non-segmented negative-strand (NNS) RNA as their genomes. The two main types are the Marburg and the Ebola virus. The nucleoproteins of these viruses interact with the linear RNA genome and also with cellular and ribosomal zinc finger proteins to perform specific viral functions. Thus, filoviruses are susceptible to inhibition by the agents of this invention.

There are numerous examples of families of viruses which utilize zinc finger proteins, zinc ring proteins and/or transition metal ion-dependent enzymes for specific viral functions. These viral proteins play an essential role in the structure, replication and/or virulence of viruses such as Reoviruses, Rotaviruses, Hepatitis C viruses as well as numerous other viruses.

ZINC FINGER PROTEINS: TARGETS FOR PHARMACOLOGICAL THERAPY

Background

The National Cancer Institute has identified ZFP as the next target for antiviral drugs (USA Federal Register, 60, No. 154, 1995). Several laboratories are evaluating new antiviral drugs targeted to modify ZFP. These products are targeted towards modification of the amino acid cysteine, which is the binding site for zinc in zinc finger proteins. This section focuses on developments in the antiviral field related to inhibititors of zinc finger proteins of HIV, HPV, and HSV.

It has been known for many years that the structural and biological properties of viruses can be altered by chelating agents. For example, treatment of rotaviruses with chelating agents such as EDTA (10 mM) results in a single-shelled, double-layered, non-infectious viral particles. Moreover, in vitro exposure of various retroviruses to the chelating agents such as EDTA or EGTA in millimolar concentrations results in partial disintegration of viral membranes. Thus, disintegration and degradation of retroviruses and rotaviruses can be accomplished by chelating agents.

There are several chelating agents that eject the coordinately bound zinc atom from HIV zinc finger proteins. For example, Otzuka et al reported that novel zinc chelators inhibit the DNA-binding activity of zinc finger proteins of HIV. In addition, The Tat trans-activator, is a small protein of 75–130 amino acids, which may form a zinc-finger domain. Since HIV-1 lacking Tat replicates poorly and does not cause cytopathic effects, approaches to interfere with Tat may be useful in treating AIDS. The cysteine-rich domain of Tat binds divalent cations, either two Cd2+ or two Zn2+ atoms. Whether the cysteine-rich residues form a Zn2+ finger or a lattice binding pockets for divalent cations is unknown The pol gene also has a zinc finger amino acid sequence suggesting that chelation chemotherapy may have a role in the treatment of AIDS.

At least three efficient approaches may be used to design novel classes of inhibitors of viral ZFP activity that directly attack vZFP: 1) disruption of the zinc finger domain by modification of the cysteine residues which are the binding sites for $Zn^{2+}$ in the vZFP, resulting in the ejection of zinc ion; 2) removal of the zinc from the zinc finger moiety by specific chelating agents, which results in inactivation of the vZFP; and 3) specific chelating agents that form a ternary complex at the site of zinc binding on vZFP, resulting in inhibition of the DNA or RNA binding activity of vZFP. Since these antiviral agents attack highly conserved structures in the virus they may circumvent the emergence of drug resistant mutants. Furthermore, the basic mechanisms of action of the novel antivirals (1 through 3, above) may be enhanced in viral disease if the antiviral agents which directly attack metalloproteins of the virus simultaneously attack cellular metalloproteins implicated in the pathogenesis of viral disease. Hence, the novel antivirals may also prove to be effective against cellular zinc finger-containing proteins such as ribosomal ZFP and heat shock proteins which are involved in viral infection. These cellular proteins are induced by the virus for specific viral functions such as replication, propagation, or as an inflammatory response of the cells to the virus.

The specificity of these agents may be due to cellular specificity, in which virally infected cells express cellular and viral ZFPs that are not expressed by normal uninfected cells in their basal or proliferative state. Another primary mode of action of these agents could be receptor specificity, in which vZFP act as receptors for specific zinc ejecting agents, or specific chelating agents which bind to vZFP and form an inactive ternary complex consisting of vZFP-Zn-chelating agent. Thus, vZFP may act as receptors for new agents that can form ternary complexes with vZFP.

Disruption of Viral Zinc Fingers of HIV by Chemical Agents

The HIV virus represents a daunting challenge for chemotherapy. A major problem with the treatment of HIV-1 infection is the emergence of drug resistance. HIV-1 nucleocapsid protein zinc fingers are targets of choice because they are mutationally intolerant and are required for both acute infection and virion assembly. After treatment with nontoxic disulfide-substituted benzamides which attack zinc fingers, the following has been observed with HIV virus: 1) inactivation of cell-free virions; 2) inhibition of acute and chronic viral infections; and 3) broad anti-retroviral activity. More important, resistant mutants have not been detected.

In all retroviruses, except spumaretroviruses, the nucleocapsid (NC) proteins contain one or two copies of a conserved zinc finger domain. This motif, represented as $C\text{-}X_2\text{-}C\text{-}X_4\text{-}H\text{-}X_4\text{-}C$ (C, cysteine; H, histidine; X, other amino acids), thereafter denoted a CCHC box or retroviral zinc finger, is different in different retroviruses, and coordinates a zinc ion in the virion. The histidine imidazole and cysteine thiolates chelate zinc ($Kd<10^{-13}$). The CCHC box is one of the most highly conserved motifs in retroviruses. All mutations in the zinc finger domain which have been described to date have been lethal for the virus. The HIV-1 NC protein contains two zinc fingers separated by just 7 amino acids. The zinc fingers of NC p7 protein are required for both early events in virus infection and for packaging genomic RNA.

Rice et al proposed that the HIV-1 NC protein is an ideal target for drug development because of the following reasons: 1) the two zinc fingers are indispensable sites on the same protein that can be attack by a single drug; 2) Simultaneous mutations in each zinc finger would be required for the development of drug resistance; and 3) the close proximity of the targets greatly reduces the probability of recombinatorial events.

Numerous compounds that fracture the CCHC zinc finger also inactivate the HIV-1 virus. These products have been suggested to be effective for a broad range of human and animal diseases, including drugs to treat cancer and viral infections. The zinc fingers of retroviral NC proteins are prime antiviral targets because of the conservation of the Cys and His chelating residues and the absolute requirement of these fingers in both early and late phases of retroviral replication. Thus, drugs that interact with the CCHC zinc finger structures of HIV-1 and other retroviral nucleocapsid proteins may be extremely useful to halt the propagation of the virus.

A core HIV viral protein, denoted p7 nucleocapsid (NC), has two zinc fingers. The zinc fingers are involved in binding and packaging viral RNA into new virions which bud off from the infected cells. Experiments have demonstrated that when the two zinc fingers are deleted, the new budding virions are unable to incorporate RNA, resulting in non-infectious viral particles. Furthermore, the p7 NC protein participate in the process of reverse transcription. The exact role of p7 in this process is not clear, but it is thought that the p7 NC protein binds to the RNA molecule while the reverse transcriptase enzyme generates DNA from the RNA template. More important, HIV p7 NP in which the zinc fingers have been deleted is unable to infect susceptible cells. The zinc fingers are therefore essential for both phases of the viral life cycle: packaging and transcription.

A number of drugs that interact with zinc fingers work by ejecting Zn from the zinc finger, resulting in an a functional protein. The same drugs were active against HIV in tissue culture. One of the drugs is disulfiram (Antabuse), a drug that is frequently used for the treatment of alcoholism. However, this drug was ineffective in monkeys carrying SIV. Rice et al reported that C-nitroso compounds inactivate HIV-1 and eject zinc from the virus. Retroviral zinc-fingers of the type CCHC bind zinc stoichiometrically and with high affinity (dissociation constant Kd, about $10^{-12}$ M). Under physiological conditions, a 10-fold excess of EDTA removes only 50% of the zinc from the N-terminal CCHC zinc finger domain of the HIV-1 nucleocapsid protein, indicating that the chelating agent EDTA is inefficient in removing Zn from ZFP. To determine whether 3-nitrosobenzamide (NOBA) is capable of efficiently ejecting Zn from retroviral-type zinc-fingers, Rice et al used NMR to study an 18-residue peptide with sequence corresponding to the N-terminal zinc-finger domain of the HIV-1 nucleocapsid protein, denoted Zn (HIV-1-F1). The $^{1}H$-NMR spectrum showed that addition of NOBA results in the loss of signals generated by the zinc-bound histidine, and the appearance of zinc-free histidine signals.

Rice et al have also proposed that disulfide benzamides possess a wide-spectrum antiretroviral activity in cell culture by "attacking" the two zinc fingers of the HIV-1 nucleocapsid protein (NCp7) and ejecting the zinc. Nucleocapsid is present in the core of all retroviruses. NCp7 binds to the dimeric viral RNA genome. Mutagenesis of any of the cysteines of histidines in the ZF of HIV-1 NCp7 generates virions with defective RNA encapsidation and noninfectious particles. These observations indicate that compounds which specifically destroy the coordination of the Zinc to the NCp7 will have an antiviral effect. Further experiments demonstrated that the antiretroviral activity of these compounds is due to inactivation of NCp7.

Finally, one of the great problems with antiretroviral agents currently in use is the ability of the virus to generate mutants which are resistant to the therapeutic agent and which are able to replicate with the same efficiency as the wild-type. This problem could be solved if the target protein has no alternative structures capable of replacing the original target protein. The properties of the zinc fingers in numerous viral proteins indicate the they are the proper targets to avoid mutation: The zinc finger is absolutely conserved in retroviruses (except spumaretroviruses), and all mutants in the zinc finger are defective with respect to infectivity. However, it is unclear whether mutants defective in zinc fingers may arise in certain circumstances.

Inhibition of Viral and Cellular Ribonucleotide Reductases (RR) by Iron Chelating Agents: Implications for Therapy of HSV and HIV Antivirals for the treatment of herpes infections such as acyclovir, ganciclovir and foscarnet have had a significant impact on the management of herpesvirus infections. However, the use of these agents has resulted in an increase emergence of drug-resistant virus strains. The need for new classes of anti-HSV compounds with novel mechanisms of viral inhibition is becoming increasingly apparent as mutants resistant to conventional antiviral agents emerge.

When a virus infects a cell, it could induce its host to make doxyribonucleotides for viral DNA replication by means of the cellular enzyme ribonucleotide reductase, or the virus, as in the case of HSV could carry its own specific RR genes which are expressed in the host cells and produce a new enzyme.

Iron chelators inactivate the RR of HSV. Since iron restores the activity of RR, the chelators inactivate the RR by directly removing its catalytically essential iron. Interestingly, there are certain chelators such as (348U87) 2Fe and (A1110U)2Fe that also inactivate the viral RR. It is conceivable that the antiviral-Fe-RR forms a ternary complex that prevents the catalytic function of the Fe2+, labilazing the enzyme-bound iron to dissociation.

Numerous herpes viruses, such as herpes simplex (HIV-1 and HIV-2), Epstein-Barr virus (EBV), varicella-zoster virus (VZV), pseudorabies virus (PRV), and equine herpesvirus type I (EHV-1), and numerous other herpes viruses encode cellular ribonucleotide reductase (RR) activities. RR, which is formed by the association of two nonidentical subunits (R1 and R2), catalyzes the reduction of ribonucleoside diphosphates to their 2'-deoxy derivatives which are key intermediates in DNA biosynthesis. There is increasing evidence supporting the essentiality of RR in viral replication. Numerous organisms, including herpes viruses, bacteria, and mammals, encode ribonucleotide reductases the share a number of common characteristics. Two important characteristics of RR are the presence of a stable tyrosyl free radical and the dependency of Fe (III) for catalytic activity. The smaller (R2) subunit contains the iron and tyrosyl radical and the larger (R1) contains thiols which are redox active and provide the hydrogen for nucleotide reduction. The association of R1 and R2 are required for catalytic activity. Thus, a potential approach for antiviral therapy would be the utilization of peptides that can inhibit enzymatic activity by preventing the association of R1 and R2 subunits. However, since iron is required for catalytic activity a potential, less specific, strategy for antiviral therapy are iron chelating agents, which would deplete iron from the cells, and may have a significant activity against herpes viruses. In 1998 picolinic acid was tested at 3 to 1.5 mM on cultured Human Foreskin (HF) cells infected with HSV-2-strain G and it was found to cause apoptosis of HF infected cells. The specificity of the iron chelators may be cellular specificity rather than viral specificity: infected cells enter apoptosis versus non-infected cells which remain unaffected.

It is relevant to mention that cellular RR is not only an important virulence factor for herpes viruses, but that cellular RR is also involved in the virulence of HIV. It has been suggested that the inhibition of RR with agents such as hydroxyurea could have a possible application in the treatment of AIDS. Giacca et al have found synergistic antiviral actions of ribonucleotide reductase inhibitors and 3'-azido-3'-deoxythymidine on HIV-1. RR inhibitors reduce the cellular supply of DNA precursors (dNTP) by interfering with their de novo synthesis. A secondary effect is the stimulation of the uptake an phosphorylation of extracellular deoxynucleosides, including their analogs such as 3'-azidothymidine (AZT). Both effects are important to HIV replication, which requires dNTP and is impaired by the triphosphate of AZT. A clear synergism between AZT and RR inhibitors was observed at nontoxic doses.

MOLECULAR BIOLOGY OF CARCINOGENESIS AND AGING

The cancer phenotype consists of several distinct characteristics such as indefinite proliferative life span, anchorage-independent growth, low growth factor requirements, neovascularization, invasion and metastasis. A common characteristic of tumor cells is the constant overexpression of glycolytic and glutaminolytic enzymes, which results in altered carbohydrate metabolism In addition, cancerous cells can synthesize their own growth factors, which leads to cell proliferation that is independent of the otherwise carefully regulated supply of growth factors and growth-related hormones. Moreover, growth factors are instrumental in the invasive characteristics of cancer cells. For example, Vascular Endothelial Growth Factor (VEGF) activates the proliferation of endothelial cells which results in the creation of new blood vessels. Most interesting, growth factors can also activate matrix metalloproteinases (is) which are able to degrade the extracellular matrix. Remarkably, one of the prominent features of MMPs is that many of these genes are inducible by growth factors, cytokines, carcinogenic agents (e.g. phorbol esters), chemotherapeutic agents (actin stress fiber-disrupting drugs), radiation, and oncogenic cellular transformation. MMPs gene expression may also be downregulated by transforming growth factors, retinoic acids and glucocorticoids. Thus, MMPs are fundamental enzymes in both the invasive process and metastatic disease and are susceptible to pharmacological control. The development of potent synthetic inhibitors of MMPs had led to clinical trials to treat patients with cancer.

There are growth factors and oncogenes produced by viruses which illustrate the complexity of the growth regulatory mechanism and the oncogenic process in vivo. For example, the complex smallpox virus which has recently acquire new notoriety due to its potential use in bioterrorism, contains a gene that encodes soluble EGF protein which promotes cell proliferation and is detected in all poxviruses genera. Furthermore, the family of poxviruses produce interleukin-1 beta receptor which blocks IL-1 beta cellular defense activity. Tumor Necrosis Factor (TNF) is also produced by poxviruses and contributes to virulence in the form of apoptosis. All these poxviruses virokines and viroreceptors gene products contribute to the pathogenesis in the form of production of granulomatous proliferative lesions, and benign tumors as in the case of myxomatosis of rabbits. It has also been reported that the tat protein of the human immunodeficiency virus (TV), a viral regulatory gene product, possesses growth stimulatory activity in certain cell types. Oncogenic proteins of human papilloma viruses such as the E6 and E7 zinc finger proteins are also able to immortalize normal cells in vivo and in vitro. These oncogenic proteins are involved in human cancers such as the carcinoma of the uterine cervix.

The life spans of animals are genetically controlled and new data exist to support common mechanisms to control the number of times a cell will divide before it can no longer divide (senesce). A fundamental characteristic of normal cells is their limited ability to proliferate in culture. Invariably, after an initial mitotic period in culture, normal cells from humans and most other species suffer a gradual decline in their ability to proliferate. Eventually, the decline becomes irreversible. This progression towards a lower activity state has been termed "cellular senescence". Cellular senescence has been studied most often in cultures of human fibroblasts (e.g. WI-38 cells). Numerous studies have indicated that cellular senescence in culture reflects aging in vivo. More recent studies have suggested that senescent fibroblasts are unable to proliferate, at least in part, because of selective repression of genes involved in transcriptional activity, such as a protooncogene designated as c-fos.

Cancer in humans and animals results from a multistep process which is described in experimental model systems as initiation, promotion, conversion, and progression. Each step in the process represents the selection of cells that have acquired the ability to surmount extra and intracellular growth regulatory signals. The cytogenetic evidence of multiple chromosome abnormalities in most tumor cells and the progressive aberrant chromosome structures that can be observed during tumor progression are also evidence for multistep process. Since the tumorigenic process is of rare occurrence, multiple levels of control must be operative to prevent the emergence of such cells in metazoan organisms.

The common cancers of the adult, including colon, lung, prostate and breast develop by stepwise accumulation of mutations affecting both oncogenes and tumor suppressor genes. These mutations accumulate gradually over time and extensive genetic changes are necessary to produce a highly malignant cell. For example, benign adenoma of the colon usually have a single gene change. As they progress toward malignancy they acquire 3 or 4 more gene alterations. These multiple changes may occur in a specific order. However, it is very likely that the number of changes rather than a precise sequence is important for cancer development. Thus, the non-specific cellular changes as the cell ages continue to contribute to shift the balance of control from tumor suppressor genes to oncogenes.

There are overlapping mechanisms that may be common to both cancer and aging. The loss of the efficient DNA repair-capacity is a major factor in both cancer progression and the aging process. One model for aging states that it is the result of accumulation of damage in the DNA genome with resulting loss of function of critical genes. It has been proposed that during the aging process, robust DNA repair events become less active or inefficient resulting in accumulation of damaged DNA, and eventually in death. One unifying concept simply states that failure to repair DNA damage in protooncogene or tumor suppressor genes causes loss of growth control and cancer. However if the accumulation of DNA damage does not involve these growth regulatory genes this simply leads to cell death or senescence.

METALLOPROTEINASES: TARGETS FOR PHARMACOLOGICAL THERAPY

The mechanisms by which numerous chelating agents work on specific metalloenzymes have been characterized. These mechanisms provide investigators with several metalloprotein targets. Specific drugs can be created that will inactivate the target metalloproteins. This patent application describes a group of novel chelating compounds that were designed for the specific control and inactivation of metalloproteinases.

Proteinases are enzymes whose function is the cleaving of protein chains at specific sites. They play a critical role in the physiology of viruses, prokaryotic and eukaryotic cells. Proteinases are essential for the processes of growth, would healing, tissue remodeling, immunological defense, digestion, apoptosis, and coagulation. Pathological activation or inactivation of these enzymes leads to numerous disorders that contribute to disease initiation and progression. These enzymes are targets for the development of proteinase inhibitors which result in numerous drugs for the treatment of diseases such as hypertension, coronary artery disease, asthma, inflammation, arthritis, cancer, metastasis, infectious diseases, cardiovascular, respiratory and neurodegenerative disorders.

Proteolytic enzymes are able to cleave peptide bonds and are characterized as hydrolases. Proteinases are further divided into four classes: serine proteases (I), cysteine proteases (II), aspartic proteases (II), and metalloproteinases (IV). The compounds of this invention refer exclusively to metalloproteinases and are proteinase inhibitors pharmacologically active at the metal ion containing active enzymatic site.

Modification of abnormal metalloproteinase activity represents an opportunity for controlling the initiation and progression of many diseases. The inventors and others have recognized that effective inhibitors of zinc containing metalloproteinases must have at least: 1) one functional group capable of binding to the catalytic zinc such as carboxylic acid, thiol, or hydroxamic acid; 2) have at least one functional group which can H-bond with the enzyme backbone; and 3) have one or more side chains capable of favorable London interactions with the enzyme active site. There are numerous examples of specific drugs that can be used to inhibit zinc metalloenzyme in accordance with the principles delineated above, for the purpose of controlling the initiation and progression of specific diseases. For example, a prime enzyme target in ocular hypertension is carbonic anhydrase (CA). CAs are metalloenzymes and many inhibitors of these enzymes are metal complexing anions that coordinate directly to zinc in the enzyme active site. Carbonic anhydrases are inhibited by sulfonamides that bind zinc and in the process substitute a catalytically important water molecule. Another example is the angiotensin-converting enzyme (ACE), a component of the renin-angiotensin system ACE is a zinc metalloenzyme that is inhibited by zinc chelators. For example, Captopril was designed to compete with angiotensin for the zinc ion in the enzyme and binds to zinc through a thiol group. Lisinopril, another ACE inhibitor binds to zinc through an amino carboxylate moiety. Based on these pharmacological concepts, the inventors present in this application examples of the successful or promising pharmaceutical applications of a novel type of metalloproteinase inhibitors.

METAL COMPLEXES OF CHELATING AGENTS AS ENZYME INHIBITORS

In recent years major advances in elucidating the interaction between metalloproteins and therapeutic agents have allowed exact predictions for the drug binding sites. The exact nature of this interaction is critical to control drug specificity which in turn leads to the reduction of unwanted side effects. Structural information can be used to design molecules that bind to specific targets. The substrate specificity of enzymes allows the design of drugs with a well-defined specificity. Metalloenzymes are targets for inorganic drugs since metals play a key structural and catalytic role for numerous enzymes such as the zinc metalloenzymes that are one of the topics of this patent application. Neutralizing a metal that is essential to enzymatic action by another catytically incompetent metal can result in an inactive enzyme. This pharmacological action can be obtained by the coordination of an exogenous toxic metal to a specific chelating agent which will result in the substitution of the metal, or removal of the metal from the enzyme active site. The platinum drugs are one example in which the therapeutic effect of the drug is due to platinum while the chelating agent ligand is merely a carrier. Metal complexes of carbothioamides and thiosemicarbazones have also been found to inhibit ribonucleotide reductase and possess anticancer activity. Copper complexes and copper complexes of antiinflammatory drugs have been shown to be effective as antiiflammatory agents. Furthermore, the matrix metalloproteinase matrilysin, a zinc enzyme, has been shown to be inactivated by cadmium, which forms an inactive Cd/Zn hybrid. It is evident from these works that complexes of metal ions can be very useful in many different disease conditions.

The coordination ability of metals allows the formation of strong attachments through covalent and ionic bonds. The term "metal complexes" is interpreted to include complexes, compounds or ions. This compounds exert their therapeutic effect by binding to a metal site in an enzyme active site. The formation of the metal complex is central to their inhibitory actions.

Viruses utilize a discrete set of unique enzymes to perform their life cycles. Thus, these enzymes provide targets for antiviral drugs. Thiosemicarbazones have been used as antiviral agents. Thiosemicarbazones are also known to inhibit ribonucleotide reductase, RNA-dependent DNA polymerase, and dihydrofolate reductase. HIV-1 protease is an aspartyl protease that generates mature proteins from the products of the gag and pol genes. Many metal ions have been found to be inhibitors of HIV-1 protease. These observations together with the novel compounds of this invention may lead to the design of potent inhibitors of HIV-1 proteases which contain metals that can bind to the enzyme through ionic or covalent interactions and thus can be stronger inhibitors than the currently available.

CONCLUSIONS AND FUTURE PROSPECTS FROM THE EVIDENCED REVIEWED IN THE BACKGROUND OF THE INVENTION

Form the foregoing it appears that it would be beneficial to have a product that can interfere with the structure or action of certain zinc finger proteins or zinc metalloproteinases to stop the progression of certain infectious diseases, proliferative diseases, neurodegenerative diseases, and other diseases that depend upon zinc finger proteins and/or zinc metalloproteinases for the generation of the disease state. Furthermore, it would be beneficial to provide a product that can control these diseases by chelating metal ions from zinc-dependent, iron-dependent or copper-dependent proteins, enzymes, and/or hormone receptors necessary for the initiation, progression and maintenance of replication of cancer cells and other proliferative disease conditions. Likewise, it would be beneficial to inhibit angiogenesis in certain disease states, such as cancers, allograft rejection, retinopathies, and post-ophthalmic surgery.

It is evident that enzymes are natural targets for inorganic drugs since metals play a key enzymatic role for many enzymes, such as the zinc metalloproteinases. The coordinating ability of metals holds the attractive promise of forming stronger attachments. Thus, it would be beneficial to provide metal complexes that show effectiveness by providing inhibitory metal ions with the chelating agent merely as a carrier. Furthermore, since the products of this invention are chelating agents, they may be used to treat metal toxicity conditions such as iron, mercury or lead toxicity.

With the advent of detailed data banks and highly sophisticated molecular modeling, the design of organic-chelate-metal inhibitors has achieved a great level of precision in targeting viral enzymes. In addition, the advent of more detailed modeling techniques about enzyme structures has allowed rigorous characterization of drug-enzyme interactions. In this invention, we have sought specific targets which play key roles in cancer cell metabolism, which are unique to cancer cells or are differentially expressed in cancer cells. Likewise, we selected other metalloprotein targets which would be beneficial to stop the progression of other diseases such as inflammatory diseases.

It is evident from the published works that the role of metal ions in neurodegenerative diseases is complex. The novel agents of this invention can provide the penetrability in the CNS, the appropriate concentration range, and the right pharmacokinetic characteristics for prolong treatment which is required for these diseases. Treatment for these disorders tend to be long term rather than single dose, and the novel compounds of this invention can afford specific interactions with critical enzyme targets and metalloproteins involved in disease processes. This would separate regulatory processes form toxic effects of the pharmaceutical agents.

It is clear from the diversity of therapeutic applications of chelating agents described in the background of this invention that disease pathology correlates with abnormal metalloprotein and/or metalloenzyme activity and that both metalloprotein and metalloenzyme inhibition can be a powerful and versatile tool in the treatment of various diseases as it will be demonstrated later for the novel agents of this invention.

SUMMARY OF THE INVENTION

Based upon the foregoing, several classes of compounds have now been discovered which can be used to inactivate viruses, pathogenic prokaryotes and pathogenic eukaryotes cells. Moreover, the identification of selected target proteins in these organisms are also described. The compounds identified are either lead compounds for the development of drugs or candidates for antiviral, antiifective, and other therapeutic uses. Not every compound showing reactivity with the target metalloprotein will be able to penetrate the virus or cells and attack the target metalloprotein, in addition some will be toxic. However, identifying specific chemical groups that can react with these proteins enables rational drug design.

This invention relates to the prophylactic and therapeutic treatment of a mammal hosting a pathogenic virus, prokaryotic pathogenic organism, or eukaryotic pathogenic cell by the systemic administration of compounds having the following formula

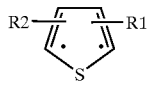

Wherein R1, which can be singly or multiply substituted in any position of the thiophene ring not already substituted by R2, is selected from the group consisting of hydrogen, alkyl and substituted alkyl wherein the alkyl portion is from 1 to 21 carbon atoms, inclusive, and isomeric forms thereof, cycloalkyls and substituted cycloalkyl, substituted oxygen, substituted nitrogen, halogen, phenyl, and substituted phenyl, —(CH$_2$)OH—, (CH$_2$)—NR3R4, and isomeric forms thereof, wherein n is an integer of from 1 to 21, inclusive, R3 and R4 are H or alkyl of from 1 to 21 carbon atoms, inclusive, and isomeric forms thereof, wherein R2, which can be singly or multiply substituted in any position of the thiophene ring not already substituted by R1, is

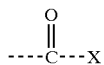

and X is the amino function of a compound selected from the group consisting of 2-hydrazine, 2-hydrazone, or 2-thiosemicarbazone; and the pharmaceutically acceptable acid-addition salts thereof, and to the use of compounds of the formula

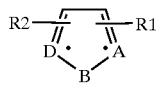

Wherein A, B, and D are selected from the group consisting of nitrogen, oxygen, sulfur, and CR1R2; R1 and R2 are as defined in claim 1, and can be attached to any ring carbon or nitrogen atom, the R1 can be multiply attached to any ring carbon atom; the R1 can be 2-carboxylic, 2-hydrazide, 2-hydrazone, and 2thiosemicarbazone; and the pharmaceutically acceptable acid-addition salts thereof.

Compounds of particular importance for the subject of this invention are the of the following formula:

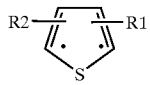

wherein R1 is in the 4 position and is a fatty acid of from 1 to 21 carbon atoms, inclusive, and isomeric forms thereof; wherein R2 is in the 3 or 5 position and is an halogen; and the pharmaceutically acceptable acid-addition salts thereof, to a mammal hosting a pathogenic organism or diseased cells.

Other compounds of particular importance for the subject invention, derived from the formula defined immediately above, have the following formulas:

4-bultyl-3-5-dichloro-2-thiophenecarboxylic acid hydrazine, 4-bultyl-3-5-dichloro-2-thiophenecarboxylic acid hydrazone and 4-bultyl-3-5-dichloro-2-thiophenecarboxylic acid thiosemicarbazone.

Furthermore, within the scope of the subject, invention are the use of compounds of the formula

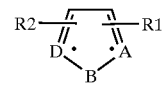

Wherein A, B, and D are selected from the group consisting of nitrogen, oxygen, sulfur, and CR1R2; R1 and R2 are as defined in claim 1, and can be attached to any ring carbon or nitrogen atom, the R1 can be multiply attached to any ring carbon atom; the R1 can be 2-carboxylic, 2-hydrazide, 2-hydrazone, and 2-thiosemicarbazone; and the pharmaceutically acceptable acid-addition salts thereof.

The chemistry and synthesis of one of the analogues described above can be described in exemplary form as shown in FIG. 2. This analogue have been shown to be 7–10 times more active than 2-thiophenecarboxylic acid against cancer cells in tissue culture.

More particularly, in one embodiment of the present invention, a method is provided for dissociating a zinc ion (or copper, or iron or other transition metal ion [TMI]) from zinc finger proteins or metalloproteinases, the method comprising contacting the metalloprotein with a compound selected from the group consisting of:

4-bultyl-3-5-dichloro-2-thiophenecarboxylic acid hydrazide, 4-bultyl-3-5-dichloro-2-thiophenecarboxylic acid hydrazone and 4-bultyl-3-5-dichloro-2-thiophenecarboxylic acid thiosemicarbazone or derivatives thereof.

A method for inactivating a metalloprotein or metalloenzyme of a pathogenic virus, pathogenic prokaryotic organisms or pathogenic eukaryotic cells, wherein the said protein comprises an amino acid sequence structure which chelates a zinc ion or a transition metal ion, said method comprising the step of contacting intravirally or intracellularly the said zinc ion or transition metal ion bound to the chelating protein structure, with a chelating compound which dissociates the metal ion protein complex selected from the group consisting of the following compounds:

Examples of such compounds include, but are not limited to the following:

1. Furoic acid having the formula described above;
2. 2-Thiophenecaboxylic acid having the formula shown in FIG. 1;
3. Halogenated furoic acid as defined in claim 1;
4. Halogenated 2-thiophenecarboxylic acid as defined in claim 1;
5. Hydrazides of furoic acid or 2-thiophenecarboxylic acid having the formula —C—NH—NH—R, where —C is attached to position 2 of the thiophene ring;
6. Hydrazones of furoic acid or 2-thiophenecarboxylic acid having the formula —CH═N—NH—C═O, where —C is attached to position 2 of the thiophene ring;
7. Thiosemicarbazones having the formula —CH═N—NH—C═S—, where C is in position 2 of the thiophene ring;
8. Halogenated furoic acid, halogenated 2-thiophenecarboxylic acid, and derivatives thereof where the halogen is selected from the group consisting of F, I, Br, and Cl;

The compounds of 1 to 8 in which one or more of the ring residues in positions 3 or 4 have been replaced by a fatty acid side chain of 2 to 21 carbons.

The compounds of 1 to 8 coordinately complexed to cupric ions, or to ferric ions, or to a toxic metal ion such as platinum.

A method for inactivating a metalloprotein or metalloenzyme of a pathogenic virus, pathogenic prokaryotic organisms or pathogenic eukaryotic cells, wherein the said protein comprises an amino acid sequence structure which chelates a zinc ion or a transition metal ion (TMI), said method comprising the step of contacting intravirally or intracellularly the said zinc ion or TMI bound to the chelating protein structure with a chelating compound which dissociates the metal ion from the protein complex, said chelating compound selected from the group consisting of the following compounds:

2-furoic acid; 2-furoic acid hydrazide; Tetrahydro-2-furoic acid; 3,5-dibromo-2-furoic acid;

3,4,5-tribromo-2-furoic acid; 2,5-dimethoxytetrahydro-2-furoic acid hydrazine;

5-[2-Chloro-5-(trifluoromethyl)phenyl]-2-furoic acid;

5-[3-(trifluoromethyl)phenyl]-2-furoic acid;

5-(2-Nitrophenyl)-2-furoic acid;

5-(3-Nitrophenyl)-2-furoic acid;

5-(4-Chloro-2-nitrophenyl)-2-furoic acid;

5-(4-Chlorophenyl)-2-furoic acid;

5-(4-Methyl-2-nitrophenyl)-2-furoic acid;

5-(4-Nitrophenyl)-2-furoic acid;

5-Bromo-2-furoic acid;

5-Chloro-2-furoic acid;

5-Nitro-2-furoic acid

5-Nitrofuran-2-carboxylic acid.

2-thiophenecarboxylic acid; 3,4,5-trichloro-2-thiophenecarboxylic acid; 2-thiophenecarboxylic acid hydrazide; 2-thiophenecarboxylic acid hydrazone;

3-methyl-2-thiophenecarboxylic acid;

5-bromo-2-thiophenecarboxylic acid hydrazone;

5-methyl-2-thiophenecarboxylic acid;

5-chloro-2-thiophenecarboxylic acid;

and 5-chloro-2-thiophenecarboxylic acid hydrazone.

In yet another embodiment of the present invention a method for selecting a compound capable of dissociating a zinc chelated with a CCCC [or a CHCH, or other permutations of C and H] zinc finger of a viral protein is as follows: a) contacting the CCCC zinc finger of the CCCC protein with a chelating agent; and b) detecting the dissociation of the zinc atom from the protein. Such chelating agents include:

2-furoic acid; 2-furoic acid hydrazide; Tetrahydro-2-furoic acid; 3,5-dibromo-2-furoic acid;

3,4,5-tribromo-2-furoic acid; 2,5-dimethoxytetrahydro-2-furoic acid hydrazine;

5-[2-Chloro-5-(trifluoromethyl)phenyl]-2-furoic acid;

5-[3-(trifluoromethyl)phenyl]-2-furoic acid;

5-(2-Nitrophenyl)-2-furoic acid;

5-(3-Nitrophenyl)-2-furoic acid;

5-(4-Chloro-2-nitrophenyl)-2-furoic acid;

5-(4-Chloro-phenyl)-2-furoic acid;

5-(4-Methyl-2-nitrophenyl)-2-furoic acid;

5-(4-Nitrophenyl)-2-furoic acid;

5-Bromo-2-furoic acid;

5-Chloro-2-furoic acid;

5-Nitro-2-furoic acid

5-Nitrofuran-2-carboxylic acid.

2-thiophenecarboxylic acid; 3,4,5-trichloro-2-thiophenecarboxylic acid; 2-thiophenecarboxylic acid hydrazide; 2-thiophenecarboxylic acid hydrazone;

3-methyl-2-thiophenecarboxylic acid;

5-bromo-2-thiophenecarboxylic acid hydrazone;

5-methyl-2-thiophenecarboxylic acid;

5-chloro-2-thiophenecarboxylic acid;

The target proteins include but are not limited to: 1) MPS-1/S27 ribosomal protein; 2) the viral proteins described in Table 2; 3) LF protein of the Anthrax bacteria, 4) amyloid beta monomeric precursors of Alzheimer's disease; and 5) matrix metalloproteinases. The selection method utilizes detection techniques such as: Nuclear Magnetic Resonance (NMR), high pressure liquid chromatography (HPLC), capillary electrophoresis, immunoblotting, release of radioactive isotope of metal ion, detecting fluorescence, and detecting mobility changes in gel shift assays.

It is among the objects of the present invention to provide specifics compounds which can inhibit the growth and proliferation of cells by blocking the activity of metal ion-containing proteins and metalloproteases.

Another object of the present invention is to provide a compound which can retard the growth and proliferation of target infective organisms including viruses, bacteria, fungi parasites or other infective agents by blocking the activity of metal ion-containing proteins.

Another object of the present invention is to provide a compound which can retard the growth and proliferation of target viruses or virus infected cells by blocking the activity of transition metal ion-containing protein structures such as zinc finger proteins or metalloenzymes associated with viral replication.

Another object of the invention is to provide such a compound to retard angiogenesis in malignant tumors by inhibiting metalloenzymes associated with neovascularization.

It is still another object of the present invention to provide a compound that can retard the growth of premalignant and malignant cells such as virally, chemically and spontaneously transformed cells.

Another objects of the present invention is to provide a compound that can retard the growth of premalignant and malignant cells such as virally, chemically and spontaneously transformed cells and be administered by any acceptable route, including orally, with substantial effectiveness and minimal side effects.

It is also among the objects of the present invention to provide a new treatment for patients suffering from various forms of viral infections by utilizing the novel properties of metal chelating agents as a chemotherapeutic anti-viral agent.

It is another object of the present invention to provide an agent that can halt the proliferation and transmission of viruses containing zinc finger proteins or metalloproteinases as essential viral proteins.

Another object of the invention is to provide a method of disrupting the function of metal containing protein structures containing metals other than zinc, such as iron-finger and other proteins with metal binding motifs heretofore unidentified by the administration of a metal chelating agent, both topically and systemically Another object of the invention is to provide a product which can be spray in the nostrils or inhaled to prevent or control upper respiratory diseases such as influenza, rhinoviruses or pulmonary cancer.

Another object of the invention is to provide an anti-inflammatory compound that is effective in a broad range of inflammatory disorders including inflammatory response to infections and to chemical damage or radiation including, but not limited to, ultraviolet, atomic or medical radiation.

Yet another object of the invention is to provide such chelating agents in a relatively safe and nontoxic form such as 2-thiophenecarboxylic acid, its derivatives or related or similar compounds for both topical and systemic use.

Another object of the invention is to provide a topical preparation of metal chelating agents such as furoic acid, 2-thiophenecarboxylic acid (2-TH) or its derivatives to treat virally induced or spontaneous proliferative diseases of the skin or mucous membranes in human and animal subjects.

It is still another object of the present invention to provide an intravaginal preparation containing metal chelating agents such as furoic acid, 2-TH acid, or derivatives thereof that can prevent or retard sexually transmitted diseases caused by viruses or other causative agents containing zinc finger proteins or other zinc binding motif in their structure.

Still another object of the present invention is to provide a preparation containing chelating agents such as furoic acid, 2-TH acid or derivatives thereof that halts the progression of viral infections or proliferative diseases that is non-toxic to normal cells, relatively inexpensive and well suited for its intended purposes.

According to the invention, the main object is to provide a method of treatment and compound used in the method, for example, metal chelating compounds, such as 2-thiophenecarboxylic acid or derivatives thereof, for the treatment of infective or proliferative diseases, inflammatory responses, and cancers in human and animal subjects. The invention can be used orally or topically to treat or control a wide spectrum of proliferative diseases or conditions, both spontaneous or induced by viruses, bacteria, fungi parasites, chemicals, or radiation. The metal chelating compounds bind metal, for example iron or transition metal ions such as zinc, required by enzymes, or by transcription proteins found in viruses or malignant cells. By way of further example, the metal chelating compound, for example 2-thiophenecarboxylic acid or its derivatives, is used to bind the zinc contained in the zinc finger protein M1 common to the influenza viruses strains, thereby inactivating the virus and preventing the exit of RNA containing viruses or particles from the cells.

In one embodiment of the invention 2-TH acid in 500 mg capsules given in dosages ranging from 500 mg per day to 2000 mg per day, or more has been demonstrated by mathematical modeling to be effective in reducing the size of tumors, such as cancerous lymph nodes and inducing apoptosis in the cancerous tumor cells.

One embodiment of a topical preparation consists of a solution of the chelator, for example, 0.01% to 99%, preferably 5% to 25%, furoic acid or 2-TH acid in an appropriate vehicle, such as deionized water, buffer or other solvent, and is applied to the lesion three times a day. The preparation can be applied to skin to control acne, warts, herpes infections and to toe nails, to treat fungal infections. In another embodiment, the topical preparation consists of an ointment or cream containing approximately 0.5% to 99%, preferably 5% to 10% of furoic acid or 2-TH acid which is applied once or twice daily to the lesion. The ointment or cream can be instilled intravaginally to retard sexually transmitted viral diseases.

The various embodiments of the topical preparations can be used to treat papilloma and herpes viral diseases and to retard the papilloma, herpes and HIV viruses as well as proliferative diseases such as psoriasis and skin cancer.

Various derivatives that maintain their activity and stability after systemic administration are provided. Slow release oral formulations can be used to treat diseases for the digestive tract. The active derivatives can be administered orally, parenterally, by inhalation, transdermally or by any other appropriate method to control proliferative diseases, cancers, viral infections, HIV, and pulmonary Anthrax or any other condition wherein the causative agent includes a zinc-containing protein, whether the zinc-containing protein is a zinc finger protein, a zinc ring protein, or other type of zinc or metal containing structure heretofore unidentified or undetected, wherein the metal containing segment is required for protein stability and configuration and/or enzymatic activity.

It will be appreciated that other appropriate chelating materials such as the derivative of 2-TH acid may be used. It also will be appreciated that, although 1% to 5% topical preparations of furoic acid and 2-TH acid are described, a broader range of concentrations may be used. Further, the systemic doses may be altered or adjusted to ranges greater or lesser than those described, depending on toxicity and patient response, without departing from the scope of the appended claims.

It will be appreciated that some of the hydrophobic compounds of this invention can act intracellularly at low concentrations (pM to uM). Thus, the agents of this invention can penetrate cells, reach the target metalloprotein which is present at low intracellular concentrations (uM) and inactivate it.

It will be also appreciated that while the dose-response relationships of the chelating drugs of the prior art in general have a sharp square wave for the dose-response relationship and are non-specific, the compounds of the instant invention are target specific and have dose-response relationships for systemic use that are sigmoidal and thus have a wide range of therapeutic concentrations. Therefore, the agents of the instant invention are highly compatible with acceptable target to background therapeutic/toxic ratios.

Other features, objectives and advantages of the invention and its preferred embodiments will become apparent from the detail description which follows. Table 1 summarizes some of the medical applications of the agents of this invention.

TABLE 1

The agents of this invention:
Specific Chelating Agents and Metal Complexes of these Agents as Therapeutic Agents to Disrupt Target Zinc Finger Protein and to Inhibit Target Metalloenzymes

| | |
|---|---|
| I. | Applications to Normal and Abnormal Physiology |
| | Cancer |
| | Angiogenesis |
| | Proliferative diseases (e.g. psoriasis) |
| | Hypertension |
| | Matrix Metalloproteinases |
| | Neurodegenerative diseases (e.g. Alzheimer's; Parkinson's disease) |
| | Inflammation (e.g. Arthritis) |
| | Organ transplant |
| II. | Applications to Infections |
| | A. Viral (Table 2) |
| | B. Nonviral: Bacteria, Fungi, and parasites |

TABLE 1-continued

The agents of this invention:
Specific Chelating Agents and Metal Complexes of these Agents
as Therapeutic Agents to Disrupt Target Zinc Finger Protein
and to Inhibit Target Metalloenzymes III. Toxicity Applications Heavy Metals (e.g., depleted uranium, lead nickel, tungsten)
    Poison Ivy dermatitis IV. Miscellaneous Enzymes Leukotriene $A_4$ hydrolase V. Metal-facilitated Inhibition Copper (II) chelates as inhibitors of HIV proteases

DEFINITIONS

Figure 1:
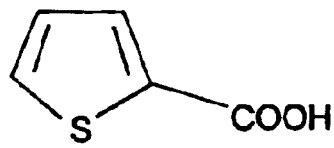
FIG. 1 shows the chemical structures of 2-thiophenecarboxylic acid, 2-thiophenecarboxylic acid hydrazide; 3,4,5-trichloro-2-thiophenecarboxylic acid hydrazone; and 4-butyl-3-chloro-2-thiophenecarboxylic acid thiosemicarbazone.
Figure 1:
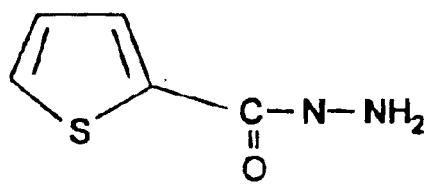
Figure 1:
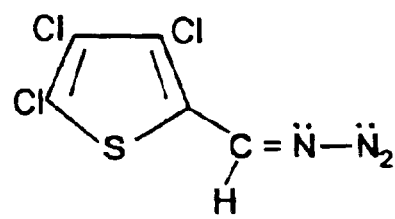
Figure 1:
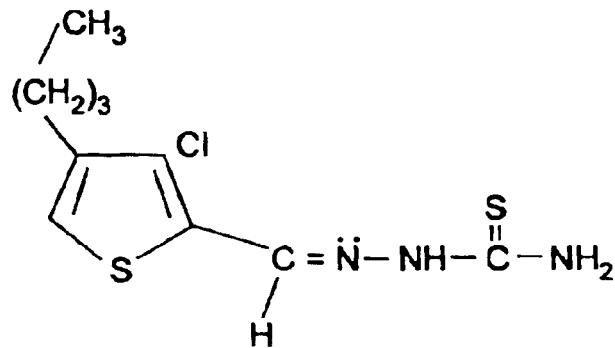

"Penetrating" refers to the act of bringing the drug into an intracellular or viral compartment which will place the active moiety of the drug into adequate proximity to the target protein such as the reaction will occur and the target protein will be inactivated.

"Zinc finger protein disrupting agent" refers to the action of a chelating agent that specifically ejects the zinc from the protein, resulting in a conformational change of the protein that renders the protein inactive.

"Chelating agent catalytic inhibitor of metalloenzymes" refers to the inhibitory action of a specific chelating agent that binds to the zinc present in the catalytically active site of the enzyme and renders the site catalytically inactive.

"Organometallic compound" refers to a specific chelating agent tightly bound to a toxic metal that inhibits the active site of a metalloenzyme by replacing the naturally occurring metal ion in the enzyme.

DETAILED DESCRIPTION OF THE INVENTION AND PREFERRED EMBODIMENTS

From the foregoing it appears that it would be beneficial to have a product that can interfere with the formation or action of certain zinc finger proteins or metalloproteinases to inhibit the progress of pathogenic viruses, bacteria, fungus, malignancies, neurodegenerative diseases, etc., dependent upon zinc finger or metalloproteinases for their pathogenicity. Furthermore, it would be beneficial to provide a product that can halt the growth of proliferative cells, such as malignant cells by chelating metal ions from zinc-dependent or transition metal ion (e.g. copper, iron, etc.) dependent proteins and enzymes necessary for the replication of the malignant cells. Furthermore, since the products can chelate metals, such as iron, they have a role in metal toxicity states, such as iron or lead toxicity.

In view of the foregoing, there exists a need in the art for a pathogenic target protein, mechanism and methods which can be used to predict compounds that can effectively disrupt specific zinc-fingers or other zinc-binding motif and, in turn, inactivate the virus, prokaryotic or eukariotic cell of choice. Similarly, there exists a need for compounds that can be used effectively to inactivate catalytic zinc bound to the active site of metalloproteinases and, subsequently, inactivate the virus, prokaryotic or eukaryotic cell of choice.

The present invention provides a descriptive mechanism for the disruption of zinc fingers and other conserved structures that contain metal ions essential for the function of metalloproteins. The disruption is accomplished by several classes of chemical compounds which are identified by their capacity to react with and disrupt zinc finger and other metalloproteins essential for cellular and viral functions.

The pharmacological and therapeutic characteristics of the agents of the instant invention will be described in detail in the following sections. Data generated from results of in vitro assays, animal models, and computer modeling show the utility of this invention in the medical field.

Although the utility of this invention is multiple, we present a few examples that provide proof of the utility of this invention in numerous medical fields such as cancer, infectious diseases, and neurodegenerative diseases.

The novelty and non-obviousness of the agents of the instant invention is demonstrated by the fact that the majority of the chelating agents utilized prior to the instant invention are too harsh to be used systemically in animals and humans even for short time periods. One of the main problems with the chelating agents currently available for systemic treatments is that they lack specificity and have dose-response relationships that are too sharp to be useful in systemic clinical applications. In fact, with prolong use, most of these agents cause a body depletion of transition metal ions essential for cellular respiration with the consequent development of patient anergia.

While the dose response relationships of the drugs of the prior art in general have a sharp square wave for the dose-response relationship and are non-specific, the compounds of the instant invention are target specific and have dose-response relationships for systemic use that are sigmoidal and thus they have a wide range of therapeutic concentrations. Thus the agents of the instant invention are highly compatible with acceptable target to background therapeutic/toxic ratios.

The present invention provides a descriptive mechanism for the destruction of virally infected cells and proliferating cancer cells induced by the chemotherapeutic agents of this invention. The experimental evidence supports the conclusion that zinc deficiency resulting from exposure of culture cells to membrane-permeable $Zn^{2+}$-chelators, can induced apoptosis in virally transformed cells while normal cells remain unaffected. Furthermore, iron deficiency resulting from exposure of cultured cells to membrane-permeable $Fe^{2+}$-chelators, can induced apoptosis in virally transformed cells while normal cells remain unaffected. An intracellular pool of chelatable $Zn^{2+}$ plays a critical role in apoptosis, most likely by modulating the activity of zinc finger proteins and inhibiting the enzymatic activity of zinc containing metalloenzymes, which are essential for maintenance of cellular and viral structure and cancer cell proliferation The intracellular pool of chelatable $Fe^{2+}$ also plays a critical role in apoptosis, most likely by modulating the activity of $Fe^{2+/3+}$ containing proteins such as ribonucleotide reductase, which are essential for maintenance of viral structure and function and cancer cell proliferation.

The present invention contemplates the use of metal chelating agents such as furoic acid, 2-thiophenecarboxylic acid (2-TH) and their derivatives, analogs and related chemical as defined above, in the prevention and treatment of diseases and toxicities caused by heavy metals such as iron, copper, nickel, lead, uranium, and tungsten. The chelating agent can be administered to the patient in oral form or in injectable form. Other forms of administration include transdermal, rectal suppositories, intranasally, inhalation, or any other pharmacologically acceptable form Chelation therapy with the heavy-metal antagonist of this invention results in the binding of the toxic metal to the chelating agent. Chelation therapy will promote the excretion of the inorganic heavy metal. The inactive chelate-heavy metal is then eliminated from the body. Chelation therapy is indicated in symptomatic patients of patients with toxic levels of a given toxic metal. The agents of this invention can be combined with other chelators such as EDTA, dimercaprol, D-penicillamine and succimer. When environmental exposure to heavy metals is a concern, the heavy-metal antagonists of this invention can be used to prevent intoxication.

In this patent application we also present novel organometallic agents that are derivatives of the chelating agents of this invention. It is pertinent to mention here that organometallic compounds have been used in medicine as antiseptics and antimicrobial for several centuries. These organometallic agents are known to exert their effects by inhibiting the active sites of metalloenzymes. The organometallic compounds of this invention can carry the metal ion as a toxic agent for the specific virus, microbe or cancer cell. For example, the inhibition of zinc metalloproteases in bacteria and fungi is within the scope of this invention. Screening a large number of toxic metal ions against the metalloproteases of bacteria and fungi in the presence and absence of the chelating agents of this invention can show an increase in the activity of the compound tested in the presence of the toxic metal. This inhibition is competitive, indicating that the organometallic inhibitor binds to the active site of the metalloenzyme. For example, trivalent arsenical drugs of this invention may be used in the treatment of trypanosome-mediated illnesses such as African sleeping disease and Chaga's disease. Trivalent arsenical of this invention bind arsenic by interaction with the compound thiol groups. The mechanism for their activity is due to an interaction of arsenic with the parasite target protein thiol groups of the active site of the metalloenzyme. Complexes of metal ions can show effectiveness as antifungal agents such as the pathogenic yeast Candida albicans. Another example is Mycloplasm which lacks a rigid cell wall. The agents of the instant invention can act on metalloenzymes of Mycoplasm. Furthermore, copper is known to be toxic to mycoplasm. The agents of this invention can be use as copper carriers to control Mycoplasm infection. Understanding better the effectiveness of the agents of this invention against infection will also enhance the development of anticancer and antiviral agents.

All the applications of the therapeutic drugs of this invention are designed to combat abnormal microorganisms and abnormal cells while leaving the surrounding normal tissues intact. In this context, the agents of this invention operate as specific and selective toxins.

1. General Methods for the Identification of the Agents of this Invention

The present invention provides several classes of compounds which can be used to inactivate viruses, prokaryotic and eukaryotic cells. The method consists in attacking zinc finger proteins at the zinc finger motif structural site with the chelating agents of this invention which will result in the ejection of zinc, with the consequent disruption of the zinc finger protein structure and function. The compounds of the present invention can also be used to inhibit catalytically active centers of metalloenzymes by forming a complex consisting of the active compound bound to the metal ion present at the catalytic active site of the enzyme. This complex formed by the active compound and the catalytically active metal ion coordinately bound to the amino acids of the enzyme active site renders the metalloenzyme inactive.

In particular, the present invention also describes a set of specific tests and reagents that can be used to screen and identify compounds based on their ability to react with and disrupt metalloproteins. It will be apparent to those skilled in the art that after inactivation, the viral protein, or prokaryotic, or eukaryotic protein so treated, can be used, for example as vaccines or as a components in assays for the diagnosis of infections.

There are several general methods that can be used to detect the activity of the compounds of the present invention which are briefly described for illustrative purposes only. An example is the release of radioactive zinc-65-, copper-64-, or iron-59 from labeled protein. The labeled protein and precipitating reagents can be used to detect the ability of the compounds to remove the radioactive metal from the protein by determining the bound and free radioactive metal. Capillary Zone Electrophoresis (CZE) can be use to easily detect the activity of the compounds interacting with specific metalloproteins. The compounds that react with the metalloprotein and remove the transition metal produce a change in the configuration and charge of the protein which alters the electrophoretic mobility of the protein with respect to the untreated metalloprotein. Thus, the electrophoretic mobility of the treated protein will be different than the control, untreated protein. In addition, the following assays can be used. Gel Mobility shift assays can be use to detect the activity of the compounds interacting with specific metalloproteins by detecting changes in protein mobility with and without the agent. Fluorescent zinc chelators can be used to monitor the release of zinc from the zinc finger or metalloprotein under study. Nuclear Magnetic Resonance (NMR) can also be used to monitor the loss of zinc or other transition metal from the metalloprotein in the presence and absence of the compound. By using computer modeling, compounds with specific properties can also be found by creating three-dimensional molecular structures and inspecting the interactions with the active metal containing sites of the target protein. The drug can also be tested for activity by examining its effects on virus infected cells, cultured bacteria and cells. Finally, the drugs can be tested in adequate animal model systems to determine their therapeutic effects and toxicities.

There are several general enzymatic methods that can be used to detect the activity of the compounds of the present invention which are briefly described for illustrative purposes only. For example, the competitive inactivation of the zinc metalloenzyme, Leukotriene $A_4$ hydrolase ($LTA_4H$) by the agents of the present invention can be studied as follows. The enzyme is competitively inactivated by a structural isomer of 4-pentyl-thiophenecarboxylic acid hydrazide (P-TAH) that interacts with the catalytically active zinc and with the hydrophobic residues surrounding the catalytically active zinc site. Kinetic analysis shows that the inactivation is directly coupled to catalysis and proportional to product formation. Electrospray mass spectrometry will show a shift in molecular weight of inactivated enzyme compatible with the coupling of $LTA_4H$ in a 1:1 stoichiometry between the drug (P-TAH) and the protein ($LTA_4H$). The competitive inhibitor P-TAH prevents the covalent binding of $LTA_4$ to the enzyme, indicating that it occurs at the active site. This shows the high specificity for the agent of this invention, P-TAH, which is demonstrated by the narrow substrate specificity of LTA4.

2. Compound Chemistry

Detailed studies of the reaction mechanisms of the drugs to be described here, which include interaction with specific metalloproteins, and the effects of the drugs on cultured cancer cells, presented for the first time in this application, reveals that certain chelating compounds having the functional groups described in this invention have suitable characteristics as chemotherapeutic agents, antiviral agents, and biological response modifiers The present invention provides several classes of compounds which can be used to inactivate metalloproteins and metalloenzymes involved in pathological conditions. Compounds which interact with metalloproteins and metalloenzymes include but are not limited to the following:

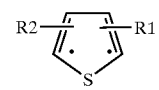

Wherein R1, which can be singly or multiply substituted in any position of the thiophene ring not already substituted by R2, is selected from the group consisting of hydrogen, alkyl and substituted alkyl wherein the alkyl portion is from 1 to 21 carbon atoms, inclusive, and isomeric forms thereof, cycloalkyls and substituted cycloalkyl, substituted oxygen, substituted nitrogen, halogen, phenyl, and substituted phenyl, —(CH$_2$)$_n$—OH, —(CH$_2$)$_n$—NR$_3$R4, and isomeric forms thereof, wherein n is an integer of from 1 to 21, inclusive, R3 and R4 are H or alkyl of from 1 to 21 carbon atoms, inclusive, and isomeric forms thereof; wherein R2, which can be singly or multiply substituted in any position of the thiophene ring not already substituted by R1, is

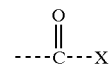

and X is the amino function of a compound selected from the group consisting of 2-hydrazine, 2-hydrazone, or 2-thiosemicarbazone; and the pharmaceutically acceptable acid-addition salts thereof, and to the use of compounds of the formula

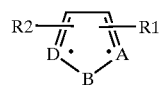

Wherein A, B, and D are selected from the group consisting of nitrogen, oxygen, sulfur, and CR1R2; R1 and R2 are as defined in claim 1, and can be attached to any ring carbon or nitrogen atom, the R1 can be multiply attached to any ring carbon atom; the R1 can be 2-carboxylic, 2-hydrazide, 2-hydrazone, and 2-thiosemicarbazone; and the pharmaceutically acceptable acid-addition salts thereof.

Compounds of particular importance for the subject of this invention are the of the following formula:

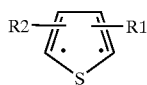

wherein R1 is in the 4-position and is a fatty acid of from 1 to 21 carbon atoms, inclusive, and isomeric forms thereof; wherein R2 is in the 3 or 5 position and is an halogen; and the pharmaceutically acceptable acid-addition salts thereof, to a mammal hosting a pathogenic organism or diseased cells.

Other compounds of particular importance for the subject invention, derived from the formula defined immediately above, have the following formulas:
4-bultyl-3-5-dichloro-2-thiophenecarboxylic acid hydrazide, 4-bultyl-3-5-dichloro-2-thiophenecarboxylic acid hydrazone and 4-bultyl-3-5-dichloro-2-thiophenecarboxylic acid thiosemicarbazone.

Furthermore, within the scope of the subject invention are the use of compounds of the formula

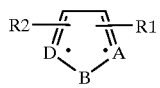

Wherein A, B, and D are selected from the group consisting of nitrogen, oxygen, sulfur, and CR1R2; R1 and R2 are as defined in claim 1, and can be attached to any ring carbon or nitrogen atom, the R1 can be multiply attached to any ring carbon atom; the R1 can be 2-carboxylic, 2-hydrazide, 2-hydrazone, and 2-thiosemicarbazone; and the pharmaceutically acceptable acid-addition salts thereof.

Figure 2:
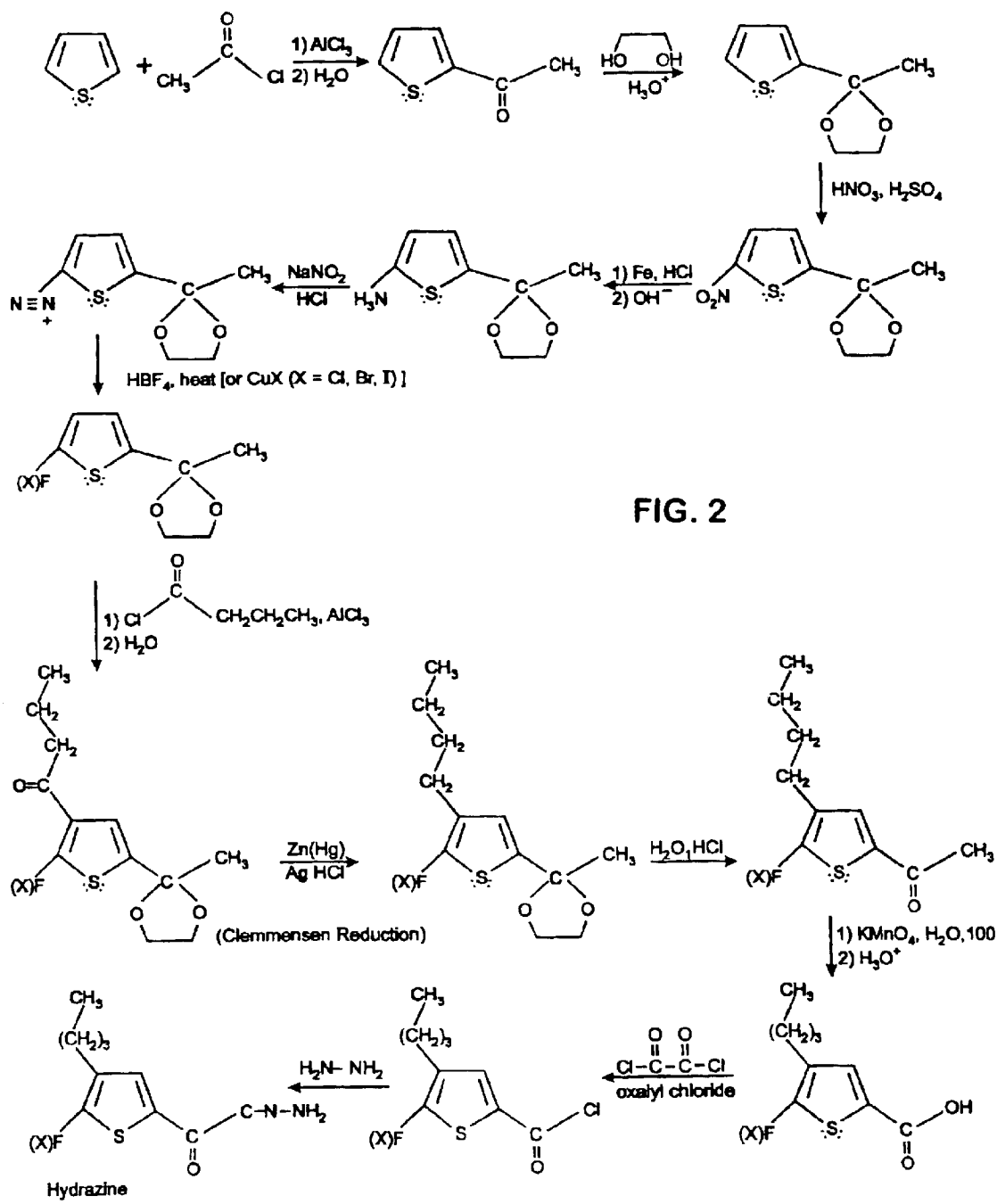
FIG. 2 illustrates the chemistry and synthesis of 4-butyl-3-chloro-2-thiophenecarboxylic acid hydrazide.
Figure 3:
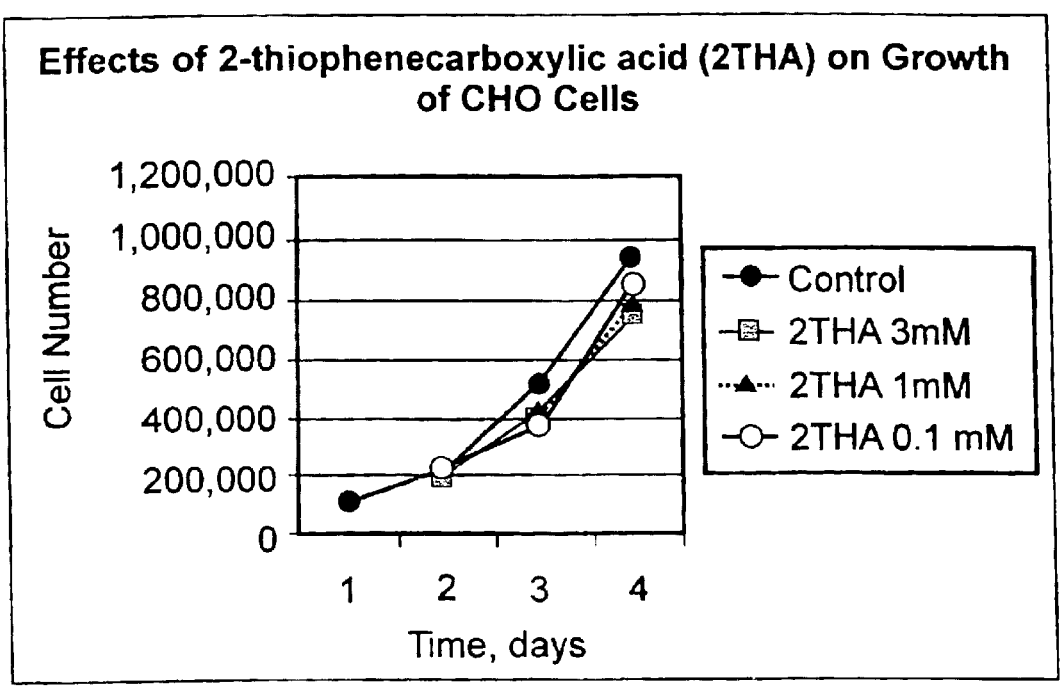
FIG. 3 illustrates the effects of different concentrations of 2-thiophenecarboxylic acid on the growth CHO cells.

The chemistry and synthesis of one of the analogues described above can be described in exemplary form as shown in FIG. 2. This analogue have been shown to be 7–10 times more active than 2-thiophenecarboxylic acid against cancer cells in tissue culture.

More particularly, in one embodiment of the present invention, a method is provided for dissociating a zinc ion (or copper, or iron or other transition metal ion [TMI]) from zinc finger proteins or metalloproteinases, the method comprising contacting the metalloprotein with a compound selected from the group consisting of:
4-bultyl-3-5-dichloro-2-thiophenecarboxylic acid hydrazide, 4-bultyl-3-5-dichloro-2-thiophenecarboxylic acid hydrazone and 4 bultyl-3-5-dichloro-2-thiophenecarboxylic acid thiosemicarbazone or derivatives thereof.

A method for inactivating a metalloprotein or metalloenzyme of a pathogenic virus, pathogenic prokaryotic organisms or pathogenic eukaryotic cells, wherein the said protein comprises an amino acid sequence structure which chelates a zinc ion or a transition metal ion, said method comprising the step of contacting intravirally or intracellularly the said zinc ion or transition metal ion bound to the chelating protein structure, with a chelating compound which dissociates the metal ion protein complex selected from the group consisting of the following compounds:

Examples of such compounds include, but are not limited to the following:

1. Furoic acid having the formula described above;
2. 2-Thiophenecaboxylic acid having the formula shown in FIG. 1;
3. Halogenated furoic acid as defined in claim 1;
4. Halogenated 2-thiophenecarboxylic acid as defined in claim 1;
5. Hydrazides of furoic acid or 2-thiophenecarboxylic acid having the formula —C—NH—NH—R, where —C is attached to position 2 of the thiophene ring;
6. Hydrazones of furoic acid or 2-thiophenecarboxylic acid having the formula —CH=N—NH—C=O—, where —C is attached to position 2 of the thiophene ring;
7. Thiosemicarbazones having the formula —CH=N—NH—C=S—, where C is in position 2 of the thiophene ring;
8. Halogenated furoic acid, halogenated 2-thiophenecarboxylic acid, and derivatives thereof where the halogen is selected from the group consisting of F, I, Br, and Cl;

The compounds of 1 to 8 in which one or more of the ring residues in positions 3 or 4 have been replaced by a fatty acid side chain of 2 to 21 carbons.

The compounds of 1 to 8 coordinately complexed to cupric ions, or to ferric ions, or to a toxic metal ion such as platinum.

A method for inactivating a metalloprotein or metalloenzyme of a pathogenic virus, pathogenic prokaryotic organisms or pathogenic eukaryotic cells, wherein the said protein comprises an amino acid sequence structure which chelates a zinc ion or a transition metal ion (TMI), said method comprising the step of contacting intravirally or intracellularly the said zinc ion or TMI bound to the chelating protein structure with a chelating compound which dissociates the metal ion from the protein complex, said chelating compound selected from the group consisting of the following compounds:

2-furoic acid; 2-furoic acid hydrazide; Tetrahydro-2-furoic acid; 3,5-dibromo-2-furoic acid;

3,4,5-tribromo-2-furoic acid; 2,5-dimethoxytetrahydro-2-furoic acid hydrazine; 5-[2-Chloro-5-(trifluoromethyl)phenyl]-2-furoic acid;

5-[3-(trifluoromethyl)phenyl]-2-furoic acid;

5-(2-Nitrophenyl)-2-furoic acid;

5-(3-Nitrophenyl)-2-furoic acid;

5-(4-Chloro-2-nitrophenyl)-2-furoic acid;

5-(4-Chlorophenyl)-2-furoic acid;

5-(4-Methyl-2-nitrophenyl)-2-furoic acid;

5-(4-Nitrophenyl)-2-furoic acid;

5-Bromo-2-furoic acid;

5-Chloro-2-furoic acid;

5-Nitro-2-furoic acid

5-Nitrofuran-2-carboxylic acid.

2-thiophenecarboxylic acid; 3,4,5-trichloro-2-thiophenecarboxylic acid; 2-thiophenecarboxylic acid hydrazide; 2-thiophenecarboxylic acid hydrazone;

3-methyl-2-thiophenecarboxylic acid;

5-bromo-2-thiophenecarboxylic acid hydrazone;

5-methyl-2-thiophenecarboxylic acid;

5-chloro-2-thiophenecarboxylic acid;

and 5-chloro-2-thiophenecarboxylic acid hydrazone.

In yet another embodiment of the present invention a method for selecting a compound capable of dissociating a zinc chelated with a CCCC [or a CHCH, or other permutations of C and H] zinc finger of a viral protein is as follows: a) contacting the CCCC zinc finger of the CCCC protein with a chelating agent; and b) detecting the dissociation of the zinc atom from the protein. Such chelating agents include:

2-furoic acid; 2-furoic acid hydrazide; Tetrahydro-2-furoic acid; 3,5-dibromo-2-furoic acid;

3,4,5-tribromo-2-furoic acid; 2,5-dimethoxytetrahydro-2-furoic acid hydrazine;

5-[2-Chloro-5-(trifluoromethyl)phenyl]-2-furoic acid;

5-[3-(trifluoromethyl)phenyl]-2-furoic acid;

5-(2-Nitrophenyl)-2-furoic acid;

5-(3-Nitrophenyl)-2-furoic acid;

5-(4-Chloro-2-nitrophenyl)-2-furoic acid;

5-(4-Chlorophenyl)-2-furoic acid;

5-(4-Methyl-2-nitrophenyl)-2-furoic acid;

5-(4-Nitrophenyl)-2-furoic acid;

5-Bromo-2-furoic acid;

5-Chloro-2-l furoic acid;

5-Nitro-2-furoic acid

5-Nitrofuran-2-carboxylic acid.

2-thiophenecarboxylic acid; 3,4,5-trichloro-2-thiophenecarboxylic acid; 2-thiophenecarboxylic acid hydrazide; 2-thiophenecarboxylic acid hydrazone;

3-methyl-2-thiophenecarboxylic acid;

5-bromo-2-thiophenecarboxylic acid hydrazone;

5-methyl-2-thiophenecarboxylic acid;

5-chloro-2-thiophenecarboxylic acid;

The target proteins include but are not limited to: 1) MPS-1/S27 ribosomal protein; 2) the viral proteins described in Table 2; 3) LF protein of the Anthrax bacteria; 4) amyloid beta monomeric precursors of Alzheimer's disease; and 5) matrix metalloproteinases. The selection method utilizes detection techniques such as: Nuclear Magnetic Resonance (NMR), high pressure liquid chromatography (HPLC), capillary electrophoresis, immunoblotting, release of radioactive isotope of metal ion, detecting fluorescence, and detecting mobility changes in gel shift assays.

Other features, objectives and advantages of the invention and its preferred embodiments will become apparent from the detail description which follows.

3. Administration of Compounds in vivo

The compounds of the present invention, identified as those that inactivate in vitro specific metalloproteins, penetrate viruses, bacteria and cells, and inactivate in vivo the target metalloproteins can be used to treat metalloprotein mediated diseases such as AIDS, Anthrax, cancer, etc, thereby inactivating the pathogenic life form.

The compounds used in the present method of treatment are administered in any suitable manner alone or with suitable pharmaceutical carriers. There are a wide variety of suitable formulations of the pharmaceutical compositions utilizing the agents of the present invention.

For oral administration, the formulations can consist of the following: 1) liquid solutions utilizing diluents such as water, saline, syrups; 2) tablets, capsules, or powders; 3) suspensions and emulsions. The active components can be administered as aerosol formulations to be administered by inhalation. For rectal administration suitable suppository bases including hydrocarbons can be utilized. For parenteral administration such as intravenous, intramuscular, intradermal, subcutaneous, intraperitoneal, and intraarticular delivery, aqueous and non-aqueous isotonic buffered sterile injections can be used.

The doses administered to a patient should be sufficient to produce a therapeutic response with acceptable adverse side effects which will result in the shortening or halting of the disease condition. The dose will be determined by the surface area or body weight of the patient to be treated and the severity of the condition. To determine the effective amount of the active ingredient in the treatment or prophylaxis of metalloprotein-mediated diseases such as Anthrax, the practitioner will evaluate the circulating serum levels, toxicity and response to the agent.

The compounds of this invention can be combined with conventional therapies, including cytotoxic agents, antibiotics, and biological response modifiers.

Figure 9:
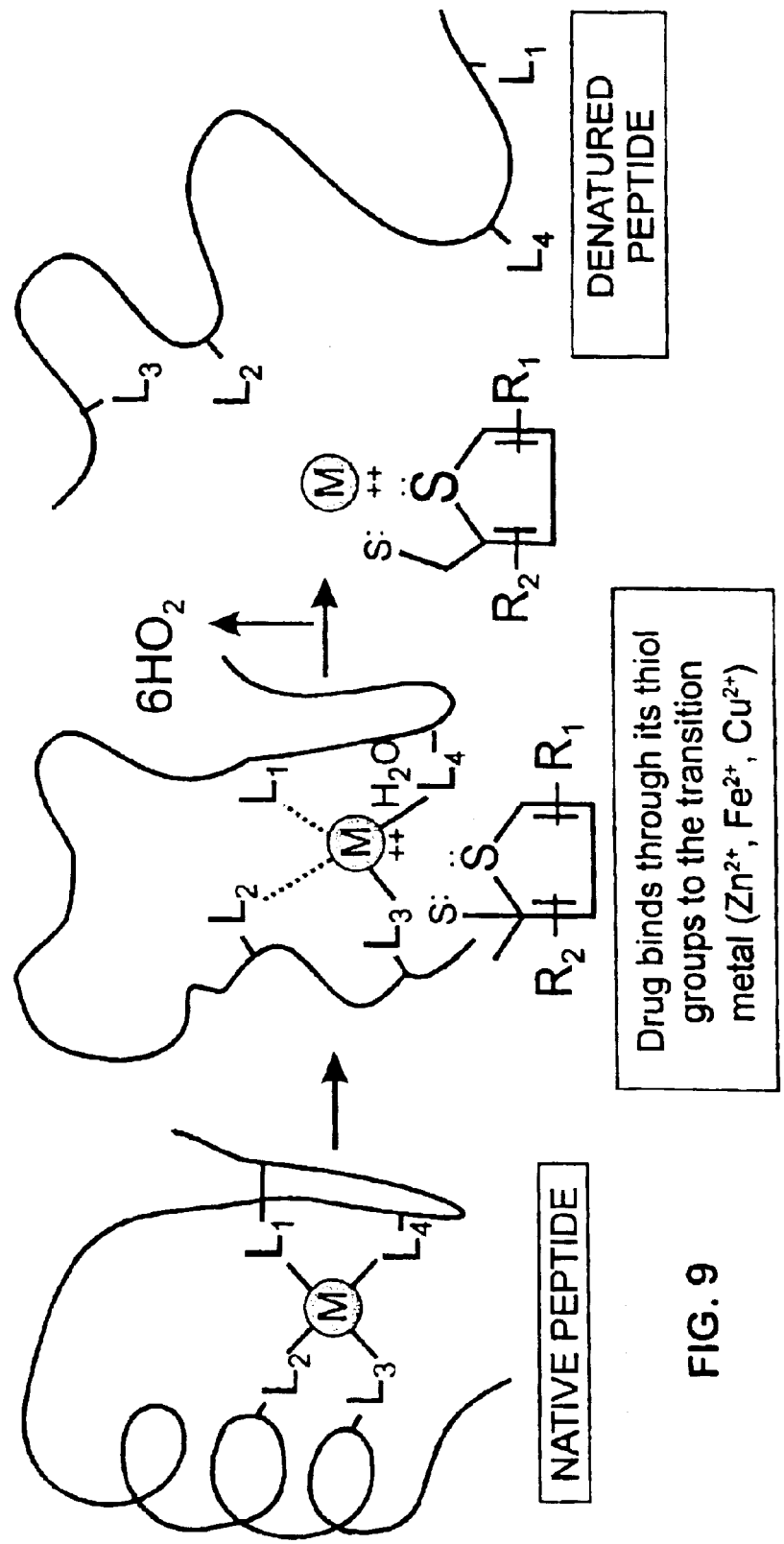
FIG. 9 is a conceptual folding scheme for a metal-binding peptide domain of a retroviral zinc finger protein and its disruption by the agents of this invention.

FIG. 1 summarizes the know chemistry of the 2-thiophenecarboxylic acid (2-TH) family of compounds. 2-TH and furoic acids can chelate divalent metal ions, including zinc, iron and copper. FIG. 9 shows that a retroviral zinc finger protein can be inactivated by 2-TH acid. The reagent attacks the zinc bound to the retroviral zinc finger protein (ZFP) and the reaction proceeds until the ZFP is unfolded and subsequently degraded by $Ca^{2+}$ dependent intracellular proteases, leading to apoptosis. The reaction releases zinc from the proteins and the zinc binds to the chelating agent.

As mentioned above, there are many families of viruses which are dependent upon metalloproteins having a zinc finger domain in their structure for replication of the virus. 2-TH acid, furoic acid or other suitable derivatives or analogs, can be administered orally to patients exposed to or suffering from viral diseases to bind the metal in the viral metalloprotein and thereby control the disease.

A pharmaceutically active and acceptable preparation of 2-TH acid or derivative in a concentration of approximately 1% to approximately 99%, preferably in a daily range of approximately 500 mg to 6000 mg, preferably approximately 500 mg to approximately 2000 mg of 2-TH acid can be used for this mode of treatment. It will be appreciated that doses approximating the LD-50 of 30 grams/70 Kg may be covered by the invention in the event continued research shows higher doses are optimal.

Novel substituted derivatives of 2-TH acid and related compounds can be used systemically to treat cancer, viral infections and other related diseases and proliferative disorders. The novel substituted derivatives of 2-TH acid and related compounds also work by disrupting the binding of zinc atoms in zinc finger proteins or metalloproteases or other structures heretofore unknown that depend upon the inclusion of zinc or other transition metal ions, for stability, packaging, or enzymatic activity. Further, the novel substituted derivatives are stable and retain their zinc chelating properties even when introduced systemically by injection, oral administration, inhalation or transdermal or other routes of administration FIGS. 1 and 2 illustrate novel derivatives of 2-TH acid for systemic use. Computer modeling indicates that such derivatives can interact with zinc atoms and disrupt its binding to the zinc finger protein or metalloproteases. Substitutions at positions 3, 4, and 5 on the 2-thiophenecarboxylic acid have the proper configuration to prevent interference with the zinc finger protein backbone. For example R3, R4, or R5 can be a methyl, ethyl, propyl, isopropyl, butyl, isobutyl, secondary butyl, tertiary butyl, pentyl, isopentyl, neopentyl or similar group. Further, substitution with halogens such as fluorine, chlorine, bromine and iodine can result in effective, systemically active agents. The systemic compounds can be prepared by methods generally known to the art and include pharmacologically acceptable salts thereof.

Figure 8:
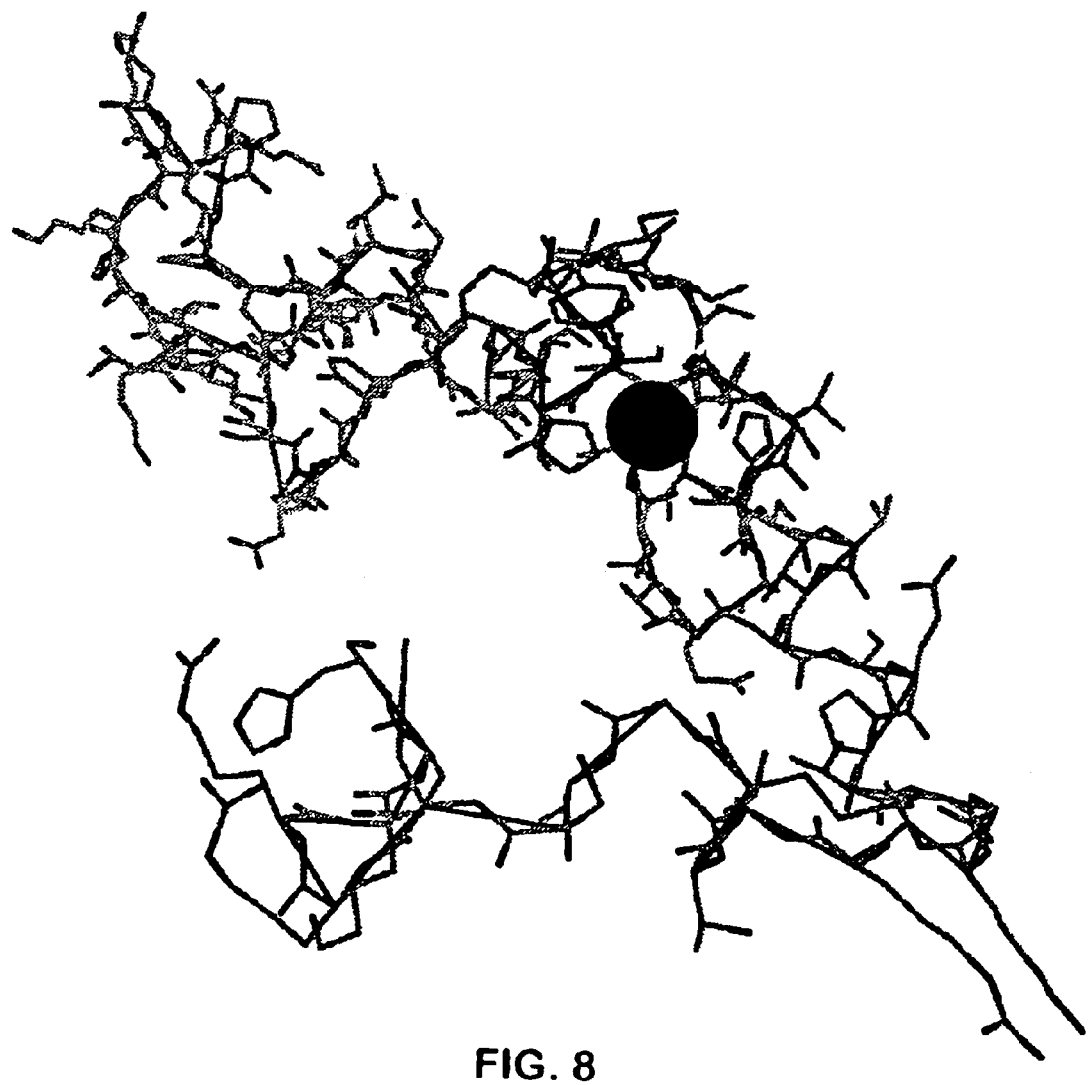
FIG. 8 illustrates a molecular model of a zinc finger protein denoted metallopanstimulin/S27 ribosomal protein with the zinc coordinately bound to four cysteine residues.
Figure 14:
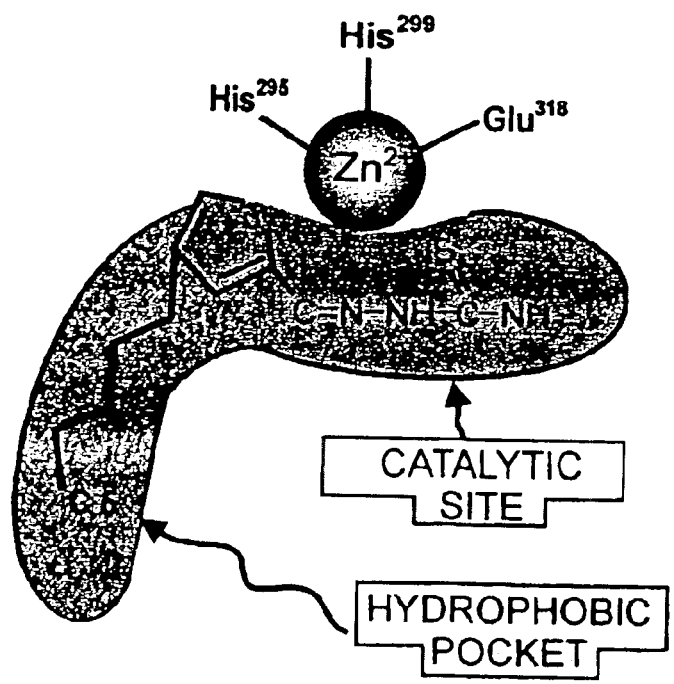
FIG. 14 illustrates the binding of 4-pentyl-2-thiophenecarboxylic acid thiosemicarbazone (4-P-2-TA-TSC) to the active site structure of human $LTA_4$ hydrolase. The zinc-binding ligands are His-295, His-299, and Glu-318. The shaded area indicates the L-shape hydrophobic cavity to which the 4-pentyl residue of 4-P-2-TA-TSC binds. The binding of the thiol group of 4-P-2-TA-TSC to the zinc atom at the active site of LTA4 hydrolase is also shown. 4-P-2-TA-TSC competes with the substrate for the active site of LTA4 hydrolase.

FIG. 8 illustrates the binding of zinc in a zinc finger protein denoted metallopanstimulin. Further, as shown in FIG. 14, the 4-pentyl-2-thiophenecarboxylic acid thiosemicarbazone (4-P-2-TA-TSC) can attach to both the catalytic zinc and the amino acids on a hydrophobic pocket of the enzyme LTA4 hydrolase forming a ternary complex comprised of the protein, the zinc, and the 4-P-2-TA-TSC acid derivative which inactivates the enzyme. Therefore, the above-listed moieties that can be substituted at various positions in the furan ring of 2-TH acid can result in a 2-TH acid derivative that not only is more stable for systemic administration, but also one that has even greater affinity and specificity for, and binding potential with, various zinc finger proteins or metalloproteinases.

It will be appreciated that substitutions at the 3, 4, and 5 positions can be made with an amino acid or a peptide of two to twenty-one amino acids or more with either basic or acid amino acids predominating. The substituted 2-TH acid would have an increased molecular weight and a substantially increased half-life in the blood. Further, such compounds would penetrate the cancer cells or virus-containing cells more effectively due to the amphipathic nature of the peptide residues.

The systemic compounds can be administered to human and animal subjects by any means that produces contact of the active agent with the target protein, such as orally, parenterally, inhalation, transdermally, rectally, on any other method for obtaining a pharmacologically acceptable blood level. In general, a pharmacologically effective daily does can be from about 0.01 mg/kg to about 25 mg/kg per day or any other pharmacologically acceptable dosing. A pharmaceutically active and acceptable preparation of 2-TH acid or derivative in a concentration of approximately 1% to approximately 99%, preferably in a daily range of approximately 250 mg to 6000 mg, preferably approximately 500 mg to approximately 2000 mg of 2-TH acid can be used for this mode of treatment. It will be appreciated that doses approximating the LD-50 of 30 grams/70 Kg may be covered by the invention in the event continued research shows higher doses are optimal.

It will be appreciated that in vivo administration of 2-TH acid or its derivatives for the treatment of cancer, for example, has unexpected results in animals, not predicted by the effect of furoic acid or 2-TH acid on cells in vitro, as described below in the examples. The inventors have determined that in vitro and in vivo, the compounds enhance the activity of macrophages.

The products, such as 2-TH acid, 4-butyl-2-TH-acid and derivatives, may be used to removed metals from a subject in disease states such lead poisoning or radioactive contaminations. Oral doses or injectable doses in the broad range of 250 mg to less than 30 grams per day may be used. Optimally, a dosage of 500 mg to 2000 mg per day would be used, with dosages up to 6000 mg or more in resistant cases.

The claimed invention is intended to include any other chemical compounds, either derivatives of 2-TH acid, compounds with structural relationships to 2-TH acid that function to chelate, attach to, or modify metal ions in proteins structures, including, but not limited to transition metal ions found in proteins structures of viruses, proliferative cells (plant or animal) or even as components of fungi and bacteria.

4. Therapeutic Applications

The breath and depth of the applications of the agents of this invention as enzyme inhibitors in biomedical applications is extensive. It is evident from the diversity of therapeutic application presented in this patent application that pathogenesis correlates with abnormal metalloprotein expression or abnormal metalloenzyme activity. The inhibition of metalloproteins or metalloenzymes can be a powerful and versatile tool in the treatment of seemingly unrelated diseases. Table 1 shows the potential extensive use of the agents of this invention.

There are a number of points addressed in this invention that allows the realization of the full potential of this agents as chelators or as metal complexes of the chelators. These factors, which are common to any therapeutic agent include: Specificity, biovailavility, compensatory effects in vivo, and stability. Specificity is a critical goal in the design of therapeutic applications of the compounds of this invention. Drugs generally exert some type of toxic effect and nonspecific events can lead to side effects. One of the attractions of targeting drugs to active sites of enzymes for their particular substrate is specificity. To determine selectivity tests of the compound against representative members of potential cross-reactive families of metalloenzymes should be done. The methods of this invention allow to create agents with truly demonstrated specificity and selectivity. For optimum effect, an inhibitor must be readily available at the target site. The inhibitor should reach the metalloprotein, anywhere in the cell. For example, if the enzyme is cytoplasmic, the inhibitor must cross the plasma membrane to reach the metalloenzyme. The characteristics of the side chains of the compounds of this invention allow high cellular penetrability. The same groups that allow cellular penetrability are the groups that specifically and selectively interact with the hydrophobic pockets surrounding the catalytically active metal site. Of course, in certain instances such as bacteria, fungus, and algae, this may require a delivery vehicle if the agent itself is non-membrane permeable. Although the agents of this invention are specific and efficient in inhibiting a single enzyme in vitro, it can be difficult to predict its ultimate effect in vivo. For example, a specific inhibition of an enzyme may result in unanticipated changes in enzymes of another pathway. It is unlikely that this will be the case in the therapeutic applications of our compounds because the proteins to be inhibited are the ones that are pathogenic and have to be antagonized to create a healthy state. Finally, the complexes of chelating agent/metal ion as a therapeutic combination must be exceptionally stable as chemotherapeutic agents in vivo and the metal should only be released at the target site.

Novel substituted derivatives of 2-TF acid and related compounds can be used systemically to treat cancer, viral infections, proliferative disorders, bacterial infections, parasitic diseases and other diseases that utilize metalloproteins as critical components of the pathogenic effect. The novel substituted derivatives of 2-TF acid and related compounds have a similar mechanism of action as the lead compounds. The mechanisms of enzyme inhibition and protein neutralization induced by this compounds relates to the high specificity of the agents to disrupt the binding of zinc atoms present in structural sites of metalloproteins or to inactivate the zinc containing catalytic site of metalloenzymes. As a consequence of disruption of the zinc ions or inhibition of its function by the specific chelating agent, the specific function of the protein is eliminated. For example, zinc ions required for protein stability, packaging of virus RNA, cellular replication, etc will be render ineffective. Moreover, the novel substituted derivatives are stable and thus, able to perform the specific functions when introduced systemically by injection, oral route, inhalation, rectally, or transdermally.

The invention will be described in additional detail by presenting specific examples. The following examples are described in detail for illustrative purposes only and they are not intended to limit the invention in any manner.

Examples of the specific effects of metal chelating agents, including 2-TH acid and substituted 2-TH acid derivatives thereof as well as the practical application of those agents will now be described:

Pharmacodynamics
Mechanism of Drug Action and the Relationship Between Drug Concentration and Effect In this section of this application we summarize the biochemical and physiological effects of the drugs and their mechanism of action. Moreover, the objective of this section is to characterize the pharmacodynamic differences between the chelating agents of this invention and other chelating agents previously used. Such analysis provides the basis for both the rational therapeutic use of the drugs of the instant invention and the design of the new and superior drugs based on the data present in this application.

The affinity of the drugs for its receptor and its intrinsic activity are determined by its chemical structure. The term receptor is operationally used to denote any zinc finger protein (ZFP) or metalloenzyme target to which the drug binds specifically to initiate its effects.

As it will be shown later, relatively minor changes in the drug molecule results in major beneficial changes in pharmacological properties. The drugs develop here have the following characteristics: 1) A more favorable ratio of therapeutic to toxic effects than other chelating agents; 2) enhanced selectivity among different cells as exemplify by the differential effects in normal versus cancer cells; 3) more cell penetrability than those of other chelating agents; and 4) they can be modified in a way in which they can be made specific and selective for the specific target metalloenzyme or target ZFP.

One of the basic differences between our drugs and other commonly used chelators is in the dose-response curves, a representation of the observed effect of a drug as a function of its concentration when it interacts with its specific receptor. The chemical affinity of our drugs for its receptor is in the appropriate range to modify the physiology of the specific target metalloenzymes or target ZFP receptor proteins. Thus, the drugs of this invention are specific and effective and have specific receptor-protein targets.

As shown by many examples in the literature (Fernandez-Pol, 2001), the shape of the curve for typical chelating agents such as carboxylic acids, its derivatives or EGTA, show a sharp dose-response relationship ($ID_{50}$ in the mM range) indicating very harsh effects on the cells, compatible with non-specific cytotoxicity to numerous metalloproteins. In contrast, the sigmoidal shape of the curves for the selected agents of this invention (FIG. 4), show that these agents have a wide concentration range ($ID_{50}$ in the nM to uM range), compatible with acceptable or no toxicity to normal cells. Thus, the different efficacies of the cellular stimulus-response for the various types of chelating agents previously utilized (Fernandez-Pol, 2001) compared with the novel chelating agents presented here show the superior nature of the agents of this invention.

The inventors have recognized the properties of 2-TH acid and derivatives as antiproliferative agents by in vitro studies with both normal and cancer cells. 2-TH acid, is a metal chelating compound that inhibits the growth of numerous cultured normal and transformed cells. It has been shown that 2-TH acid can arrest prokaryote and eukaryote cell growth by inhibition of zinc and iron requiring enzymes.

In contrast to its inhibitory activity in proliferating cells, 2-TH acid has a number of biological properties such as macrophage activation that can be exploited therapeutically as it will be demonstrated elsewhere in this application.

2-TH acid is a potent inhibitor of cancerous cell growth. 2-TA acid, a thiofuran derivative, metal ion chelator, shows an effect on the growth and viability of normal and cancerous cells in tissue culture. Examples presented here show that 2-TH acid and derivatives have potent anti-viral and anti-cancer activity in vitro. Moreover, 2-TH acid may be useful in the treatment of tumors in vivo without substantially damaging normal cells. Furthermore, it has been shown that 2-TH acid and derivatives can inhibit a panel of 60 different cancer cell lines in an NIH screening assay.

One critical property of the novel compounds of this invention derivatives of 2-TH acid is that the substitution at position 3 or 4 with a 1 to 15 carbon saturated fatty acid group increases cellular penetrability of this agent with respect to similar agents not having this lipid soluble residue. Inside the cells they works as specific TMA chelating agents. Another advantage is that inside the cell they can work at picomolar or nanomolar concentrations, depending upon the agent used. In general, the chelating agents currently available work intracellularly at mM concentrations (Ferandez-Pol, 2001).

The 4-butyl-2-TH acid is the 4-butyl derivative of 2-TH acid. Its structure is shown in FIG. 1. It is clear that 4-B-2-TH acid by the activity of the butyl group, or pentyl group as it will be shown later, penetrates the cell much more efficiently than 2-TH acid and depending upon the characteristics of its derivatives will attack multiple intracellular target metalloenzyme systems and target ZFPs.

While some of the less specific agents of this invention will attack simultaneously multiple cellular targets, other agents of this invention, will be highly specific and they will attack only one specific target metalloenzyme or target ZFP because of the characteristics of its molecular design and in particular the characteristics of their lipophilic side chains (FIG. 14).

Figure 7:
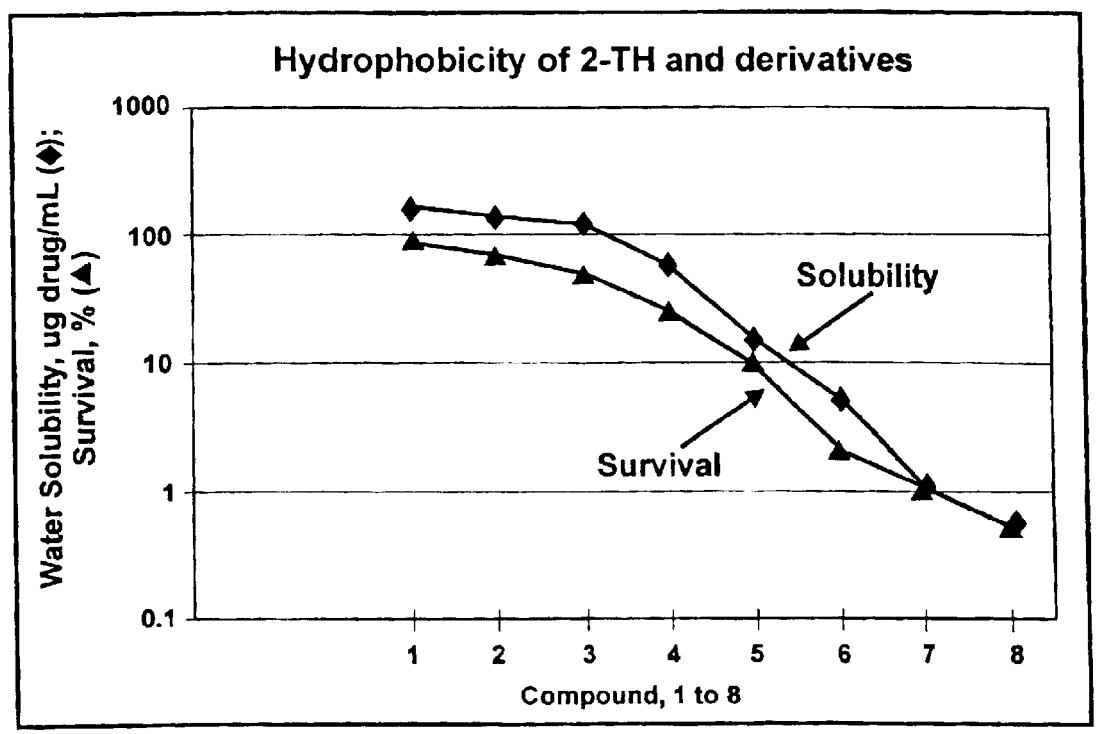
FIG. 7 illustrates the calculated relationship between water solubility and cytotoxicity of the novel agents. The higher the water solubility, the higher is the number of surviving cells. The chemical name of the agents is: (1) 2-thiophenecarboxylic acid; (2) 2-thiophenecarboxylic acid hydrazide; (3) 4-butyl-2-thiophenecarboxylic acid hydrazide; (4) 4-pentyl-2-thiophenecarboxylic acid hydrazide; (5) 4-hexyl-2-thiophenecarboxylic acid hydrazide; (6) 2-chloro-4-(trifluoromethyl) phenyl-2-furoic acid; (7) 4-nitro-2-thiophenecarboxylic acid hydrazide; (8) 4,5-diphenyl-2-thiophenecarboxylic acid hydrazide.

The three most cytotoxic and specific chelators of this invention have an ID50 value of 0.1 uM, and were derived from 2-TH acid. Thus, this invention defines the 2-position and the 4 position of 2-TH acid as structural components that confer anti-neoplastic activity. This is attributed to the high lipophilicity of the groups attached to position 4 and to the specific chelating capacity of the groups attached to the carboxyl in position 2. This relationship of lipothilicity to anti-proliferative effect was further documented by the observation that for a particular substitution at position 2 (e.g., hydrazide) the activity always increases as the lipophilicity of the parent compound increases (FIG. 7). Significantly, the addition of a halogen at position 3 and/or 5 increases the potency of the agent, possibly because of inhibition of biodegradation of the drug. Thus, in general, the specificity is conferred by both the lipophilic side chain and the chelating portion of the molecule, as demonstrated in several examples of this patent application.

EXAMPLE 1

Preparation of 4-butyl-3-5-Chloro-thiophenecarboxylic Acid Hydrazide

Many of the compounds described here are commercially available. Others have not been synthesized yet, although persons of ordinary skill in the art will know how to synthesize them. Thus, no attempt is made herein to describe the synthesis of such compounds. The present invention is directed to the structure of matter for compounds that have not been synthesize yet and to the use of both commercially available and new heretofore unrecognized compounds that dissociate and bind zinc (or other transition metal ion) from metalloproteins, which thereby inactivate the pathogenic protein and subsequently the pathogenic life form, whether a virus, bacteria, fungus, parasite, or cancer cells.

The chemistry and synthesis of one of the analogues of 2-TH acid that is of great interest for this invention can be described in exemplary form as shown in FIG. 2. This analogue denoted 4-butyl-3-chloro-2-thiophenecarboxylic acid hydrazide can be 7–10 times more active than 2-thiophenecarboxylic acid against cancer cells in tissue culture and against virally infected cells. Alternatively, the intermediary compounds shown in FIG. 2 can be derivatized to the 2-hydrazone, and 2-thiosemicarbazone by means that are well known in the art. Protection of specific groups in the thiophene ring for halogenation is well known in the art. See Protective Groups in Organic Chemistry, J. F. W. McOmie, Plenum Publishing Co., Ltd., 1973. Exemplary sources for the compounds that can be used as starting materials are as follows: Sigma-Aldrich, St Louis Mo., USA and Fluka Chemical Co, Germany.

Other compounds of particular importance for the subject invention, derived from the formulas defined immediately above and shown in FIG. 2, have the following formulas: 4-pentyl-3-5-dichloro-2-thiophenecarboxylic acid hydrazide, 4-pentyl-3-5-dichloro-2-thiophenecarboxylic acid hydrazone and 4-pentyl-3-5-dichloro-2-thiophenecarboxylic acid thiosemicarbazone, or derivatives thereof.

In addition, the present invention provides methods for screening the compounds delineated above which have the appropriate electron donor and chelating characteristics which will be suitable for pharmacological use.

EXAMPLE 2

Cellular Penetration of the Drugs Increases Cytotoxicity

The inventors have also recognized the importance of cellular penetrability for the therapeutic efficiency of these agents in special circumstances such as penetration in anthrax-infected macrophages and in infectious diseases of the brain. For that purpose, some of the compounds of this invention were designed with special hydrophobic qualities.

As shown in FIG. 7, cytotoxicity of eight novel molecules correlated significantly with low water solubility. The increase hydrophobicity results in faster cellular penetrability of the drugs which correlated with higher cytotoxicity. The molecules were more cytotoxic in the following order of increased hydrophobicity: (1) 2-thiophenecarboxylic acid; (2) 2-thiophenecarboxylic acid hydrazide; (3) 4-butyl-2-thiophenecarboxylic acid hydrazide; (4) 4-pentyl-2-thiophenecarboxylic acid hydrazide; (5) 4-hexyl-2-thiophenecarboxylic acid hydrazide; (6) 2-chloro-4 (trifluoromethyl) phenyl-2-furoic acid; (7) 4-nitro-2-thiophenecarboxylic acid hydrazide; and (8) 4,5-diphenyl-2-thiophenecarboxylic acid hydrazide.

Hydrophobicity may play a role in two cellular mechanisms of drug activity: cellular penetration and access to specific subcellular compartments. Therefore, better diffusion past the cellular membrane may explain the higher toxicity of the more lipid soluble molecules. The data confirms that increased hydrophobicity increases cytotoxicity as demonstrated by the fact that the higher the water solubility, the higher is the number of surviving cells.

In addition to the selection of compounds with high cellular penetrability, methods for identifying compounds that have crossed the lipid barrier and can react with intracellular metalloproteins have been developed in the last 20 years. These methods can be used to screen and identify compounds based on their ability to react with peptide sequences selected from pathogenic metalloproteins. The reactions can be carried out in an aqueous or lipophilic environment, dependent upon the solubility characteristics of the peptide and the drug being tested. The methods of detecting the dissociation of the transition metal ion (TMI) ion or formation of ternary complexes (compound-TMI-protein) include immuno-blotting, Nuclear Magnetic Resonance (NMR), high pressure liquid chromatography (HPLC), detecting the release of radioactive TMI such as radioactive $Zn^{2+}$, $Cu^{2+}$ or $Fe^{2+}$, detecting changes in protein mobility in gel shift assays, and capillary electrophoresis. Finally, assays to study the inhibition of binding of metalloproteins or metallopeptides to DNA or RNA by the chelating agents under study can be use to screen and identify the compounds.

EXAMPLE 3

Molecular Structure of Systemic Compounds

Novel substituted derivatives of 2-thiophenecarboxylic (2-TH) acid and related compounds can be used systemically to treat viral diseases, infections, cancer and other disorders as shown in Table 1. The novel substituted derivatives of 2-TH acid and related compounds also work by disrupting the binding of zinc atoms to zinc finger proteins or by inactivating zinc in metalloenzymes, or other structures heretofore unknown that depend upon the inclusion of zinc or other transition metal ion (T), for stability, packaging or replication. Further, the novel substituted derivatives are stable and retain their TM chelating properties even when introduced systemically by injection, oral administration, inhalation or transdermal or other routes of administration FIG. 1 illustrates some of the novel derivatives of 2-TH acid for systemic use. Computer modeling demonstrates that derivatives of 2-TH acid can interact with zinc atoms and disrupt its binding to the target metalloprotein. Substitutions at positions 3,4 and 5 on the 2-TH acid have the proper configuration to prevent interference with the zinc finger protein backbone. For example R1 or R2 can be a methyl, ethyl, propyl, isopropyl, butyl, isobutyl, secondary butyl, tertiary butyl, pentyl, isopentyl, neopentyl or other hydrophobic or polar group. Further, substitutions with halogens such as chlorine, bromine, iodine and fluorine can result in highly stable and effective systemically active agents. The systemic compounds can be prepared by methods well known in the art and include pharmacologically acceptable salts thereof.

FIG. 9 illustrates the binding of zinc in a zinc finger protein and its disruption by the agents of this invention. Further, as shown in FIG. 14, the substitution at position 4 (R2) of the thiophene ring with a pentyl group can attach to amino acids on a hydrophobic pocket of the metalloenzyme, thus binding simultaneously to the zinc and the hydrophobic pocket, forming a ternary complex comprised of the protein, the zinc and the 2-TH acid derivative which inactivates the metalloenzyme. Therefore, the above-listed moieties that can be substituted at various positions in the thiophene ring can result in a 2-TH acid derivative that not only is more stable for systemic administration, but also has even greater affinity, specificity, and selectivity for and binding potential with specific metalloproteins or metalloenzymes.

It will be appreciated that substitution at the 3, 4 and 5 positions can be made with single amino acids or peptides of 2 to 21 amino acids containing either basic or acid amino acids in different proportions. The substituted 2-TF acid will have an increased molecular weight and a substantially increased half-life in the blood. Further, the amphipathic nature of the peptide residues would allow a more effective penetration in abnormal cells, viruses, bacteria, parasites and other microorganism.

The systemic compounds can be administered to animal and human subjects orally, parenterally, inhalation, transdermally, rectally, or other pharmaceutically acceptable method of obtaining therapeutic levels in the blood. In general, a pharmacologically effective daily dose of these derivatives could range from 0.01 mg/kg body weight to about 30 mg/kg body weight per day. A pharmaceutically active preparation of 2-TH acid or derivative in a concentration of 1% to 99% in a daily range of 10 to 10000 mg, can be used for the treatment of various diseases described in the specific examples. It will be appreciated that 2-TH acid and derivatives can be employed in topical preparations, in addition to the systemic uses.

WIDE-SPECTRUM ANTIVIRAL ACTIVITY OF 2-THIOPHENECARBOXYLIC ACID AND DERIVATIVES

The chelating agents of the present invention can also be used to control viral diseases. It has been documented that zinc and iron are required transition metals in certain proteins and enzymes essential for viral structure or function. For example, the replication of certain viruses such as the Hepatitis C virus is dependent on zinc metalloproteinases. Propagation of the AIDS virus is dependent on Zn2+ requiring proteins such as the p7 zinc finger nucleocapsid protein. The administration of specific chelating agents of the instant invention can prevent unwanted formation of viral metalloproteins and metalloenzymes. The 2-TH acid derivatives can be highly efficient by targeting specific amino acid regions of the zinc finger or other metalloproteins or metalloenzymes of viruses. These chemical entities that function in the same manner as 2-TF acid and derivatives are intended to be encompassed by the instant invention. The chelating agent can be administered orally or parenterally in doses described elsewhere in this application Representative viruses with metalloproteins that can be targeted with the agents of this invention are shown in Table 2.

TABLE 2

Examples Of Families Of Viruses Using Zinc Finger Proteins Or Transition Metal Ion-Dependent Enzymes For Replication And/Or Virulence that can be targeted with the agents of this invention

| Families, Virus protein and Mr | Location and general Characteristics | Protein Function and Specific Properties |
|---|---|---|
| Reoviridae | | |
| Lambda-1, 140 Kd | Inner capsid | Zinc finger protein Binds dsDNA |
| Rho-3, 41 Kd | Outer capsid | Zinc finger protein Binds dsRNA |
| Rotaviridae | | |
| NSP1, 53 Kd | Non-structural | Zinc finger protein RNA binding |
| Retroviridae | | |
| np7 (AIDS) 55 amino acids | Nucleocapsid | Two Zinc finger domains RNA binding Required for inclusion of RNA in virions |

TABLE 2-continued

Examples Of Families Of Viruses Using Zinc Finger Proteins Or Transition Metal Ion-Dependent Enzymes For Replication And/Or Virulence that can be targeted with the agents of this invention

| Families, Virus protein and Mr | Location and general Characteristics | Protein Function and Specific Properties |
|---|---|---|
| Arenaviridae | | |
| MPS-1; 84 amino acids | Regulatory protein | One zinc finger domain |
| Papillomavirinae | | |
| E6 | Regulatory protein | Zinc finger protein Transforming protein of HPVs Continuous cell proliferation Targets degradation of p53 |
| E7 | Regulatory protein | Zinc finger protein Transforming protein of HPVs Continuous cell proliferation Binds to the retinoblastoma protein, Rb |
| Poxviridae | | |
| Ribonucletide Reductase | Fe-dependent Enzyme | Synthesis of DNA Precursors |
| Flaviviridae (Hepatitis C) | | |
| NS2(+NS3) | Zn-dependent enzyme | Zn-metalloproteinase |
| Herpesviridae | | |
| HSV-1: ICPO protein | Regulatory protein | Zinc finger DNA-binding Trans-activation |
| HSV-2: MDBP protein | Regulatory protein | Zinc finger protein ssDNA-binding DNA replication |
| ICP6: Ribonucleotide Reductase | Fe-dependent Enzyme | Synthesis of DNA precursors |
| Orthomyxoviridae | | |
| Influenza viruses M1 protein | Structural protein | One zinc-finger domain |

EXAMPLE 1

2-thiophenecarboxylic (2-TH Acid Inhibits the Zinc Dependent Binding of Recombinant MPS-1/S27 Ribosomal Protein to DNA or RNA MPS-1/S27 is a ribosomal protein involved in ribotoxic responses to cellular damage, carcinogenesis and responses to viral infection (Fernandez-Pol, 2001). It is also induced as a biological response to bacteria, fungus and parasites. In parasites such as Toxoplasma gondii the parasitic encoded form of MPS-1/S27 is highly elevated and active during all the parasitic replication cycle. It is also active in macrophages digesting cells such as those found in melanomas (Fernandez-Pol, 2001). MPS-1/S27 is also involved in biological response modulation by the chelating agents agents of this invention.

MPS-1 is described in detail in one of the inventor's U.S. Pat. No. Re. 35,585 (U.S. Pat. No. 5,343,041). MPS-1 has one zinc finger domain of the type CCCC (FIG. 8). By molecular modeling, the inventors have determined that 2-TH acid and derivatives interact with the zinc bound to the CCCC domain and removed Zn2+ from MPS-1. These data indicate that 2-TH acid and derivatives should remove zinc and disrupt, denature or inhibit various types of zinc finger proteins or metalloenzymes, whether known or heretofore undiscovered, including viral proteins such as nucleocapsid p7 proteins, as will be explained in the next example.

EXAMPLE 2

Identification of HIV-1 Nucleocapsid Protein p7 as a Target for 2-TH Acid and Derivatives Research on the structure and function of ZFP, performed by numerous investigators have identified the critical role that ZFP play in the uncontrolled proliferation of virally, chemically, and radiation transformed cells in culture. ZFP are essential for DNA/RNA replication By inhibiting ZFP in transformed cells, the uncontrolled proliferation of these cells is blocked. In addition, ZFP are required for packaging of viral genetic material into new virions (Fernandez-Pol, 2001).

The p7 protein of the HIV-1 virus contains two zinc fingers that are essential for the recognition and packaging of viral RNA. Several investigators have characterized the high affinity binding of HIV-1 nucleocapsid protein (p7) to the HIV 5'LTR of viral RNA. The results showed that p7 protein binds with high affinity (Kd's in the low nanomolar range) to short repeats of dTG's in RNA. Thus, drugs that prevent the interaction of p7 protein with nuclei acids are of great therapeutic interest.

As described above, it has been found that the p7 protein of the HIV-1 virus is required for correct assembly of newly formed virus particles during the viral life cycle. In one embodiment of the invention, the inventors have targeted p7 for drug therapy with 2-TH acid and derivatives. Utilizing computer models, the inventors have discovered the activity of 2-TH acid and it derivatives in disrupting zinc finger nucleoproteins of retroviruses. FIG. 9 illustrates the effects of 2-TH acid and derivatives on one of the zinc fingers of a retroviral protein such as the p7 protein. Furthermore, FIG. 9 illustrates that the disruption of one of the zinc finger binding domain in retroviral proteins caused by 2-TF acid and derivatives results in the ejection of Zn2+ and subsequent denaturing of the protein. Derivatives of 2-TF acid are zinc finger disrupting agents that act by specifically attacking one or both of the two zinc finger domains of the retrovirus nucleocapsid p7 protein.

Computer simulation has also shown that 2-TH acid and derivatives induce an overall decrease in the number of complete viral particles that bud off and exit the cells to infect other cells. The HIV-1 and HIV-2 zinc finger p7 proteins are highly conserved in the zinc finger domains. It has been determined that the zinc finger domains are highly conserved in the majority of retroviruses. Furthermore, mutations in the zinc fingers of the HIV-1 virus p7 protein produce a non-infectious HIV-1 viral particle. It has been determined that the zinc finger domains of HIV viruses are essential for nucleic acid binding. Thus, p7 resistant mutants are unlikely to occur. Therefore, the 2-TF acid and derivatives can be used for prevention of retroviral diseases by chemically inducing a non-infectious viral particle and/or preventing the exit of a complete infectious virus from the cells.

EXAMPLE 3

Inhibition of Herpes Virus Ribonucleotide Reductase (RR) by Furoic Acid and 2-TH Acid and Derivatives The antivirals of this invention such as furoic acid and 2-TH acid and derivatives can have a significant impact on the management of herpes virus infections. The use of agents such as acyclovir, ganciclovir and foscarnet have resulted in an increase emergence of drug-resistant herpes virus strains. The use of the new classes of anti-herpes virus compounds of this invention with novel mechanisms of viral inhibition is important to prevent the emergence of viral mutants. Furoic acid, 2-TH acid and derivatives can simultaneously inhibit Herpes virus RR, an iron requiring enzyme, and viral zinc finger proteins, thus reducing the possibility of emergence of Herpes virus mutant strains. A pharmaceutically acceptable concentration of furoic acid, 2-TH acid or a derivative in a concentration of 1% to 99% could be administered in a daily range of 100 to 5000 mg to inhibit replication of herpes viruses. Of course, these preparations can be combined with other anti-viral agents with different mechanisms of action to increase therapeutic efficiency.

EXAMPLE 4

Inhibition of Papilloma Virus Replication by the Action of 2-Thiophenecarboxylic Acids Only two viral ZFP of HPV are consistently expressed and integrated in keratinocytes, the E6 and E7 zinc finger proteins. They are responsible for continuous cell proliferation. The E6 and E7 proteins regulate cell proliferation by interfering with p53 and pRb, respectively. The cell cycle is altered at the G1/S interphase. Thus, one should be able to eliminate HPVs by using 2-TH acid and derivatives because the E6 and E7 HPV proteins are critical zinc finger proteins required for viral replication. When replication of virus is arrested, apoptosis of virally-infected cells must occur. Thus, one may be able to alter the epidemiology of carcinoma of the uterine cervix by using 2-TH acid or derivatives as chemopreventive agents.

2-TH acid and analogues act by chelating metal ions. In the case of inhibition of viral replication by 2-TH acid, the ion involved is zinc, which is essential to maintain the active structure of zinc finger proteins such as E6 and E7 proteins of the human papilloma viruses which are essential for viral replication.

Since HPV induces cell proliferation, the mechanism of action of 2-TH acid may also be cellular, as that described for other virally transformed cells. One possibility is that inhibition of growth by 2-TH acid in HPV transformed cells can be explained by an effect on cellular RNA polymerase, a known metalloenzyme. It can also inhibit ribosomal protein synthesis, since many ribosomal proteins are zinc finger proteins (Fernandez-Pol, 2001). Thus, 2-TH acid and derivatives may act on numerous target sites such as viral, nuclear or cytoplasmic metalloproteins. Furthermore, 2-TH acid and derivatives can act as biological response modifiers, suggesting that when 2-TH acid and derivatives distorts the configuration of HPV zinc finger proteins, they may become immunogenic when new antigenic sites are exposed. Thus, the agents of this invention can be used to stimulate a cellular immune response against viruses, primary tumors and parasites.

EXAMPLE 5

Inhibition of Zinc Dependent Metalloproteinases of Hepatitis C Virus by 2-TH Acid and Derivatives The hepatitis C family of viruses are dependent upon zinc metalloproteinases such as the NS2(+NS3) for replication of the virus (Table 2). 2-TH acid or suitable analogs, can be administered orally or parenterally to patients exposed or infected with Hepatitis C virus. This specific agents will bind the metal in the zinc dependent metalloproteinase rendering it inactive and thereby controlling the disease. Furthermore, the oral administration of the specific metal chelator in combination with other anti-viral agents may result in the elimination of the virus from the cells. A pharmaceutically acceptable concentration of 2-TH acid or a derivative in a concentration of 1% to 99% could be administered in a daily range of 100 mg to 5000 mg for this antiviral treatment.

EXAMPLE 6

Inhibition of the AIDS Virus by a Metallo-Organic Complexes of 2-thiophenecarboxylic Acid and Derivatives The active site of the HIV-1 protease contains a catalytic water molecule between the two catalytic residues Asp25 and Asp125. Using data bases and molecular modeling we observed that metallo-organic complexes can be form by using Cu (II)-2-TH acid and derivatives which fit into the active site of the enzyme. We calculated that this competitive inhibitor of the viral protease can work at the uM range. Furthermore, by adding a carboxyl in position 5 of the thiophene ring a bidentate cooper (II) chelator can be created. The bidentate copper (II) chelators can dock into the active site of the viral protease and inhibit its activity at the low uM range (5 to 0.1 uM).

EXAMPLE 7

The Microglia-associated HIV Virus in Neurological Diseases can be Inhibited by 4-butyl-2-thiophenecarboxylic Acid Hydrazide HIV-1 is a neurotropic virus. The overwhelming majority of cells infected with HIV-1 in the central nervous system are microglia/macrophages. Microglia/macrophage infection leads to immune deficiency as well as the production and release of cytotoxic molecules such as cytokines which contributes to the progression of the disease. Due to the capacity of the agents of this invention to cross the blood brain barrier, to penetrate and activate macrophages/microglia, and to disrupt HIV-1 viral zinc finger proteins, these agents can be used to treat this neurological viral condition.

EXAMPLE 8

Treatment of Chickenpox

Treatment of chickenpox can be accomplished by topical treatment with furoic acid or 2-TH acid when the rash is in the early stages. A 5% to 10% solution of the antiviral compound can be applied to the lesions of a patient with chickenpox. Since herpes virus replication will be inhibited, it is expected that the lesions will not erupt into blisters and that the treated areas will not itch.

EXAMPLE 9

Treatment of Smallpox and Biological Warfare

The poxviruses are a family of large, enveloped DNA viruses. The most notorious poxvirus is variola, the causative agent of smallpox. Smallpox was important because of the morbidity and mortality cause by this virus. Despite the eradication of naturally occurring smallpox and the availability of a vaccine, the potential for weaponization of variola virus continues to present a universal threat. The aerosol infectivity of the virus, the ease of large-scale production, and a naive human population remarks the importance of smallpox virus as a weapon. Vaccinia vaccination remains the preeminent countermeasure for smallpox but its application and development of immunity is slow and thus it is not appropriate to counteract bioterrorism in all its forms. The drug N-methylisatin-p-thiosemicarbazone (Methisazone) possess some efficacy in post-exposure prophylaxis but is shows significant toxicity. An opportunity exist to correct and counteract this situation by developing new, effective, low toxicity wide-spectrum antiviral agents. This invention contributes new wide-spectrum anti-viral agents suitable for the purposes of prophylaxis and treatment of smallpox infections.

A large number of virus-encoded enzymes and factors are packaged in the smallpox virus particle. The RNA polymerase (a zinc requiring enzyme); the superoxide dismutase (a Cu/Mn/Zn requiring enzyme); and ribonucleotide reductase (an $Fe^{2+}$ requiring enzyme which is inhibited by hydroxyurea), as well as viral and cellular zinc finger proteins such as MPS-1/S27 ribosomal proteins are involved in critical early functions of the smallpox virus. Thus, the smallpox virus is dependent upon viral and cellular metalloproteins and metalloenzymes for replication of the virus.

2-Thiophenecarboxylic (2-TH) acid hydrazide, hydrazone, thiosemicarbazone, or suitable analogs, can be administered orally or parenterally to patients exposed or infected with smallpox virus. These specific agents will bind the metal in the metalloenzyme and/or metalloprotein rendering it inactive and thereby controlling the disease. Furthermore, the oral administration of the specific metal chelator in combination with other anti-viral agents such as Methisazone may result in the elimination of the virus from the cells. A pharmaceutically acceptable concentration of 2-TH acid or a derivative in a concentration of 1% to 99% could be administered in a daily range of 100 mg to 5000 mg for this antiviral treatment.

Cancer and Metastatic Disease

2-Thiophenecarboxylic Acid and Derivatives are Potent Inhibitors of Cancerous Cell Growth The chelating agents of the present invention can also be used to control cancer and metastatic disease. The administration of the specific chelating agents of the instant invention can be used as effective chemotherapeutic agents. The chelating agent can be administered orally or parenterally in doses described elsewhere in this application 2-thiophenecarboxylic (2–111) acid, is a metal chelating compound, which inhibits the growth of numerous cultured normal and transformed mammalian cells. It also is shown that 2-TH acid can arrest prokaryote and eukaryote cell growth by inhibiting Zn and Fe-requiring enzymes. In addition to its chelating ability, 2-TH acid has a number of biologic properties such as macrophage activation.

2-TH acid is a potent inhibitor of cancerous cell growth. 2-TH acid, a thiofuran derivative, metal ion chelator, shows an effect on the growth and viability of normal and cancerous cells in tissue culture. Examples presented here show that 2-TH acid has potent anti-cancer activity in vitro. Moreover, 2-TH acid and derivatives can be useful in the treatment of tumors in vivo without substantially damaging living normal cells.

4-butyl-2-Thiophenecarboxylic acid hydrazide (4-B-2TAH) is a derivative of 2-TCA. Its structure is shown in FIG. 1. 4-B-2TAH was recognized to have potent anticancer activity in vitro. The properties of 4-B-2TAH can be summarized as follows: Undoubtedly the drug interacts with various zinc finger proteins and transition metal ion-requiring enzyme systems. 4-B-2-TAH is noted to be an inhibitor of a wide variety of seemingly unrelated enzyme systems. These include Zn-finger proteins and Zn-dependent metalloenzymes. Fe- and Cu-requiring enzyme systems are also effected by 4-B-2-TAH. These enzymatic systems are important in growth control mechanisms. It is clear that 4-B-TAH, by virtue of its butyl group penetrates the cell interior much more easily than 2-TH acid, and works as a Zn/Cu/Fe chelating agent.

Important, 2-TH acid and analogues, in particular the 4-butyl-2-thiophenecarboxylic acid hydrazide (or hydrazone, or thiosemicarbazone) possess in vitro anti-tumor activity that is much greater and specific than currently available chelators. Furthermore, some of the compounds of this invention can act intracellularly at picomolar concentration in transition metal ion containing enzymes, such as zinc-dependent metalloproteinases. Thus, the agents presented in this invention can penetrate cells, reached the Zn-metalloprotein which is present at low intracellular concentrations (uM) and inactivate it.

From our studies with 2-TH acid analogues, we have identified the moieties shown in FIG. 1 and FIG. 2, as structural components which infer anti-neoplastic activity. The result indicate that the anti-proliferative activity of 2-TH acid and derivatives is due to their ability to form a metal ion complex.

Figure 4:
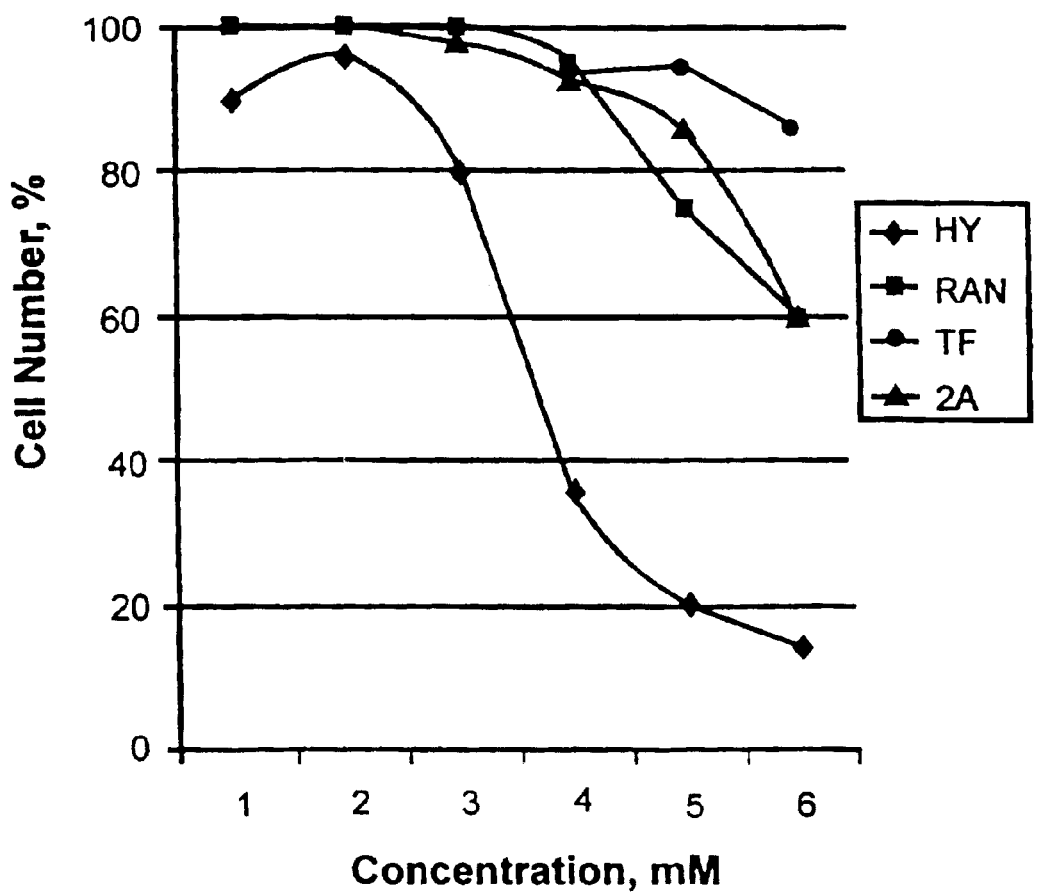
FIG. 4 illustrates the effects of different concentrations of 2-thiophenecarboxylic acid hydrazide (HY) on the growth of CHO cells; other compounds tested were: Furan (RAN); thiophene (TF), and furoic acid (FA)

It will be also appreciated that by understanding the structure-activity relationships of these ligands, the compounds of the instant invention can be made target specific and have dose-response relationships for systemic use that are sigmoidal and thus they have a wide range of therapeutic concentrations (FIG. 1, FIG. 4, FIG. 14).

Examples of the specific effects of metal chelating agents, including furoic acid, and 2-thiophenecarboxylic acid and derivatives, as well as the practical applications of these agents in medicine will now be described:

EXAMPLE 1

Effects of 2-Furoic Acid on Growth of CHO Cancer Cells

Cells were plated at $1.5 \times 10^5$ cells/60-mm dish; 24 hours later, the medium was removed, and new media with or without 0.05 to 10 mM final concentrations of 2-Furoic acid were added. Cell counts were determined at 24, 48 and 72 h after the addition of 2-Furoic acid; each point is the average of triplicate measurements from 3 cultures. Furan, an analog of 2-Furoic acid, was simultaneously tested at 0.05 to 10 mM under identical culture conditions (FIG. 4).

The results show that the growth of CHO cells was inhibited in a dose-dependent fashion by 3 to 10 mM 2-Furoic acid within 24 hours. The cells showed no significant toxic effects for up to 72 hours after treatment. At 72 h the growth inhibition induced by 3 and 10 mM 2-Furoic acid were about 20% and 40%, respectively. Furan, a structurally related substance had a similar dose-dependent effect on cell growth inhibition at 24, 48 and 72 h (FIG. 4).

EXAMPLE 2

Effects of 2-thiophenecarboxylic Acid Hydrazide on Growth of CHO Cancer Cells

Cells were plated at $1.5 \times 10^5$ cells/60-mm dish; 24 hours later, the medium was removed, and new media with or without 0.05 to 10 mM concentrations of 2-thiophenecarboxylic acid hydrazide (2-TCAH) were added to the media Cell counts were determined at 24, 48 and 72 h after the addition of 2-TCAH; each point is the average of triplicate measurements from 3 cultures. Thiophene (Thiofuran), an analog of 2-TCAH, was simultaneously tested at 0.05 to 10 mM under identical culture conditions (FIG. 4).

Figure 6A:
FIG. 6A illustrates the effects 2-thiophenecarboxylic acid on morphology of CHO cells.
Figure 6B:
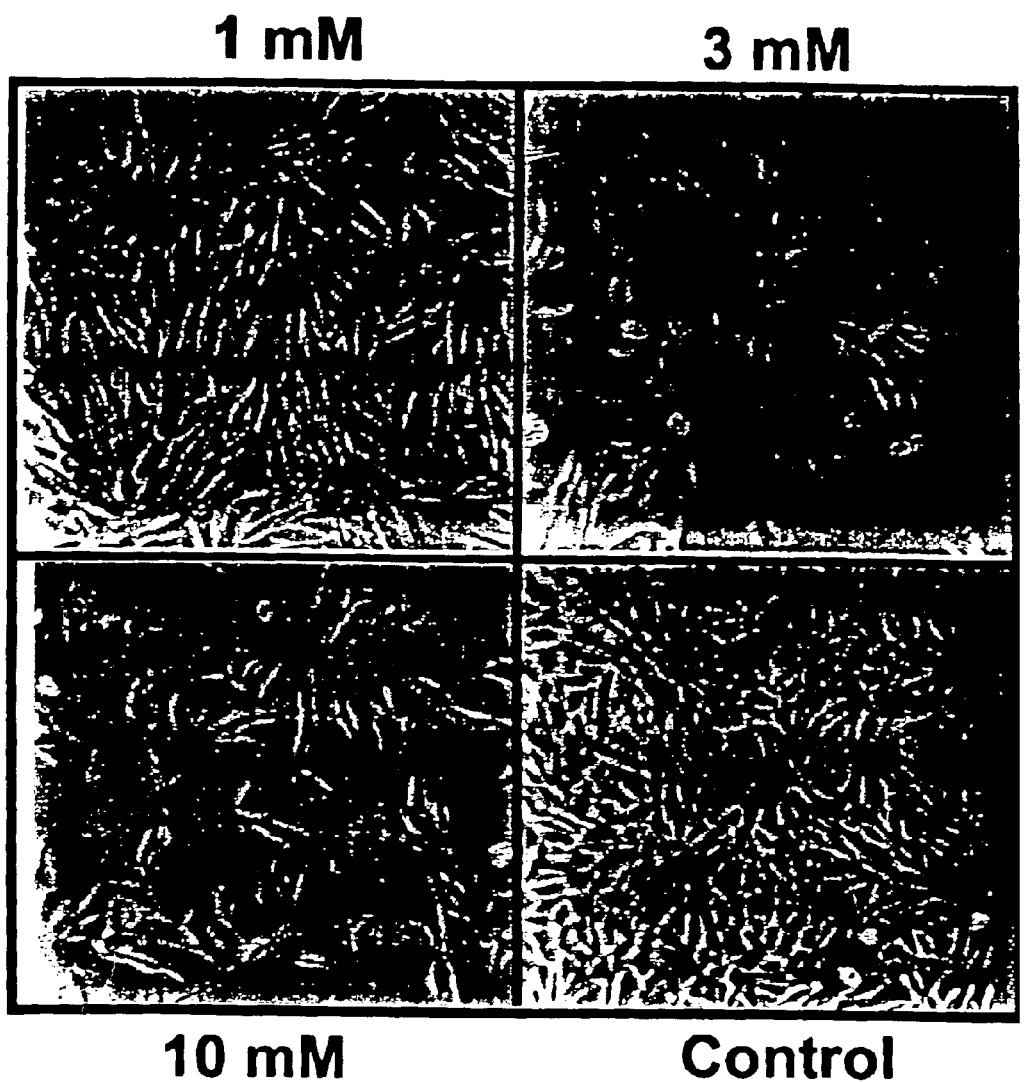
FIG. 6B illustrates the effects of 2-thiophenecarboxylic acid hydrazide on morphology of CHO cells.

The results show that the growth of CHO cells was inhibited in a dose-dependent fashion by 1 to 10 nM 2-TCAH within 24 hours. The cells showed significant toxic effects at 48 to 72 hours after treatment (FIG. 6B). At 72 h the inhibition induced by 1 and 10 mM 2-TCAH were about 65% and 90%, respectively. Thiophene, a structurally related substance had no significant effect on cell growth at 72 h (FIG. 4).

EXAMPLE 3

Effects of 3,4,5-Trichloro-2-Furoic Acid on the Growth of Cancer CHO Cells

Cells were plated at $1.5 \times 10^5$ cells/60-mm dish; 24 hours later, the medium was removed, and new media with or without 0.1, 1 and 3 mM final concentrations of 3,4,5-Trichloro-2-Furoic acid (3,4,5-TFA) were added. Cell counts were determined at 24, 48 and 72 h after the addition of 3,4,5-TFA; each point is the average of triplicate measurements from 3 cultures.

Figure 5:
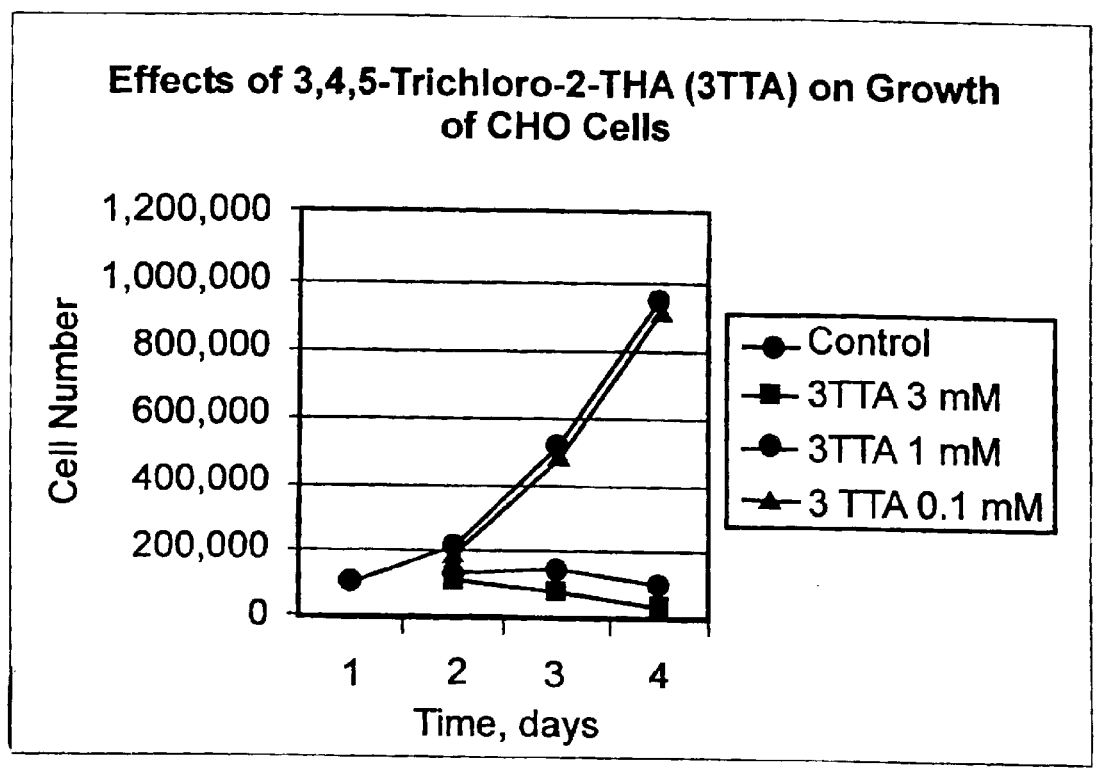
FIG. 5 illustrates the effects of different concentrations of 3,4,5-trichloro-2-thiophenecarboxylic acid on the growth of CHO cells.
Figure 6C:
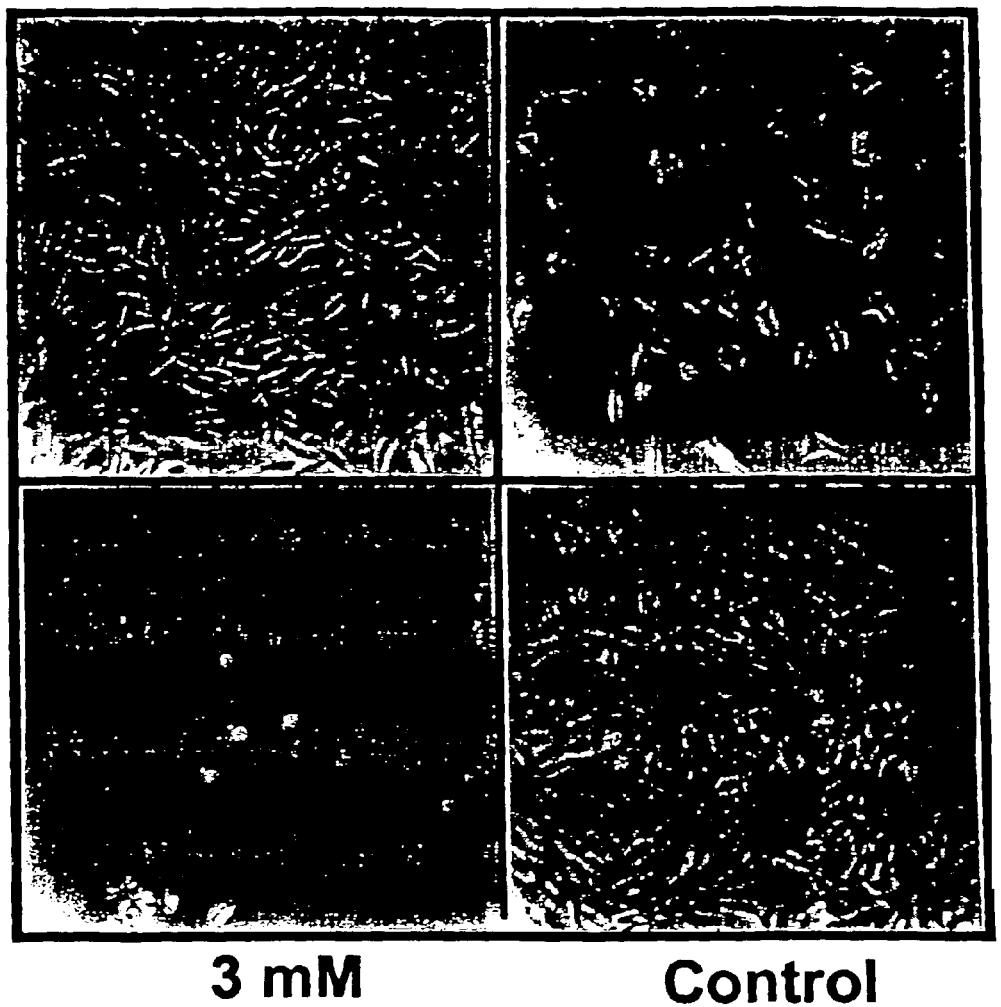
FIG. 6C illustrates the effects of 3,4,5-trichloro-2-thiophenecarboxylic acid acid on morphology of CHO cells.
Figure 6D:
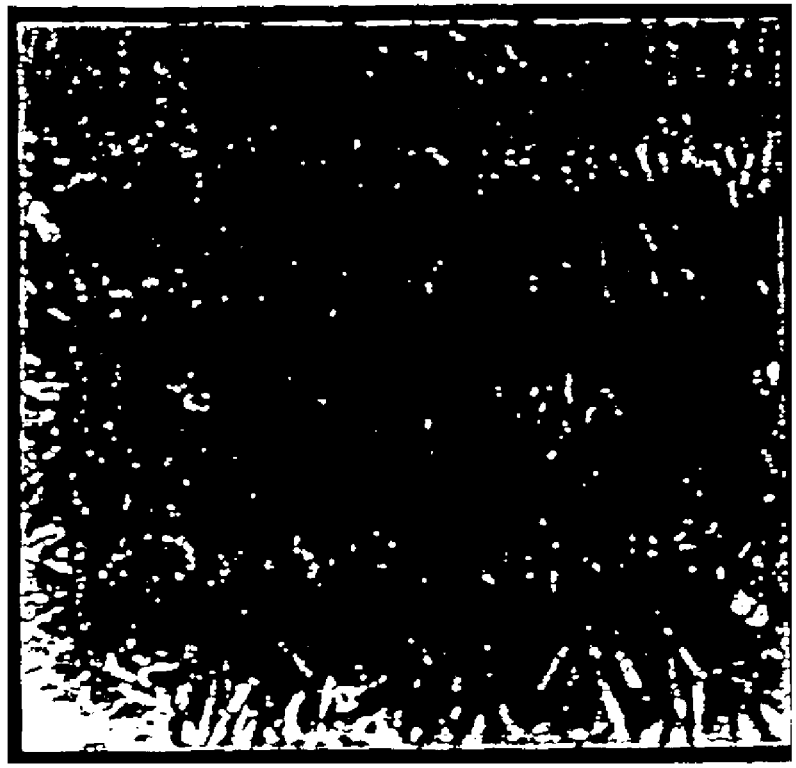
FIG. 6D illustrates the morphology of CHO cells growing in a control culture without drug additions.

The results show that the growth of CHO cells was strongly inhibited by 1 mM and 3 mM 3,4,5-TFA within 12 h of addition of the substance (FIG. 5; FIG. 6C). At 24 h, 48 h and 72 h the growth inhibition induced by 1 and 3 mM 3,4,5-TFA was greater than 80% and 99%, respectively (FIG. 5; FIG. 6C).

After 12 to 48 hours of exposure to 1 and 3 mM 3,4,5-TFA, CHO cells acquired a flattened morphology, they began to look granular, no mitosis were observed, and some began to float in the medium. With longer exposure (48–72 hours) cytotoxicity and cell death was observed in greater than 99% of CHO cells treated with 3 mM 3,4,5-TFA (FIG. 6C).

EXAMPLE 4

Effects of 3,4,5-Trichloro-2-Thiophenecarboxylic Acid on the Growth of Cancer CHO Cells Cells were plated at $1.5 \times 10^5$ cells/60-mm dish; 24 hours later, the medium was removed, and new media with or without 0.1, 1 and 3 mM final concentrations of 3,4,5-Trichloro-2-Thiophenecarboxylic Acid (3,4,5-TFA) were added. Cell counts were determined at 24, 48 and 72 h after the addition of 3,4,5-TTA; each point is the average of triplicate measurements from 3 cultures.

The results show that the growth of CHO cells was strongly inhibited by 1 mM and 3 mM 3,4,5-TTA within 6 h of addition of the substance. At 24 h, 48 h, and 72 h, the growth inhibition induced by 1 mM and 3 mM 3,4,5-TTA was greater than 98% and 100%, respectively (FIG. 5).

After 6 to 12 hours of exposure to 1 and 3 mM 3,4,5-TTA, CHO cells acquired a flattened morphology, they began to look granular, no mitosis were observed, and some began to float in the medium. With longer exposure (24–72 hours) cytotoxicity and cell death was observed in greater than 99.9% of CHO cells treated with 1 mM or 3 mM 3,4,5-TTA (FIG. 6C).

EXAMPLE 5

Effects of 3,4,5-Trichloro-2-Thiophenecarboxylic Acid Hydrazide on the Growth and Viability of Cancer CHO Cells The growth of CHO cells was strongly inhibited by 500 uM 3,4,5-Trichloro-2-Thiophenecarboxylic Acid Hydrazine (3,4,5-TTAH). After 12 to 24 hours of exposure to 500 uM 3,4,5-TTAH, CHO cells acquired a flattened morphology, they began to look granular, no mitosis were observed, and numerous cells began to float into the medium. With longer exposure (24–72 hours) cytotoxicity and cell death was observed in greater than 95% of CHO cells. The detached cells showed conspicuous cytotoxic effects and most of them (>99.9%) were destroyed by the agent, as determined at 72 h using the trypan blue dye exclusion test.

EXAMPLE 6

Effects of 4-butyl-2-Thiophenecarboxylic Acid Hydrazide on the Growth and Viability of Adenocarcinoma Cells 4-butyl-2-Thiophenecarboxylic Acid Hydrazide (4-B-2-TAH; 50 $\mu$M) can inhibit human breast adenocarcinoma MDA-468 cell growth. After 12 hours of treatment with 50 $\mu$M 4-B-2-TAH, there was no further increase in cell number. When treated with 50 $\mu$M 4-B-2TAH, the majority of the MDA-468 cells became granular, showed pronounced cytotoxic effects, many were destroyed and subsequently detached from the culture dish. These floating cells were not viable. Within 48 h of treatment there was greater than 90% decrease in cell number. Thus, breast adenocarcinoma MDA-468 cells are extremely sensitive to the cytotoxic actions of 4-B-2-TAH. Thus, 4-B-2TAH can be effective to reduce and control growth of this common type of human malignancy and possibly other types of human adenocarcinoma such as colon or lung adenocarcinoma.

EXAMPLE 7

Combined Effects of Furoic Acid, 2-Thiophenecarboxylic Acid, or Derivatives thereof with Standard Chemotherapeutic Agents Other chemotherapeutic agents such as 5-fluorouracil, vinblastine, taxol and levamisole, in the case of breast or colon adenocarcinoma, may be utilized in conjunction with the agents of this invention to enhance the effectiveness of cancer therapy. For example, cancer cell death and biological alterations induced by 4-butyl-3,5-difluor-2-Thiophenecarboxylic Acid-Thiosemicarbazone, an agent that molecular modeling and the study of the structure-activity relationships indicates that it has potent anti-neoplastic activity, may be enhanced by using agents from the group consisting of anti-cancer antibodies, radioactive isotopes, and chemotherapeutic agents.

The method of using furoic acid or thiophenecarboxylic acids and derivatives thereof, topically to treat a variety of viral and spontaneous proliferative diseases in human and animal subjects, as will be described in detail below, can be used in combination with cytotoxic agents selected from the group consisting of chemotherapuetic agents, antibodies, and cytokines (e.g. Interferons), for enhanced activity.

DERMATOLOGICAL USE OF THE AGENTS OF THIS INVENTION

Therapy to correct some of the pathological conditions of the skin can be accomplished by the agents of this invention which may be delivered topically, systemically, or intralesionally. Topical therapy is a convenient method of treatment but its efficacy depends on overcoming the barrier function of the skin, primarily that presented by the stratum corneum. The agents of this invention are important as topical and systemic therapeutic agents for skin diseases. Orally, this agents can be used to treat numerous dermatological diseases that include abnormal proliferation or infections. Potent and efficacious derivatives of 2-TH acid can be used for the treatment of acne, psoriasis, and other skin diseases. Modifications of such molecules may result in topical agents that can be used for their anti-carcinogenic and antiaging effects. The following examples delineate some of the skin diseases that can be treated by the agents of this invention.

EXAMPLE 1

Treatment of Psoriasis

Psoriasis is characterized by the pathologically rapid epidermal proliferation induced by an immune-mediated dermal inflammation. Furoic acid or 2-TH acid and derivatives can be used to inhibit cell proliferation and prevent the inflammatory condition of psoriasis. The primary therapeutic mechanism of these agents centers in both inhibition of hyperproliferation and reduction of epidermal inflammation. A usual dose for topical therapy is 5% to 10% of furoic acid or 2-TH acid in an absorption base applied two times daily. Systemic administration can be used in the doses described elsewhere.

EXAMPLE 2

Treatment of Acne

Acne is a common skin disorder through the world, affecting about 7% of the population between 12 and 24 years old. Acne is a disease of the pilosebaceous unit. The pathogenesis of acne includes hyperproduction of sebum, growth of *Propionobacterium acnes*, and inflammation, Furoic acid or 2-TH acid and derivatives can decrease sebum production, inhibit *P. acnes* grow, and reduce inflammation, leading to the control of acne. The lesions can be treated with an aqueous solution or an absorption base containing approximately 5% to 20% furoic acid or 2-TH acid or derivatives thereof. The pharmacological agents can also be used systemically and intralesional in formulations described elsewhere in this application.

EXAMPLE 3

Treatment of Skin Infections

Infections of the skin may be bacterial, viral fungal and parasitic. Topical application of the agents of this invention can be used for the control rosacea, impetigo and other skin infections. Viral infections are numerous and include verrucae (human HPV), herpes simplex (HSV), condylomata acuminatum (HPV), molluscum contagiosum (poxvirus) and chicken pox (varicella) among the most common diseases of the skin. Few medications are available for viral diseases of the skin. Furoic acid or 2-TH acid and derivatives thereof can be used to control viral diseases such as Herpes, HPV and molluscum contagiosum. They can also be used to control fungal and parasitic diseases. The lesions can be treated with an aqueous solution or an absorption base containing approximately 5% to 20% furoic acid or 2-TH acid or derivatives thereof When indicated, the pharmacological agents can also be used systemically and intralesional in formulations described elsewhere in this application.

EXAMPLE 4

Treatment of Exposure to UV Radiation

The exposure of the skin to UV radiation such as sun exposure induces molecular and cellular damage which results in a cellular inflammatory response that includes overproduction of heat shock proteins. The compounds and methods of the present invention can be used to block the excessive molecular stress response caused by UV radiation. The compounds block excessive production of zinc finger proteins involved in inflammation such as DnaJ proteins which are involved in heat shock responses. Formulations of 1% to 10% furoic acid or 2-TH acid and derivatives thereof in an adequate solution or absorption base can be used to treat sunburn.

EXAMPLE 5

Treatment of Neoplasms of the Skin

The agents of this invention can be use for the treatment and prevention of neoplasm of the skin. The pharmaceutical properties and doses of these agents are discussed elsewhere in this application. Actinic (or solar) keratoses are potentially serious cutaneous neoplasms that are due to chronic UV radiation exposure. Prevention and treatment of Actinic keratoses can be accomplished by topical applications of Furoic acid or 2-TH acid and derivatives thereof. Topical concentrations of 1%, 2% and 5% as creams or solutions may be applied twice a day or in an alternative acceptable regime.

EXAMPLE 6

Simultaneous Activation of Macrophages and Induction of Apoptosis in Melanoma Cells by 2-TH Acid: Macrophages in and Around the Areas of Metastatic Melanoma Phagocytize Apoptotic Melanoma Cells after Treatment with 2-TH Acid We have previously observed that macrophages in melanomas are very active, suggesting a direct role of macrophages in phagocytosis of melanoma cell debris following apoptosis, a common phenomenon. In contrast, benign nevus rarely show macrophages or they are non-existent. We have found that 2-TH acid and derivatives can stimulate macrophages to digest apoptotic melanoma cells. Apoptosis in melanoma cells is induced by the agents of this invention. Thus, the agents of this invention can be used topically or systemically to stimulate phagocytosis of melanoma cells by macrophages in and around the areas of metastatic melanoma cells which are simultaneously induced to enter into apoptosis by 2-TH acid and derivatives thereof. The lesions can be treated with an absorption base containing approximately 5% to 20% 2-TH acid or derivatives thereof. When indicated, the pharmacological agents can also be used systemically and intralesional in formulations described elsewhere in this application.

EXAMPLE 7

Treatment of Poison Ivy Contact Dermatitis

The Anacardiaceae are known for the toxic components of some of the members of this family, specially poison ivy (Toxicodendron radicans), poison oak, and poison sumac in North America. This plant produces contact dermatitis due to the production of urushiol which is a complex mixture of lipophilic immunogenic cellular protein-binding compounds. The antigenic component of poison ivy, oak and sumac is called urushiol. Poison ivy urushiol is mostly composed of pentadec(en)yl catechols.

The antigens of allergic poison ivy contact dermatitis are lipid soluble and bind to specific proteins of the skin Langherans cells (skin macrophages). In the Langerhans cells, the lipophilic urushiol antigens are internalized by endocytosis with the antigen subsequently degraded to be presented to T-Lymphocytes. This universal mechanism of antigen processing also occurs with viral, bacterial, fungal, tumor, or transplantation antigens as well as with urushiol. Subsequently, the T-lymphocytes recognize the antigens (urushiol) with the help of the antigen presenting cells (Langerhans cells) and the poison ivy reaction is initiated.

Poison Ivy can be alleviated by the use of the agents of this invention. The agents can be used to increase the protein-antigen degrading activity of macrophages (Langherans cells) and to inhibit the T-cell lymphocytes inflammatory response. The poison ivy, oak or sumac lesions can be treated with an absorption base containing approximately 5% to 20% 2-TH acid or derivatives thereof When necessary, the pharmacological agents of this invention can also be used systemically in formulations described elsewhere in this application.

OCULAR PHARMACOLOGY

The antimicrobial agents of this invention can be used to treat ocular diseases. The agents can be employed as antivirals for herpes simplex of the eye or as antibiotics for endophtalmitis. They may also have uses in fungal and parasitic diseases of the eye.

EXAMPLE 1

Treatment of Viral Keratitis

Viral keratitis, an infection of the cornea, is most commonly caused by herpes simplex type I and varicella zoster viruses. Herpes II and cytomegaloviruses can also cause keratitis. Topical antivirals of this invention can be use for the control of these conditions. The topical of intraocular ophthalmological preparation includes from 0.01% to 5% 2-TH acid or its substituted derivatives in an osmotically appropriate vehicle.

EXAMPLE 2

Treatment of Fibroblast H Hyperproliferation in the Eye

Hyperproliferation of fibroblasts in the eye after cataract surgery or implantation of artificial crystalline lens, may result in the opacity of the lens. At present, 5-flurouracil (5-FU) and other antiproliferative agents are instilled in the eye to control fibroblast proliferation. However, 5-FU is difficult to control and has untoward effects. The chelating agents of this invention can be used to control fibroblast hyperproliferation. An additional potential advantage of these agents are the simultaneous effects as inhibitors of angiogenesis, making 2-TH acid and derivatives suitable drugs after ophthalmic surgery.

2-THIOPHENECARBOXYLIC ACID AND PHARMACOLOGICALLY ACCEPTABLE DERIVATIVES THEREOF IN THE DOSAGES DELINEATED ABOVE CAN BE USED TO PREVENT THE FORMATION OF ABERRANT IRON AND COPPER-FINGER PROTEINS INVOLVED IN CARCINOGENESIS AND AGING

The chelating agents of the present invention can also be used as chemopreventive agents to control the formation of aberrant metalloproteins involved in carcinogenesis and aging.

Transition metal ions at physiological concentrations, such as iron, cobalt, copper, etc., are essential elements for biological functions, however at higher levels they are toxic. This is particularly true for iron. Elevated levels of iron contribute to carcinogenesis in several ways: First, iron has the capacity to generate highly reactive free radicals which damage DNA; and Second, there is an increased iron requirement by rapidly proliferating transformed cells for DNA replication (ribonucleotide reductase) and energy production by mitochondria (Fernandez-Pol, 2000, 2001).

Recent studies offer new insight into the mechanisms and potential for damage to DNA by transition metals, particularly by iron, and copper. These new insights result from the discovery that transcriptional regulatory proteins that interact with DNA (DNA binding proteins) which normally bind zinc (zinc finger domains) but which can substitute zinc by other transition metals present in the cell at abnormal concentrations may be involved in the degradation of DNA genetic regulatory response elements leading to carcinogenesis and aging.

Heavy metal incorporation into zinc finger proteins (ZFP) may be important in metal-induced toxicity. An iron-substituted zinc finger may generate free radicals which damage DNA and potentially induces carcinogenesis. The capability of iron to replace zinc in zinc finger, denoted the iron finger, was demonstrated in a series of experiments both in vivo and in vitro. Iron has the ability to substitute for zinc in many ZFP. The iron finger in the presence of $H_2O_2$ and ascorbate generates highly reactive free radicals (hydroxyl), producing a reproducible cleavage pattern to the DNA of the respective response element. The close proximity of the zinc finger to DNA, as found by computer modeling, suggests that the iron-substituted zinc finger may generate free radicals while bound to genetic regulatory response elements, leading to degradation of DNA and/or carcinogenesis (Fernandez-Pol, 2001). In summary, data at the molecular and clinical level support the notion that biologically essential heavy metals and free radicals influence the aging process and induce carcinogenesis by interfering with normal functions of regulatory ZFP.

Transition metal ions, particularly cupric ions and complexes containing $Cu2+^+$ and ferric ions and complexes containing Fe3+ can dissociate and replace the zinc ion from the zinc finger of important regulatory proteins. For example, zinc finger containing hormone receptor proteins for testosterone, progesterone, etc, can replace zinc by iron and may generate free radicals which damage DNA in specific regulatory regions and potentially induced carcinogenesis in prostate, uterus, etc, respectively. Thus, classical hormones can modulate iron finger receptor proteins, suggesting that these hormones potentiate the destructive actions of free radicals, mediated by abnormal iron finger receptor proteins, on regulatory regions of DNA.

The inventors have determined that it is feasible to maintain zinc finger proteins in an undamaged zinc-containing form by using a combination of specific chemopreventive agents such as specific iron chelators and radical scavengers that, respectively, interfere with the formation of both aberrant iron finger proteins and free radicals. Thus, 2-TH acid and pharmacologically acceptable derivatives thereof in the dosages delineated above can be used to prevent the formation of aberrant iron and copper-finger proteins involved in carcinogenesis and aging.

Metalloenzyme Targets

Matrix metalloproteinases, also called matrixins, are a family of structurally related Zn2+ enzymes that mediate the breakdown of connective tissue. Today more than 20 enzymes are known. The most common belong to the families of collagenases, gelatinases, and stromelysins. The substrates for these enzymes include collagens, elastin, proteoglycans, serpin, and gelatin. The functions of matrix metalloproteinases include trophoblast invasion, mammary gland involution, and skeletal and limb development.

One important feature of the matrixins is that many of these genes are "inducible". The effectors include growth factors, cytokines, chemical agents, viruses, etc. These enzymes are highly regulated by endogenous proteins inhibitors (e.g. alpha2-macroglobulin) and tissue inhibitors of metalloproteinases (TIMPs). Abnormal regulation occurs in numerous diseases such as invasive tumor growth and angiogenesis, rheumatoid arthritis, and in aneurysms.

All matrixins are synthesized as prepro-enzymes and secreted as inactive pro-MMPs in the majority of cases. The matrixins contain two zinc atoms, a catalytic zinc and a structural zinc. The catalytic zinc is bound to 3 histidines within a conserved sequence. In inactive enzymes the catalytic Zn is also bound to a cysteine SH group in another conserved sequence. The mechanism of action of matrixins includes the coordination of the carbonyl carbon of the peptide bond to zinc which results in nucleophilic attack and subsequent peptide cleavage.

More specifically, the pro-peptide domain has a conserved unique PRCG(V/N)PD sequence. The cysteine within this sequence (the "cysteine switch") binds the catalytic zinc to maintain the latency of pro-MMPs. The catalytic domain contains a highly conserved zinc binding motif HEXX-HXXGXXH. The catalytic domains of matrixins have an additional structural zinc ion and 2 to 3 calcium ions, which are required for stability and expression of enzymatic activity.

It has been determined that the effective inhibitors of matrixins of the instant invention must have the following groups: 1) one functional group capable of binding to the catalytic zinc such as carboxylic acid, thiol, or hydroxamic acid; 2) have at least one functional group which can H-bond with the enzyme backbone; and 3) have one or more side chains capable of favorable London interactions with the enzyme active site.

Examples of the specific effects of metal chelating agents on matrixins, including 2-thiophenecarboxylic acid and derivatives, as well as the practical application of those agents will now be described:

EXAMPLE 1

Simultaneous Inhibition of Tumor Angiogenesis (Vascular Endothelial Cell Proliferation), Cancer Cell Proliferation, and Invasion by 2-Thiophenecarboxylic Acid and Analogues Inhibitors of Zinc-Dependent Matrix Metalloproteinases (MMP) and Copper Requiring Enzymes The chelating agents of the present invention can also be used to control the initiation of neovascularization in various disease conditions. Neovascularization is dependent on zinc-requiring matrix metalloproteases (Zn-MMPs). The administration of the specific chelating agents of the instant invention can prevent unwanted angiogenesis. The chelating agents can be administered orally or parenterally in doses described elsewhere in this application.

Figure 10:
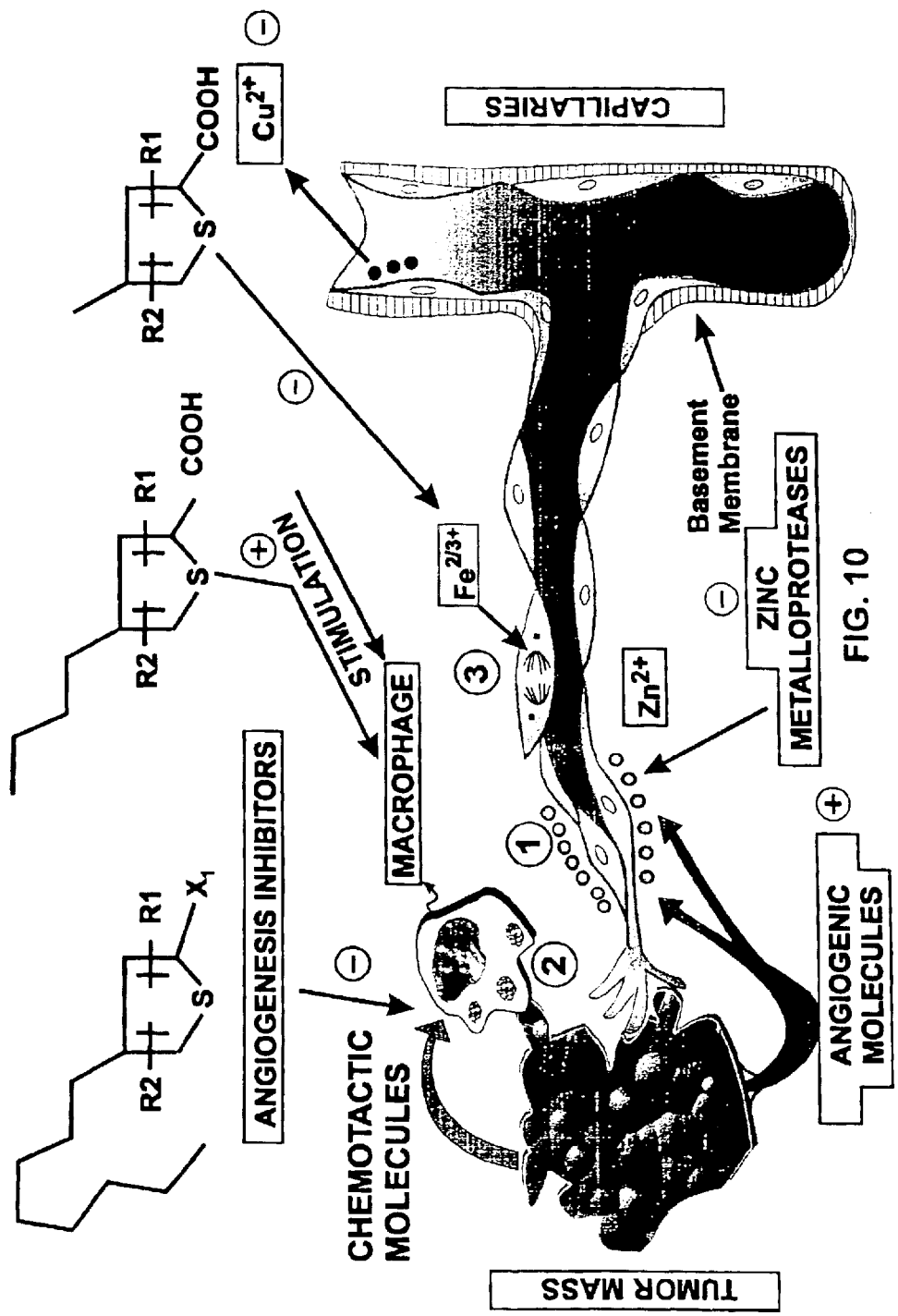
FIG. 10 is a hypothetical scheme of inhibition of angiogenesis by the agents of this invention which can inhibit multiple targets such as zinc-, copper-, and iron-dependent metalloproteins and metalloproteases which are involved in proteolysis of the extracellular matrix (1), cell migration and chemotaxis (2), and cell proliferation (3).

One group of proteolytic enzymes susceptible to the agents of this invention are the Zn-MMPs. Controlling Zn-MMP activity using the synthetic small molecule inhibitors of this invention is an important mechanism to stop several of the rate-limiting steps in this pathway leading to angiogenesis and invasion. As shown in FIG. 10, inhibition of angiogenesis can be accomplished by the simultaneous inhibition of the following entities: 1) MMPs which are involved in proteolysis of the intracellular matrix, 2) cell migration; and 3) chemotaxis; and cell proliferation.

The growth of solid tumors depends on neovascularization, extensive cell proliferation, and local migration of cancer cells (FIG. 10). Angiogenesis can be considered an invasive process in which activated vascular endothelial cells proliferate, adhere to extracellular matrix molecules, and migrate. A similar sequence of events regulates cancer cell invasion. Zinc-dependent MMPs are involved in both the angiogenic and the invasive process. Zn-MMPs degrade the extracellular matrix molecules and create a permissive environment for cell invasion and migration. Malignant tumors are characterized by an increase activity of Zn-MMPs.

The 2-thiophenecarboxylic acid and derivatives can act simultaneously to inhibit angiogenesis, cell proliferation (vascular endothelial and cancerous cell), and cellular migration (FIG. 10). Solid tumors are characterized by high proliferation rate, extensive angiogenesis, aggressive local invasion, and metastasis, which eventually make these tumors resistant to conventional treatment such as surgery, chemotherapy and radiotherapy.

Our data shows that 2-TH acid and derivatives can interfere with malignant tumor development by both angiogenic dependent and independent mechanisms. More specifically, the 4-butyl-2-Thiophenecarboxilic acid hydrazide (4-B-2-TAH) was recognized by the inventors to have an anticancer and antiangiogenic activity in vivo.

The properties of 4-B-2-TAH can be summarized as follows: The drug interacts with various target metalloproteins such as Zn-MMPs (FIG. 10). Furthermore, it has been shown that Cu2+ requiring enzyme systems are essential for tumor angiogenesis. These Cu2+ metalloenzymes are also inhibited by 4-B-2-TAH (FIG. 10). This agent also affects zinc finger proteins and ribonucleotide reductase that are important in growth control mechanisms of both endothelial and cancer cells. It is clear that 4-B-2-TAH not only inactivates Zn-MMP extracellularly, but by virtue of its 4-butyl group penetrates the cell interior much more easily than 2-TH acid, and works as an specific intracellular Zn/Cu/Fe chelating agent, inhibiting malignant tumor formation at multiple target points (FIG. 10).

More specifically, 4-B-2-TAH at $\mu$M concentrations can covalently and coordinately bind to the catalytic zinc-containing site of the Zn-MMPs, rendering the enzyme inactive. Furthermore, uM concentrations of 4-B-2-TAH showed pronounced cytotoxic effects in many different cancer cell lines in vitro which were destroyed by this agent and thus were not viable. Therefore, 4-B-2-TAH can inhibit Zn-MMPs involved in angiogenesis and also can inhibit cancer cell growth in vitro of many adenocarcinoma cells which are extremely sensitive to the cytotoxic actions of this agent. Thus, 4-B-2TAH can be effective to simultaneously control angiogenesis (inhibition of endothelial cell proliferation, Zn-MMPs, and Cu2+ metalloenzymes), cancer cell growth (disruption of zinc finger proteins and inhibition of ribonucleotide reductase), and cell migration-inhibition of Zn-MMPs) in many common types of solid tumors such as breast, colon or lung adenocarcinoma.

EXAMPLE 2

Treatment of Pulmonary Anthrax by Blocking Lethal Factor, a Highly Specific Zinc-Dependent Metalloprotease That Contains a Zinc-Dependent Catalytic Center The chelating agents of the present invention can also be used to control systemic infections produced by B. Anthracis spores in various organs, including cutaneous, intestinal, and the most deadly forms of this disease, meningitis and pulmonary anthrax in animals and humans.

The compounds of this invention can be used to effectively neutralize the Lethal Factor (LF) of B. Anthracis. The LF belongs to the family of zinc-dependent metalloproteases. LF contains a zinc-dependent catalytic center which is essential for the proteolytic and pathogenic functions of this protein. As will be shown later, the zinc-dependent catalytic center of LF can be covalently neutralized by the agents of this invention.

LF is a zinc-metalloenzyme target for the specific therapeutic agents of this invention such as 2-Thiophenecarboxylic acid hydrazide (2-THA), 4-Butyl-THA-hydrazide, 4-butyl-THA-hydrazone or 4-butyl-TCA-thiosemicarbazone, and their derivatives thereof, that can inhibit the catalytic activity of LF by covalent binding to the zinc-dependent catalytic motif of LF. The 2-TH and derivatives thereof are powerful metalloprotease inhibitors that can block the toxic effects of LF by covalent binding to the zinc-dependent catalytic domain of LF in vitro and in vivo, as determined by molecular and cellular trafficking modeling.

It is the purpose of this example to demonstrate that some of the specific compounds of this invention with special characteristics (e.g. specific covalent binding to the zinc-depend catalytic center) can be used to neutralize the LF toxin which conceivably could provide a modern life-saving tool and protecting agent in an emergency situation in which the pulmonary or meningeal disease has progressed to a point where antibiotic treatment is ineffective.

Anthrax is a significant agent of biological warfare and terrorism in the form of spores which when inhaled produce pulmonary Anthrax. Although antibiotics can control certain forms of Anthrax, inhalation anthrax, which is produced by the spores of *Bacillus anthracis* is fatal in the majority of cases due to the late diagnosis of the disease making antibiotic treatment ineffective.

Research in the pathogenesis of anthrax identified two unique virulence factors of anthrax pathogenesis: poly-D-glutamic acid capsule and a tripartite protein toxin.

The anthrax toxin has three components which act in concert: protective antigen (PA), oedema factor (EF), and lethal factor (LF). The PA is a four-domain protein that binds a host cell-surface receptor; cleavage by a furin-like protease allows PA to form heptamers that bind the toxic enzymes EF and LF. Subsequently, the complex is endocytized, inserted into the endosome membrane, followed by translocation of the EF and LF into the cytosol. The binary combination of PA and LF (lethal toxin) is sufficient to induce rapid death in animals when given intravenously.

Of significant importance for this invention is that certain metalloproteases inhibitors can covalently bind to the Zn-dependent catalytic center of LF, and they can block the toxic effects of LF in vitro and in vivo, as determined by molecular and cellular modeling. Therefore, LF has been identified as a target for therapeutic agents that can inhibit its catalytic activity or block its association with PA.

PA possesses a high affinity binding site for which the LF and the EF catalytic components compete. The PA63 complexed to the catalytic component undergoes receptor mediated internalization and translocation into the cytosol where the LF and EF are released to perform their enzymatic activities. EF is an adenylate cyclase, calmodulin-dependent, and hence only functional in eukaryotic cells.

Figure 11:
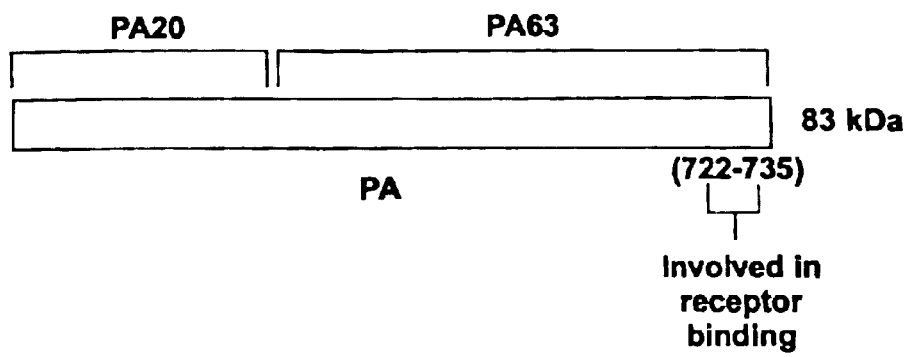
FIG. 11 is a schematic block diagram of the Lethal Factor polypeptide component of the anthrax toxin. Lethal Factor (LF) is an 87 kDa polypeptide and is the catalytic component of the anthrax toxin. Amino acids 401–776 comprise the catalytic domain. This region contains at least one zinc-binding motif which is involved in the LF proteolytic activity in macrophages. The definitions of domains is based on 3D-structures and sequence alignments using standard algorithms.
Figure 11:
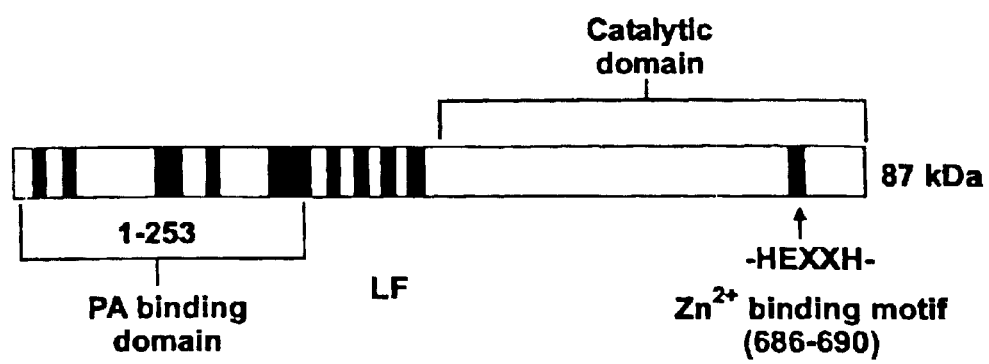
Figure 11:
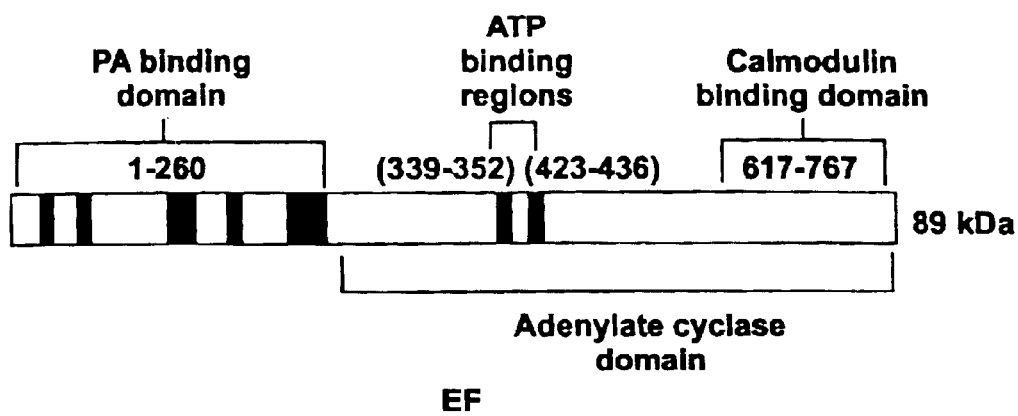

Lethal Factor (LF) is a protein (Mr=90,000) that is instrumental in the pathogenesis of anthrax (FIG. 11). It is a highly specific metalloprotease that cleaves proteins belonging to the family of mitogen-activated protein kinase-kinase (MAPKK), leading to the inhibition of various signaling pathways. This protein is related to the zinc metalloprotease family and contains a zinc-dependent catalytic center. LF contains one or more $Zn^{2+}$-binding amino acid motifs, one of which is characteristic of the thermolysin family of zinc-dependent metalloproteases. The MAPKK family of proteins are the only known cellular substrates of LF. In tumors, the LF toxin inhibits tumor cell growth and angiogenesis, most likely by inhibiting the MAPKK-1 and MAPKK-2 pathways.

The binary combination of PA+LF is lethal to laboratory animals and lysis cells of the monocyte/macrophage lineage. In pulmonary anthrax, the LF leads to lysis of macrophages within 60-90 minutes by apoptosis. When the lethal toxin (PA+LF) is administered intravenously to rats, death is produced within 60-90 minutes and is characterized by severe pulmonary edema The lethal effects on macrophages in vitro has been demonstrated to be calcium-dependent. Chelators of $Ca^{2+}$ such as EGTA can protect macrophages from the lytic effect of the LF.

Antibiotics are not active against the spore forms of *B. Anthracis*. Although antibiotics are administered prophylactically to subjects exposed to aerosolized spores, it may be considered prudent and advantageous to administered an anti-LF agent which will neutralize the deleterious effects of this potent toxin.

The anthrax toxin lethal factor binds multiple zinc atoms. Results from atomic adsorption spectroscopy indicate that LF contains approximately three zinc atoms per toxin molecule. LF treated with EDTA and o-phenanthroline contained a similar number of zinc atoms, indicating that all three zinc atoms are tightly bound to the protein. LF contains the highly conserved zinc-binding consensus sequence, HexxH, that is present in all known zinc metalloproteases. In addition, lethal factor contains an invented form of the motif, HxxDH, which may also be involved in zinc binding.

Molecular modeling studies showed that a zinc ion ($Zn^{2+}$) is coordinated tetrahedrally by a water molecule and three protein side chains, in an arrangement resembling the thermolysin family. We built a computer peptide model that shows that the compound 4-butyl-THA-hydrazine can make covalent contact with the catalytically active $Zn^{2+}$, leading to a conformational change that neutralizes the metalloprotease activity of the LF. The surfaces on the adjacent region of the $Zn^{2+}$ binding site can also provide additional docking sites for derivatives of the 4-butyl-THA-hydrazine family that can be use as therapeutic agents that will block the activity of LF in vivo.

It will be appreciated by those skill in the art that the inventor has disclosed the best mode of the invention. Therefore, the foregoing specifications and accompanying drawings (FIG. 11) are intended to be illustrative of this example only.

Thus, suitable doses of the disclosed 4-butyl-THA-hydrazine and derivatives thereof, particularly those shown to penetrate macrophages and to cross the blood-brain barrier (4-butyl-TFA-thiosemicarbazone), which can be useful in cases of *B. Anthracis* meningitis, can be used to treat the lethal factor toxin component of pulmonary anthrax. Furthermore, the claimed invention is intended to apply to other pathological conditions which involved the LF both presently known and unknown.

EXAMPLE 3

Antifungal Activity of 4-butyl-2-Thiophenecarboxylic Acid Hydrazide and Analogues The chelating agents of the present invention can also be used to control topical and systemic fungal infections in various disease conditions. It has been documented that copper, zinc, and iron are essential metal ions in critical fungal enzymes such as superoxide dismutase, metalloproteases, and ribonucleotide reductase, respectively. In general, the increased proliferation rate of fungus is the result of availability of nutrients and transition metal ions which activate essential metalloenzymes. The administration of the specific chelating agents of the instant invention can prevent unwanted fungal proliferation by blocking the activity of these metalloenzymes. The chelating agent can be administered orally or parenterally in doses described elsewhere in this application.

Antifungal agents are naturally occurring compounds or synthetic that have in vitro and in vivo activity against yeast, mold or both. Since fungi and mammalian cells are eukaryotic, and the antifungal agents inhibit synthesis of proteins, RNA and DNA, they have toxic effects in the mammalian host.

The high incidence of toxicity among antifungal agents results in the fact that there are only a few antifungal agents currently used in human treatment. However, the number of fungal diseases has increased in the past 30 years, especially among immunocompromised patients which are at high risk for life-threatening mycosis. Topical use is also increased due to the fungal infections of the nails.

The agents of this invention can be used use as novel antifungal agents in animal and human mycoses, in mycotic infections, and in emerging fungal infections in immunocompromized patients. They can be used in superficial and systemic mycosis. For example, they can be use for topical use in nail infections and for systemic use in immunocompronized patients such as those having AIDS or lung transplant fungal infections.

If some of the selected agents show untoward toxicities in clinical trials, such as lysis of erythrocytes, they can be modified by incorporating the agents of this invention in lipid bilayers, in order to protect the erythrocytes and thus make the drug available as a systemic agent. The agents of this invention and in particular the lipophilic 4-butyl/pentyl-substituted derivatives of THA-hydrazide can be incorporated in multilamellar liposomes which can contain specific ratios of lipids such as phospholypids dymyristoyl phosphatydylcholine (DMPC) and dimyristoyl phosphatydylglycerol (DMPG) in a 7:3 ratio. This lipid-modified antifungal agents can be administered in doses equivalent to those described elsewhere.

It will be appreciated by those skill in the art that the inventors have disclosed the best mode of the invention for treatment of fungal diseases. Therefore, the foregoing specifications and accompanying drawings are intended to be illustrative of this example only.

EXAMPLE 4

Antiparasitic Activity of 4-butyl-2-Thiophenecarboxylic Acid Hydrazide and Analogues Practical, effective, and inexpensive drugs are needed to treat parasitic infections, particularly malaria The practical, effective, and inexpensive chelating agents of the present invention can be used to control parasitic infections in various disease conditions in animals and man.

It has been documented that copper, zinc, and iron are essential metal ions in critical parasitic-encoded enzymes such as zinc finger ribosomal proteins (MS/S27), Zn-dependent metalloproteases, and ribonucleotide reductase, respectively. The administration of the specific chelating agents of the instant invention can prevent unwanted parasitic proliferation by blocking the activity of these metalloenzymes. The chelating agent can be administered orally or parenterally in doses described elsewhere in this application. Furthermore, the drugs developed for other clinical indications in this invention can be used to treat animals and men hosting parasites. These drugs can be effective for multi-drug resistant parasites. These new drugs can also be use for prophylaxis.

In addition to malaria, other protozoans within the scope of the subject invention are intracellular parasites of man and animals, for example, Plasmodia, Toxoplasma, Amoeba histolytica, and Trypanosomas. Of course, the agents of this invention can be used to treat heimintic diseases such as filariasis.

Parasitic infections caused by pathogenic protozoa affect a large proportion of people of this planet and results in a substantial health and economic burden. Military operations, world travel and less-developed countries promote the infections by these agents. Malaria affects more than 500 million people and causes about 2 million death each year. This disease affects children, pregnant women and immunocompromised individuals such as those having AIDS.

Malaria is an enormously negated disease. Malaria, particularly the clinical form produced by *Plasmodium falciparum*, is the most devastating disease, and thus it causes high morbidity and mortality. Chemotherapy is the most cost-effective way to control most parasitic infections, including malaria. Many of the drugs used to combat such infection have been in use for over 50 years. Therefore, one of the major problems is resistance to the agents used for chemotherapy.

New or superior pharmaceuticals are urgently required to control systemic infections such as Malaria, Chagas' disease, visceral Lehismaniasis, etc. These new drugs are needed to prevent the development of drug resistance. Because protozoa proliferate rapidly in the host, they develop resistance to drugs readily.

The complex life cycle of malaria makes it difficult to attack this parasite. At each stage the parasite produces different proteins. Thus, to kill malaria, a drug must target different proteins at different parasitic life stages. However, from gene data banks we have identified a class of metalloprotein genes essential for parasite survival that are expressed at all stages of the life cycle of malaria. These genes are involved in protein synthesis and fat production and are essential for parasite survival. Furthermore, these genes are sufficiently different form human genes, are zinc finger proteins and parasite transition metal ion-dependent metalloproteinases that can be targets for the new drugs of this invention The development of economic, safe and effective broad-spectrum agents to treat parasitic diseases is one of the purposes of this invention. The method is based on the actions of the compounds presented here on essential parasitic-encoded zinc finger proteins such as ribosomal protein MPS/S27 and/or parasitic metalloproteinases. Purified or synthetic parasitic metalloprotein targets for drug action can be developed for rapid, automated in vitro procedures to select the best possible drug molecule presented in this invention. The agents of this invention have broad-spectrum activity against all developmental stages of the parasite but particularly the proliferating stages. The agent can be used for mass chemotherapy orally and it will not induce drug resistance.

This example deals with the properties and uses of 4-butyl-THA-hydrazide and derivatives thereof to treat and prevent malaria caused by four species of Plasmodium, of which *P. falciparum* is the most fastidious. This agent acts in the asexual erythrocytic stages of malarial parasites and in the latent tissue forms of this parasite. Since no single agent has successfully controlled the emergence of drug-resistant strains, this drugs will be used in multidrug regimens. The agents of this invention act on the primary tissue forms of plasmodia and can be used in prophylaxis. Due to the low toxicity, this agents can be use to produce a suppressive cure, eliminating all parasites from the host.

There are diseases such as Trypanosomiasis and Leishmaniasis that affect millions of people in the tropics. Effective antiprotozoal drugs for treatment of major protozoal infections such as African Trypanosomiasis (sleeping sickness), Chagas' disease, and visceral Leismaniasis are still lacking. Many of the drugs used are toxic and produce resistance.

The chelating agents of the instant invention can be as effective or superior to benznidazole, the compound currently in clinical use for the suppression of the reproduction of epimastigotes of *Trypanosoma cruzi* the protozoa that causes Chagas' disease. The mechanism of action of the anti-parasitic chelating agents is in intracellular sites of the epimastigote involving iron, copper, or zinc neutralization. The target protein can be a small evolutionary conserved parasite-encoded zinc finger protein such as the MPS/S27 ribosomal protein from *T. cruzi* or other essential parasitic metalloenzymes. The results indicate that certain degree of hydrophobicity is necessary for the agents of this invention to penetrate the parasites (FIG. 7). The drugs of this invention, particularly the hydrophobic derivatives can also be used to treat toxoplasmosis and cryptosporidiosis which are common in AIDS patients.

The development of the antiprotozoal drugs of this invention which are specially designed chelating agents to selectively disrupt zinc finger proteins and inactivate zinc-metalloproteases critical for the metabolism of the parasite should provide a new generation of drugs that can be used in the treatment of the parasitic diseases delineated above.

It will be appreciated by those skill in the art that the inventors have disclosed the best mode of the invention for treatment of parasitic diseases. Therefore, the foregoing specifications and accompanying drawings are intended to be illustrative of this example only.

NEURODEGENERATIVE DISEASES

INHIBITION OF POLYMERIZATION OF AMYLOID, PRIONS AND OTHER TRANSITION METAL ION-DEPENDENT MONOMERIC PRECURSOR PROTEINS BY 4-BUTYL-2-THIOPHENECARBOXYLIC ACID AND ANALOGUES

The chelating agents of the present invention can also be used to control metal-dependent protein aggregation in various disease conditions such as Alzheimer's, Prion diseases and other diseases involving protein aggregation. It has been documented that $Fe^{2+}$ and $Cu^{2+}$ are involved in abnormal protein aggregation in neurons. The increased formation of abnormal aggregates in neurons results in apoptosis. The administration of the specific chelating agents of the instant invention can prevent unwanted protein aggregation in neurons. The chelating agent penetrates the blood-brain barrier and can be administered orally or parenterally in doses described elsewhere in this application.

The most common neurodegenerative (ND) diseases are Alzheimer's disease (AD), Huntington's disease, and Prion diseases. Although at the clinical and neuropathological level these diseases are distinct, at the transition metal ion (TM) level they may have certain unifying features.

AD is a progressive and largely untreatable disease. The benefits that drugs produce are marginal if any. Most patients after brief initial gains, merely decline more slowly. Thus, the treatments presently available for AD are symptomatic and do not alter the progression of the disease.

Protein aggregation in neurons is a key feature of several incurable neurodegenerative diseases of adulhood such as Alzheimer's, Huntinton's, and spongiform prion-induced encephalopathy. Elucidating the mechanisms of protein aggregation and development of pharmacological anti-aggregation agents is important to the development of therapies for these diseases.

The development of toxic protein aggregates in these diseases is a nucleation-dependent process that can be inhibited by drugs including those of this invention. Insoluble, protease resistant, fibrillar protein aggregates have previously been found in the brains of patients with AD and also in certain transgenic mice animal model systems. These diseases develop slowly, as would be expected if aggregation were the primary cause.

A therapeutic strategy is the development of specific chelating agents that inhibit TMI-dependent aggregation of specific brain proteins. 4-butyl-2-THA-hydrazide and pharmacologically acceptable derivatives thereof in the dosages delineated above can be used to prevent the formation of aberrant protein aggregates that are induced by the presence of Fe2+, Cu2+, and other TMI, including toxic $Al^{3+}$ that has been involved in the pathogenesis of AD. These agents can be used for the treatment of AD and other ND diseases involving TM-dependent protein aggregates.

The following examples refer to the use of the agents of this invention to inhibit TMI-dependent amyloid aggregation in the brain of patients with AD and Cu2+-dependent Prion aggregation in spongiform encephalopathy. Furthermore, it is also conceivable that some of the agents of this invention may be used to prevent the progression of Parkinson's disease that is associated with oxidative damage to neurons induced by Fe2+ and Cu2+ accumulation in specific areas of the encephalon.

EXAMPLE 1

Design and Testing of 2-Thiophenecarboxylic Acid Analogues Inhibitors of Fibril Polymerization in Neurons Amyloid beta-peptide (Ab) is a 40 amino acid proteolytic fragment of amyloid precursor protein (APP). Neuropathologic and transgenic modeling experiments implicate the increased expression and accumulation of Ab as a necessary step in the pathogenesis of AD. Under physiological conditions, monomeric Ab is a nonpathogenic molecule generated during metabolism of APP. Under pathological conditions, Ab undergoes a chemical process of polymerization that produces amyloid fibrils that are extremely toxic to neuronal cells. The mechanism of amyloid fibril toxicity is associated with perturbations of transition metal ion metabolism (Cu2+, Zn2+, Fe2+), Ca2+ homeostasis, and oxidative damage that leads to neuronal apoptosis. Although the mechanism of polymerization is not clearly understood, suppression or prevention of the transition of Ab from monomeric to highly toxic polymeric forms has been identified as a target in the development of therapies for AD. This example details our design and testing of chelating agents inhibitors of polymerization of Ab as potential therapeutics for AD.

One solid hypothesis about how to restrict A-beta's accumulation is the use of chelating agents. This hypothesis was based on the observations that zinc, copper, and iron can rapidly induce the conversion of A-beta into amyloid. High concentrations of these three transition metals in Alzheimer's plaques have been reported by numerous investigators. It was demonstrated that copper and iron were extremely active in that they accelerated both A-beta polymerization and A-beta-related free radical and oxidative stress to neurons.

Thus, it appears that would be beneficial to have a specific chelating agent that removes metals from the specific brain microenvironment and could be incorporated in a pharmaceutical form that will penetrate the brain It is conceivable that by removing the TMI, the A-beta would not cluster in the neurons and that the amyloid plaques will be dissolved and/or the aggregates will not form.

Several groups have published data on approaches to develop chelating agents inhibitors of amyloid fibril formation. A number of chelators such as pyridine carboxylates work quite well in vitro as demonstrated by the fact that they prevent A-beta's clumping in a test tube, and some chelators even dissolved amyloid taken from autopsied Alzheimer's brains. However, these chelators showed sharp dose-response curves consistent with the fact that they are too harsh of a treatment to have the potential for chronic therapeutic applications in animals or humans. The fact is that these carboxylic acid and derivatives removed too much metal from the body, depleting vital amounts of TMI and thus decreasing the cells' energy with resulting apoptosis. These carboxylic acid chelators and derivatives are strong chelators that when added to foods, it ensures that metal-dependent types of bacteria will not survive. We turn, instead, to more specific and less active TMI-binding agents, with high lipid membrane permeability. These compound which are the subject of this invention can be developed into new drugs based on our compound's potential as a metal-ousting anti-amyloid therapy.

We have begun to work with novel chelating agents derivatives of 2-TH acid that show sigmoidal dose-response curves, have wide effective dose-ranges (1 to 20 uM), and high penetrability in brain slices due to their lipophilic side chains. This example describes the essential elements of the design and testing of such gentle compounds that can be use to prevent polymerization of Ab intracellularly in neurons without inducing toxicity or apoptosis.

Amyloid formation can be monitored by several techniques, including electron microscopy, light scattering, cellular toxicity, nucleation and extension assays. In the extension assay, the primary effect of an inhibitor is to slow the rate of fibrillogenesis. The chelating agents of this invention can prevent the polymerization of Ab in extension assays at uM concentrations.

2-TH acid and derivatives are drugs that act by attacking the basic process of AD. They block the formation of amyloid fibrils. Thus, 2-TH acid and pharmacologically acceptable derivatives thereof in the dosages delineated above can be used to prevent the formation of aberrant TMI-dependent protein aggregates in AD. This example demonstrates the possibility of developing therapeutic agents that may alter the course of AD by preventing neuronal death These drugs should help in maintaining or improving cognition, memory and global function The development of the anti-amyloid drugs of this invention which are specially designed chelating agents to selectively disrupt Ab aggregation should provide a new generation of drugs that can be used in the treatment of the AD and possibly other diseases discussed below.

It will be appreciated by those skill in the art that the inventors have disclosed the best mode of the invention for treatment of protein aggregation diseases. Therefore, the foregoing specifications and accompanying drawings are intended to be illustrative of this example only.

EXAMPLE 2

Prions Bind Copper and are Susceptible to Modulation by 2-TH Acid and Derivatives Computational molecular models, optical spectroscopy and nuclear magnetic resonance (NMR) investigations of synthetic prions (PrP) peptides have demonstrated that these proteins are able to bind copper in a specific fashion. The highly flexible NM2-terminus of recombinant PrP is more structured in the presence of $Cu^{2+}$ ions. Each PrP molecule was found to bind two $Cu^{2+}$ ions at pH 6.5. At pH 7.4, four $Cu^{2+}$ ions are bound to the PrP. Other divalent cations including $Co^{2+}$, $Mg^{2+}$, $Mn^{2+}$, $Ni^{2+}$, and $Zn^{2+}$ did not bind to PrP. When $Cu^{2+}$ binds to PrP a sequence corresponding to an octapeptide changes configuration and is transformed in an alpha-helix.

More recently, PrP-deficient mice were found to have lower levels of Zn/Cu superoxide dismutase (SOD) activity. SOD activity has been shown to mirror the state of copper metabolism. Further results indicated that PrP might function as a $Cu^{2+}$ binding protein. Both $Cu^{2+}$ and $Zn^{2+}$ ions have been reported to modify the structure of the N-terminal PrP. However, the molecular basis for these changes are not known.

Disturbances in $Cu^{2+}$ homeostasis leading to diysfunctions of the central nervous system are well documented both in animals and man. For example, Wilson's disease is a genetic disease that involves abnormal copper metabolism. More recently, cuprizone, a $Cu^{2+}$ chelating agent, has been used in mice to induce neurophathological changes similar to those observed in Prion diseases.

If $Cu^{2+}$ is needed to maintain normal Prion configuration, organometalic derivatives of 2-TH acid such as $Cu^{2+}$-2-TH acid may be used to neutralize aggregation of prions induced by $Cu^{2+}$ depletion. For example, $Cu^{2+}$-2-TH acid and derivatives may be used to control the alpha-helix configuration of PrP and thus, they may prevent the deleterious effects of these abnormal proteins.

EXAMPLE 3

Brain Iron in the Pathogenesis of Parkinson's Disease and its Neutralization by the TML Chelators of this Invention A central role of iron in the pathogenesis of Parkinson's disease (PD) is related to its increase in substancia nigra pars compacta dopaminergic neurons and reactive microglia. The deleterious effects of iron in neurons is related to its capacity to enhance production of toxic reactive oxygen radicals in these cells. The critical role of $Fe^{2+}/3+$ in the pathogenesis of nigrostriatal injury is also reinforced by the ability of $Fe^{2+}/3+$ to induce aggregation of alpha-synuclein and toxicity in these cells. Because many neurodegenerative diseases show increased accumulation of $Fe^{2+}/3+$ at the site of neurodegeneration, it is believed that maintenance of cellular iron homeostasis is critical for the survival of neurons. Furthermore, both oxydative stress and accumulation of iron are involved in the induction of apoptosis in PD. Prevention of the production of free radicals may be of therapeutic importance in PD. The neutralization of $Fe^{2+}/3+$ in the neurons can be accomplished by the specific TMI chelators of this invention such as 4-butyl-2THA-hydrazide which penetrates the blood brain barrier.

INFLAMMATORY RESPONSE

Inflammation is an essential pathophysiological response to a large number of diseases which can affect all tissues and organ systems. Diseases involving inflammation can be acute and fatal whereas others are chronic. The development and maintenance of inflammation is controlled by a complex network of humoral and cellular factors. Paracrine hormones such as the eicosanoids are derived from the oxidative metabolism of arachidonic acid which produces important hormones that include prostaglandins (PG), thromboxanes (TX), leukotrienes (LT), and lipoxins (LX).

The inflammatory response has evolved as a humoral and cellular defense system to protect the tissues when exposed to injury such as chemical, viral, etc. For a number of reasons, such response may become undesirable. The administration of the specific chelating agents of the instant invention can prevent unwanted inflammation. The chelating agent can be administered orally or parenterally in doses described elsewhere in this application.

Furthermore, the claimed invention is intended to apply to other pathological conditions which involved inflammatory responses both presently known and unknown. It will be appreciated by those skilled in the art that the inventors have disclosed the best mode by which they presently understand 2-TH acid and its derivatives, to function in controlling inflammatory responses. However, the scope of the appended claims is intended to include other mechanisms of action, both presently known and unknown, which include metal ion containing proteins as mediators in inflammatory responses including, but not limited to, parasitic diseases such as toxoplasmosis, malaria, and lehismaniasis. It is worth noting here that arteriosclerosis has an inflammatory and proliferative component which may be blocked by the methods and compositions of the instant invention.

It is also important to recognize that 2-TH acid inhibitors may offer several other potential health benefits, including analgesia, and possibly preventive effects against cognitive disorders (e.g. Alzheimers disease), colorectal cancer, and arteriosclerosis formation. The usefulness of this invention has the potential for significant public health rewards.

It will be appreciated by those skill in the art that the inventors have disclosed the best mode by which they presently understand 2-TH acid and its derivatives, to function in the control of pathological inflammatory responses.

There are numerous diseases involving inflammatory responses that may be susceptible to the compounds and methods presented in this invention. The following examples illustrate the use of the agents of the instant invention in common human inflammatory diseases.

EXAMPLE 1

The Compounds and Methods of the Present Invention Can be Used to Inhibit the Action of the DnaJ Zinc Finger Proteins when they are Expressed in Inflammation at Pathologically High Levels Prokaryotes and eukaryotes express numerous heat shock proteins (Hsps) in response to stress, including heat shock, exposure to heavy metals, hormones and viral infections. Hsps also mediate physiological and pathological inflammatory responses. Hsps are involved in cancer, such as colon and breast cancers.

The stress response that includes numerous forms of physiological and pathological stress is involved in viral infection. A prominent feature of this response is the synthesis of a discrete set of zinc finger proteins, known as the heat shock proteins, which at present are denoted molecular chaperons. During infection by certain viruses, heat shock proteins act as intracellular detectors that recognize malfolded proteins. Researchers have found that certain DNA viruses are able to activate heat shock proteins. For example, the Hsp70 (DnaK) is induced by adenovirus, herpes virus, cytomegalovirus, and other viruses.

Figure 12:
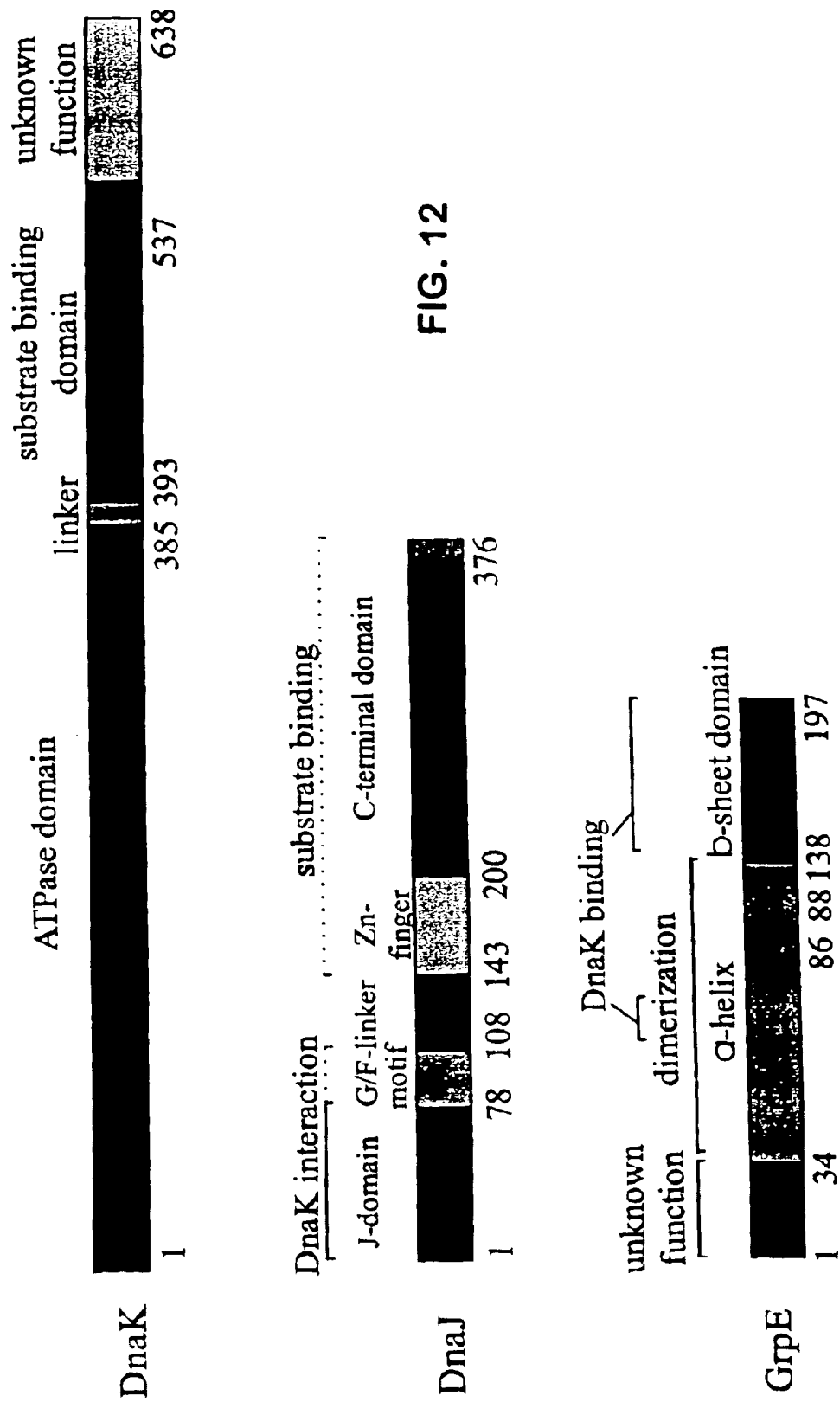
FIG. 12 is a schematic block diagram of the domain organization of DnaJ heat shock protein. DnaJ is a metal-loprotein of 87 kDa which is essential for stimulation of the Hsp70 ATPase activity. Amino acids 143–200 region contains one zinc-binding motif which is involved in substrate binding. The definitions of domains is based on 3D-structures and sequence alignments using standard algorithms.

One of the most interesting proteins involved in the viral infection response is the DnaJ, a heat shock protein which functions in the control of protein folding within the cell (FIG. 12). DnaJ proteins contain two CCCC zinc fingers, defined by the J domain, which is essential for stimulation of the Hsp70 ATPase activity (FIG. 12). Thus, the results suggest that there may be a relationship between the stress response and the cytopathic effects of certain viruses such as herpes viruses.

The response of cells to stress, such as exposure to UV radiation, chemicals, or viruses is also associated with the induction of heat shock proteins. Hsp70 has a protective role in inflammation, infection, and regulatory roles in cytokine biosynthesis. Hsp70 exists in the cells in equilibrium between its free state, in the cytoplasm, and its bound state, protecting proteins in the nucleolus, interacting with ribosomal proteins to either refold some of the unfolded ribosomal proteins or by solubilizing the denatured ribosomal proteins to facilitate their use and increase the turnover rate. During release as a result of the heat shock, and as the nucleolus begins to recover its normal activities, a significant proportion of Hsp70 returns to the cytoplasm. This protein-protein interaction may have profound implications for viral replication.

Thus, cellular inflammatory responses to viral infection are part of the organism defense against viruses. Zinc finger proteins, therefore, may be a key to the control of the cellular inflammatory response. Agents which can modify the zinc finger heat shock proteins may be useful in controlling the stress response.

The compounds and methods of the present invention can be used to inhibit the action of the DnaJ zinc finger proteins when they are expressed in inflammation at pathologically high levels. By blocking the DnaJ zinc finger proteins, the resulting conformational change should inhibit the ATPase activity. This inhibition of the DnaJ zinc finger domain which is required for enzyme activity (FIG. 12) will reduce the inflammatory reaction in cells expressing high levels of this protein.

EXAMPLE 2

The Compounds of the Present Invention can be Used for the Simultaneous Control of Bacterial, Parasite and/or Fungal Cell Growth and the Inflammatory Responses Induced by These Biological Agents It is believed that the inflammatory response to bacteria, parasites or fungi is associated with the induction of heat shock proteins. Hence, the compounds and methods of the present invention can be used to block inappropriate and excessive cellular inflammatory response caused by induction of HSP by for example by P. acnes, the bacteria that produces acne. The chelating agents of this invention can simultaneously block the zinc finger proteins enzymes of the inflammatory response induced by the bacteria of common acne and inhibit the growth of this bacteria. Similarly, the agents of this invention can control bacterial, parasite and/or fungal growth and the associated inflammatory responses in other disease conditions.

EXAMPLE 3

Alzleimer's Disease and Inflammation

A chronic inflammatory reaction with activated microglia cells and astrocytes is a constant feature of AD. The inflammatory component is triggered by neuronal apoptosis in combination with the production of cytokines by microglia. Experimentally, the cyclooxygenase inhibitor ibuprofen decreases cytokine-induced amyloid beta production in neuronal cells. The data suggests that the simultaneous reduction of Abeta production and the associated inflammatory response by anti-inflammatory agents may be useful to prevent and treat AD. Thus, pharmacologically acceptable doses of the 2-TH acid and derivatives with the capacity to cross the blood-brain barrier can be use to treat both the Abeta aggregation and the inflammatory component of AD.

EXAMPLE 4

Nonsteroidal Anti-Inflammatory Drugs and Colorectal Cancer Chemoprevention

It has been shown that there is a 40% to 50% reduction in mortality from colorectal cancer in persons using nonsteroidal anti-inflammatory drugs (NSAIDs) on a permanent basis. NSAIDs, such as aspirin and ibuprofen, inhibit both cyclooxygenase-1 (COX-1) and cyclooxygenase-2 (COX-2) activity. COX-2 levels are increased in a number of solid tumors. Thus, COX-2 may be a molecular target for cancer prevention and/or treatment. The anti-inflammatory properties of NSAIDs are most likely due to their inhibition of cyclooxygenase enzymes. These enzymes catalyze key steps in the conversion of arachidonic acid to prostaglandins and other eicosanoids. Long term NSAIDs use results in an increase gastrointestinal bleeding, even at low doses of the drug. This side effect increases in the elderly patients that are at higher risk for colorectal cancer.

It is well established that the inflammatory cells such as fibroblasts and lymphocytes, release growth factors such as FGF, TGF alpha, interleukins, etc. These factors stimulate the growth of surrounding cancer cells. Thus, it is the contention of the inventors that inhibition of inflammatory responses, which include inactivation of metalloproteins and arrest of proliferation of cells such as fibroblasts, by using the agents presented here should be useful in the prevention and treatment of cancer.

By inhibiting the inflammatory response, the growth factors and cytokines generated by the inflammatory cells of the stroma, will not be available for stimulation of tumor growth. Thus, the agents of this invention work in at least three levels: 1) Inhibition of growth of fibroblasts and other inflammatory cells; 2) inhibition of angiogenesis and 3) inhibition of cancer cell growth.

Depending on the dose and duration of drug required, the side effects of the chemoprenventive agents of this invention will be low to achieve the desire result, because the absolute risk of colorectal cancer in the general population is low.

Combination of agents for chemoprevention of cancer may provide a much more effective approach for long term cancer prevention.

EXAMPLE 5

Transplant Rejection and Inflammatory Responses

Figure 13:
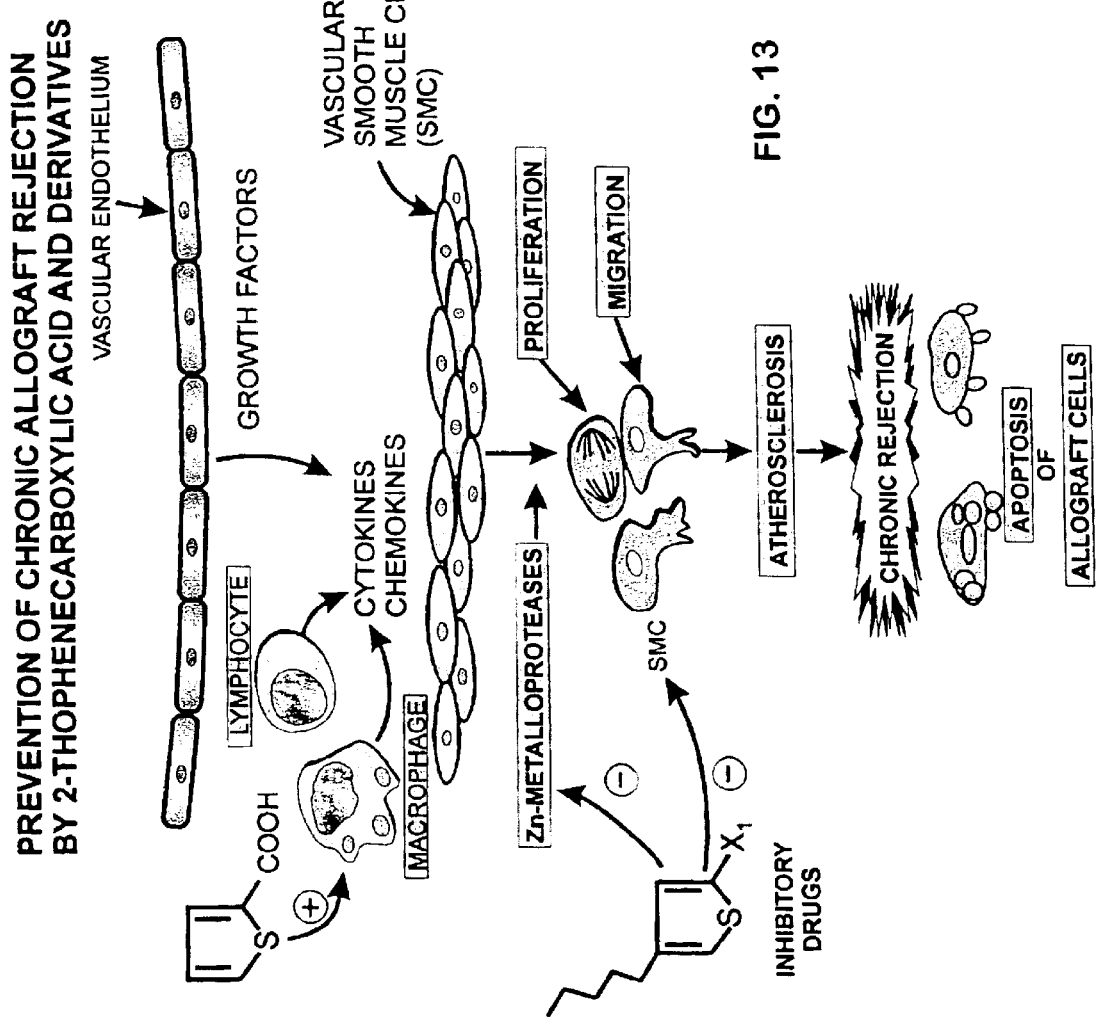
FIG. 13 is a hypothetical scheme of inhibition of chronic allograft rejection by the agents of this invention. The smooth muscle cell migration, growth, and the persistent perivascular inflammation can be prevented by the inhibitory effects of this agents on several targets such as matrix metalloproteinases, inhibition of smooth muscle cell migration, cell division, neointimal formation, inflammation and angiogenesis.

The chelating agents of the present invention can also be used to control transplant rejection in various disease conditions. It has been documented that matrix metalloproteases (MMPs) are actively involved in transplant rejection (FIG. 13). Furthermore, transplant rejection has a strong inflammatory component. The administration of the specific chelating agents of the instant invention can prevent both unwanted expression of MMPs and inflammation. The chelating agent can be administered orally or parenterally in doses described elsewhere in this application.

Organ transplant is a well-established therapy for many forms of irreversible failure of many organs. However, the success of solid-organ transplantation is a function of the continuous administration of toxic and non-specific immunosuppressive agents, which carry the risks of opportunistic infections, malignancy and many drug-specific side effects such as hypercholesterolemia and hyperglycemia In most instances, acute rejection can be overcome by specific treatments. However, the adverse effects of chronic immunosuppression, graft degradation and loss caused by chronic rejection continue to be a problem.

During organ rejection, immune responses result in persistent perivascular inflammation (FIG. 13). Cytokines, chemokines, and growth factors released by the inflammatory and repair processes stimulate the proliferation of smooth muscle cells (SMC) (FIG. 13). This results in the migration of myocytes from the media to the intima, resulting in the formation of arteriosclerotic lesions (FIG. 13). Ultimately, vascular ischemia and the subsequent development of interstitial fibrosis characterize chronic allograft rejection.

SMC proliferation activate the production and release of SMC matrix metalloproteinses in the vascular wall resulting in the digestion of surrounding extracellular vascular matrix which allows SMC cells to migrate from the media to the intima (FIG. 13).

Several therapeutic approaches have been used to control the intimal hyperplasia that occur in chronic transplant rejection. One strategy consists in the inhibition of smooth muscle cell proliferation which results in decreased ischemia, infection, and perivascular inflammation. Another strategy is to prevent smooth muscle cell migration.

Several studies have shown that smooth muscle migration can be prevented by the expression of a gene encoding an inhibitor of MMPs. The results showed that this gene therapy significantly prevented smooth muscle cell migration and neointimal formation.

The agents of this invention can be used to stop chronic organ rejection by inhibiting at least two pathological processes: 1) the proliferation of smooth muscle cells (SMC) and 2) The activation of matrix metalloproteinases in the vascular wall which allows smooth muscle cells to digest the surrounding extracellular matrix and migrate from the media to the intima (FIG. 13).

The agents of this invention could be useful for prevention of chronic rejection because these agents can arrest SMC proliferation and development of smooth muscle cell migration, neointimal formation, and subsequent interstitial fibrosis and inflammation which characterize chronic allograft rejection.

EXAMPLE 6

Zinc Induced Neuronal and Glial Cell Death and Brain Injury

In addition to the essential role of zinc as a structural or catalytic element of many proteins, in the central nervous system the abundant zinc has an additional specialized role as an intracellular signaling messenger. In this capacity, zinc is released by neural activity at numerous central excitatory synapses. Despite its general lack of toxicity, the data indicates that zinc can became a pathogenic metal that mediates neuronal death in certain neurological disease states. More specifically, following transient global ischemia, Zn2+ translocates form nerve terminals into the cell bodies of altered neurons. This translocation precedes neuronal degeneration by apoptosis, and the interruption of this transit by intracerebroventricular (icv) injection of the chelator EDTA bound to Ca2+ reduces neuronal apoptosis. Zn2+ released in excessive amounts, as is the case of glutarate, contributes to the development of cerebral infarctions following ischemia, seizures, or head trauma. Reduction of extracellular zinc accumulation and/or intracellular vulnerability to toxic zinc exposure provides a novel therapeutic approach to prevent pathological neuronal death. A major problem of the currently available zinc chelators is achieving adequate access to the CNS. Some of the agents of this invention are hydrophobic and thus are able to permeate the blood-brain barrier. Thus, pharmacologically acceptable doses of the 2-TH acid and derivatives with the capacity to cross the blood-brain barrier can be use to control Zn2+ released in excessive amounts in cerebral infarctions following ischemia, seizures, or head trauma

EXAMPLE 7

Inflammation and Inhibition of Leukotriene $A_4$ Hydrolase by 2-TH Acid and Analogues: High Specificity is Achieved by Substituting the Position 3° F. 2-TH Acid with a Hydrophobic Chain That Interacts with the Hydrophobic Pocket of the Target Enzyme The chelating agents of the present invention can also be used to inhibit specific enzymes involved in inflammation such as Leukotriene $A_4$ hydrolase ($LA_4H$)in various disease conditions (FIG. 14). This enzyme is a zinc-dependent metalloproteinase. $LTA_4$ hydrolase belongs to the M1 family of metallopeptidases. It is of practical medical interest to inhibit an enzyme that is involved in inflammatory diseases. The administration of the specific chelating agents of the instant invention can prevent unwanted inflammatory responses mediated by this enzyme. The chelating agent can be administered orally or parenterally in doses described elsewhere in this application.

Based on the zinc signature, sequence homology and aminopeptidase activity, LTA4 hydrolase has been classified as a member of the M1 family of zinc-metallopeptidases. Leukotriene (LT) $A_4$ hydrolase catalyzes the committed step in the biosynthesis of LTB4, a classical chemoattractant and immune-modulating lipid mediator involved in inflammation, host-defense against infections, and systemic, PAF-mediated lethal shock. LTA4 hydrolase is a bifunctional zinc metalloenzyme with a chloride-stimulated arginyl aminopeptidase activity. When exposed to its lipid substrate LTA4, the enzyme is inactivated and covalently modified in a process termed suicide inactivation, which puts a restrain on the enzyme's ability to form the biologically active LTB4.

In this section of this application we show that the active enzyme center can be specifically inhibited by the agents of this invention (FIG. 14). The proposed mechanism of inhibition by the agents of the invention is presented. The zinc site and catalytic residues are inhibited by 2-TH acid analogues (FIG. 14).

The leukotrienes (LT) are a group of lipid compounds with potent biological activities. They are involved in inflammatory responses and allergic disorders. These compounds are derived from the metabolism of arachidonic acid. Leukotrienes were originally isolated from leukocytes. The bone marrow cells are the main producers of LT, particularly PMN leukocytes, monocytes and tissue macrophages and mast cells. LT are very potent chemoattractans for neutrophils and recruit inflammatory cells to the site of injury. They increase leukocyte adhesion to endothelial cells of blood vessels and have potent vasoconstriction activity in smooth muscle. They also induced bronchoconstriction. LT are chemical mediators of inflammatory and allergic reactions in diseases such as rheumatoid arthritis and bronchial asthma $LTA_4$ is widely distributed in almost all mammalian cells, tissues and organs examined. In the blood, neutrophils, monocytes, lymphocytes and erythrocytes are rich sources of the enzyme. $LTA_4$ is inactivated and covalently modified by its substrate. The competitive inhibitor bestatin prevents the covalent binding of LTA4 to the enzyme, showing that it occurs at the active site.

$LTA_4$ hydrolase contains a zinc site that binds a single catalytic zinc. The similarity to other zinc-metalloenzymes is higher over a short segment of the homologous proteins, which contains a consensus sequence for a catalytic zinc site (H—E—$(X)_{1-3}$—H—$(X)_{1-120}$—E). This clearly shows that $LTA_4$ hydrolase is a zinc containing enzyme and that His-295, His-299, and Glu-318 are the zinc binding ligands. Of great interest for this invention is the fact that the enzyme can be inactivated by the zinc chelator 1,10-phenanthroline which converts the enzyme in an apoenzyme (minus Zn). Addition of stoichiometric amounts of zinc restores the enzymatic activity. Thus, the identification of LTA4 hydrolase as a member of a family of zinc metalloproteinases makes this enzyme a target for the agents of this invention.

Based on the zinc signature, sequence homology and aminopeptidase activity, LTA4 hydrolase has been classified as a member of the MI family of metallopeptidases. Thus, LTA4 hydrolase is related to numerous other zinc proteases that are present in many organism from bacteria to mammals.

It was also demonstrated that $LTA_4$ hydrolase possesses a lipid-binding pocket, which can be occupied by $LTA_4$ or by the drugs of this invention (FIG. 14). The fact that $LTA_4$ hydrolase belongs to a family of zinc proteases opened up novel possibilities of using the agents of this invention as specific enzyme inhibitors. Captopril, a zinc chelator inhibitor of the angiotensin converting enzyme also inhibits $LTA_4$ hydrolase. Captopril inhibits the enzyme at the low uM range. Captopril is extensively used as an antihypertensive agent in humans and is metabolically stable after oral administration.

Based on molecular modeling, the reaction mechanisms, and inhibitor-enzyme interactions for zinc hydrolases, we have developed selective inhibitors for this enzyme (FIG. 14). For example, the 4-pentyl-2-THA-thiosemicarbazone that has a hydrophobic tail at position 4, was found by molecular modeling to be an effective inhibitor of LTA4 hydrolase in the low uM range. This lipophilic compound can also be a potent and selective inhibitor of LTA4 hydrolase in leukocytes. The compounds of this invention were designed to inhibit LTA4 hydrolase and should be orally active.

The human $LTA_4$ hydrolase has been modeled by the inventors. The three dimensional structure revealed a protein with 3 domains which together form a deep cleft harboring the zinc catalytic site. The purpose of the following description is to cover some of the most salient molecular details of the $LTA_4$ hydrolase that are pertinent to this invention. It is not within the scope of this invention to describe the intricate relationship between the substrate and the product.

We have generated a model to identify structural and functional elements of the active site and surroundings. This in turn generated information that was used in the design of potent and specific enzyme inhibitors of this invention (FIG. 14). These compounds can induce small and large changes in the structure leading to a conformational alteration that affects the tertiary structure of the enzyme leading to its degradation by other proteases.

As can be investigated in the data banks, the zinc site in $LTA_4$ is located at the bottom of a cleft. The metal is bound to three amino acid ligands, His-295, His-299, and Glu-318. In FIG. 14 the zinc shown is bound to the 4-pentyl-2-THA-thiosemicarbazone, which creates a pentavalent covalent coordination between the drug and the active site.

The residues lining the pocket are conserved because they belong to the active center. One patch of the cavity is hydrophilic, which can make direct electrostatic interactions with the positive changes of the inhibitor of this invention, in agreement with the fact that free carboxylic acid of $LTA_4$ is required for catalysis. Furthermore, and additional hydrophobic cavity located in the vicinity of the catalytic zinc is the $LTA_4$ biding site. The zinc acts as a weak Lewis acid to activate and open the epoxide ring of $LTA_4$. In accordance to this fact, the 4-pentyl-2-THA-thiosemicarbazone inhibitor also binds to the hydrophobic cavity by the 5-pentyl side chain (FIG. 14).

The shape and curvature of the hydrophobic regions at position 4 of the agents of this invention indicate the chemical strategy for the creation of an effective inhibitor of $LTA_4$ hydrolase. The inhibitor shown in FIG. 14 is the 4-pentyl-2-THA-thiosemicarbazone (4-P-2-THA-TSC).

The modeled 4-P-2-THA-TSC inhibitor molecule adopts a bent shape that fits very well with the architecture of the binding pocket. Hence the critical double bond (hydrophobic-Hydrophylic-metal) geometry fits well with the architecture of the binding site. Considering the data obtained from modeling, the inhibitors of this inventions are highly specific. Thus, differential mapping using information available in data banks plus the characteristics of the inhibitors of this invention leads to a general formula to select potential specific inhibitors of this and other zinc metalloenzymes (FIG. 14).

HEAVY METAL POISONING

The invention relates to the treatment of heavy metal toxicity in animals and humans. More specifically, the invention relates to the use of metal chelating agents, including furoic acid, 2-TH acid and their derivatives, analogues and related chemicals falling within the definition of the formulas shown in FIGS. 1 and 2 as pharmacological agents to prevent and/or treat toxicity caused by heavy metals. The prevention and treatment of diseases and toxicities caused by metals such as uranium, lead, iron, copper, nickel, and tungsten can be accomplished by the chelating agents of this invention. The chelating agent can be administered orally or parenterally in doses described elsewhere in this application.

The chelating agent is administered to the patient by systemic administration at the proper dosage by injection, transdermal, rectal, inhalation, intranasally or other pharmacologically acceptable form. The chelating agent displaces the toxic metal from the protein, binds the toxic metal, which results in an inactive chelate and subsequently is eliminated from the body.

The environmental metals most deleterious for human health are lead, mercury, arsenic and cadmium. The daily exposure to lead is a major pediatric concern. All these metals are carcinogenic.

Heavy metals exert their toxic effects by binding with one or more ligands essential for normal physiologic functions. Heavy-metal antagonists, denoted chelating agents, are created specifically to compete with these ligands for the metals. In this form, they prevent and reverse toxic effects and enhance the excretion of the metals.

The chelating agents of this invention have the following properties: high solubility in water, stable, penetrate to the sites of metal storage, capacity to form non-toxic complexes with the toxic metals, ability to retain toxic metals at low pH and able to excrete the chelate. Furthermore, they have low affinity for $Ca^{2+}$.

The following examples illustrate the use of the chelating agents of this invention to prevent or treat heavy metal poisoning.

EXAMPLE 1

Prevention of Formation of Abnormal Iron-finger Proteins

By molecular modeling, the inventors have determined that it is feasible to maintain zinc finger metalloproteins in an undamaged zinc-containing configuration by using a combination of specific agents of this invention and radical scavengers. This combination counteracts the formation of both aberrant iron-finger proteins and free radicals. Thus, 2-Th acid and pharmacologically acceptable derivatives thereof, in acceptable doses delineated above, can be used to prevent the formation of aberrant iron-finger proteins involved in carcinogenesis and aging. Free radical scavengers include anti-oxidants such as vitamin E, Flavonoids, etc.

EXAMPLE 2

Treatment of Iron and Copper Toxicity

Acute effects of iron toxicity include hepatic necrosis, coma and death Deleterious chronic effects of iron toxicity usually result from iron supplementation particularly in the elderly population. Desferoxamine is the iron chelating agent of choice to treat iron toxicity or iron overload. However, this agent is administered parenterally and has a number of side effects such as hypotension, rash, and analphylatic shock.

The novel agents of the present invention can be used to chelate and remove the excess iron. The dosage range for this use is 250 mg to 6000 mg per day administered intravenously or orally.

In addition to its use as a chelating agent for the treatment of copper, mercury, iron and lead poisoning, the agents of this invention can be used in the treatment of Wilson's disease.

Wilson's disease is a rare hepatolenticular degeneration due to and excess copper in the blood and tissues. Penicillamine is the agent of choice to treat Wilson's disease. However, penicillamine has a number of adverse reactions including gastrointestinal bleeding due to gastritis, and hematological abnormalities.

The novel agents of the present invention can be use to chelate and remove the excess copper. The dosage range for this use is 250 mg to 6000 mg per day administered intravenously or orally.

EXAMPLE 3

Prevention and Treatment of Lead, Cadmium and Mercury Poisoning

Lead is a ubiquitous metal in the environment as a result of its natural occurrence and its industrial use. The primary sources of lead are leaded paint and lead in the drinking water. The major routes of absorption of lead are from the gastrointestinal track and the respiratory system. Once lead is absorbed it essentially accumulates in all organs containing metalloproteins. At present, lead poisoning is treated with combination therapy including dimercaprol, EDTA, penicillamine and succimer.

One of the mechanisms for toxicity of lead is the inhibition of a zinc metalloenzyme, gamma-aminolevulinate dehydratase (ALAD), which is also inhibited by aluminum. In the case of lead, the inhibition occurs through the substitution of lead for zinc. Thus, the agents of this invention can be use to remove lead from this and other metalloproteins.

Lead poisoning can be prevented or treated by the use of the novel chelating agents of the present invention. For prevention, the individual who will be exposed to an environment containing lead in the form of toxic fumes, water, or lead paints can be prophylactically treated with the chelating agents of this invention which will chelate and remove from the body the lead prior to the distribution to the tissues. The individual already intoxicated by lead is treated with the novel chelating agents to remove the lead from the tissues and eliminate the chelate-lead by the kidneys, subsequently reversing the progression of the disease. For either indication the broad dose range of 250 mg to less than 6000 mg a day administered intravenously or orally is suggested. Similarly, the same agents and doses can be used in the treatment of Cadmium and Mercury exposure.

EXAMPLE 4

Prevention and Treatment of Exposure to Stable or Radioactive Heavy Metals: Uranium, Tungsten and Nickel The use of heavy metals such as depleted uranium (DID) and tungsten alloys in military applications worldwide could result in poisoning from occupational exposure and environmental pollution.

The use of uranium depleted weapons can result in soldiers with embedded heavy metal shrapnel or poisoning by aspiration of uranium containing gases created in the battlefield.

Furthermore, it has been shown that soluble or insoluble depleted uranium particles can transformed normal cells to the malignant phenotype. These data indicates an increase risk of carcinogenesis in exposed individuals.

The data demonstrates that DU and tungsten are transforming, genotoxic, and ribotoxic agents in vitro. The in vivo effects of internalized DU include enhancement of mutagenicity, oncogene activation and tumor suppressor gene neutralization. Similarly, tungsten alloys and nickel were also shown to be neoplastic transforming agents. Tungsten and nickel have been shown to cause genotoxicity, ribotoxicity, and genomic instability.

The inventors have determined by molecular modeling that the deleterious effects of exposure to heavy metals, including depleted uranium, tungsten and nickel can be antagonized by the administration of 2-TH acid or derivatives. The chelated heavy metal complex is inactivated and excreted by the kidneys. The compounds of this invention have excellent tissue penetrability, including penetration into the cerebrospinal fluid and brain tissues. The inventors' have concluded that a pharmacologically appropriate dose of the 2-TH acid or derivative thereof, can be effectively used to treat heavy metal toxicity and prevent carcinogenesis in exposed individuals. When prophilactically used the novel agents should be able to prevent heavy metal damage to the cells.

The novel agents of the present invention can be use to chelate and remove the excess soluble UD, tungsten and nickel. The dosage range for this use is 250 mg to 6000 mg per day administered intravenously or orally.

A kit containing 500 mg capsules of 2-TH acid or derivatives thereof can be carried out by soldiers or other personnel in the field when contamination by stable or radioactive heavy metals is a risk. The soldiers can begin ingestion of the appropriate dose of the chelator upon exposure to the radioactive heavy metals such as depleted uranium.

ILLUSTRATIVE PREPARATIONS CONTAINING METAL CHELATING 2-THIOPHENECARBOXYLIC ACID AND DERIVATIVES FOR THE TREATMENT AND PREVENTION OF SPECIFIC DISEASE STATES

EXAMPLE 1

Topical or Intravaginal Preparation of 2-TH Acid in an Absorption Base

A topical or intravaginal preparation of furoic acid or 2-TH acid in an absorption base is made by incorporating 0.001% to 99.9%, preferably 1% to 50%, most preferably 5% to 20% 2-TH acid into an absorption base. One preferred embodiment of the topical preparation is made by dissolving 10% 2-TH acid in deionized water and then incorporating the solution into an equal amount of Aquaphor on a wt/wt basis. Further, the 2-TH acid or derivatives can be incorporated into a stick for application to the lips to treat herpes infections. It will be appreciated that 2-TH acid derivatives can be used in place of the 2-TH acid in the topical preparation. It will be also appreciated that such preparations can be used to treat topical conditions such as virus infections, fungal infections, susceptible bacterial infections, radiation damage, including ultraviolet, medical or atomic radiation, skin cancers or any other condition mediated by the above described mechanisms.

EXAMPLE 2

Furoic Acid and 2-TH Acid Solutions

Furoic acid or 2-TH acid can be employed topically, for vaginal installation, for inhalation or as a mouthwash as a 0.001% to 99.9%, preferably 1% to 50%, most preferably 5% to 20% aqueous solution. The preparation can be used in any pharmaceutically acceptable manner including topically, orally, on the mucosa and so forth. It will be noted that furoic acid or 2-TH acid derivatives can be used in place of the 2-TH acid, if desired. For inhalation purposes, the solution may be atomized with the use of an appropriate device.

As stated above, it is likely that furoic acid or 2-TH acid will interfere with the replication of the retroviruses by chelating zinc and iron and preventing the activity of certain zinc and iron containing proteins. Therefore, a suitable preparation of a chelating material, for example, 2-TH acid or derivative may be used for vaginal application to prevent infection with any virus containing zinc finger proteins as an essential component of the viral replicating machinery. Such viruses include, but are not limited to the families described elsewhere in this application and shown in Table 2. As explained above, the 2-TH acid and substituted derivatives thereof are used to attack proteins having zinc finger segments, which are essential for packaging RNA in the viral particles.

The preparation may be produced by incorporating approximately 5% to 20% 2-TH acid in a suitable base and instilling the ointment vaginally before coitus. Such preparations may be used prophylactically to prevent infection with these viruses.

Furthermore, the preparations may be used vaginally to treat the uterine cervix infected with papilloma virus.

EXAMPLE 3

Ocular Preparation

A preparation of 2-TH acid or a derivative thereof can be prepared for the treatment of ocular herpes or other viral infections of the eyes. The topical or intraocular ophthamological preparation includes approximately 0.01% to approximately 5% 2-TH acid or one of its substituted derivatives in an appropriate, ion-free vehicle, such as methylcellulose.

EXAMPLE 4

Acne Formulation

A preparation useful in the treatment and control of acne comprises approximately 5% to 20% of furoic acid or 2-TH acid, by weight, in a suitable topical lotion. The acne preparation can include approximately 1% to approximately 99% of furoic acid or 2-TH acid, derivative or analog thereof A preferred range is approximately 5% to approximately 20%. The lotion is applied to the skin two or three times daily.

EXAMPLE 5

Intranasal and Inhalation Formulations

A product suitable for intranasal administration for treatment of upper respiratory diseases includes approximately 10 mM furoic acid or 5 mM 2-TH acid in a suitable isotonic vehicle. The intranasal solution can be used in a range between 0.01 mM to 10 mM, preferably 0.1 mM up to 20 mM furoic acid or 2-TH acid or greater.

Likewise, a solution for pulmonary inhalation is prepared by adding furoic acid or 2-TH acid to normal saline for nebulization, the resulting solution being in a range of 0.001% to 50% furoic acid or 2-TH acid, derivative or analog in saline or sterile distilled water for nebulization.

EXAMPLE 6

Systemic Administration

A systemic preparation of 2-TH acid, its derivatives or analogs containing approximately 1% to 100% active ingredient may be administered orally, intravenously or by any acceptable route for the treatment of cancer, systemic infections, inflammation or neurodegenerative diseases. For example, 2-TH acid prepared in 00 gelatin capsules at 500 mg per capsule may be used to effectively control metastatic cancer and the associated inflammation. Likewise, an injectable form may be prepared.

As set out above, the safe and effective daily systemic dose may range for 250 mg to 10 grams for a 70 Kg subject, with the preferred range being 250 mg to 5 grams, and the most preferred dose being 250 mg to 1000 mg.

We claim:

1. A method of treating diseases caused by viruses, pathogenic prokaryotic and pathogenic eukaryotic cells, comprising the systemic administration of an effective amount of a compound having the formula

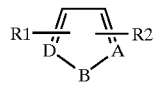

wherein any one of A, B and D is N, one is O and the other is S; wherein RI, which can be singly or multiply substituted in any position of the thiophene ring not already subsituted by R2, is selected from the group consisting of hydrogen, alkyl and substituted alkyl wherein the alkyl portion is from 1 to 21 carbon atoms, inclusive, and isomeric forms thereof, cycloalkyls and substituted cycloalkyl, substituted oxygen, substituted nitrogen, halogen, phenyl, and substituted phenyl, —(CH2)n—OH, —(CH2)n—NR3R4, and isomeric forms thereof: wherein n is an integer of from 1 to 21, inclusive, R3 and R4 are H or alkyl of from 1 to 21 carbon atoms, inclusive, and isomeric forms thereof; wherein R2, which can be singly or multiply substituted in any position of the thiophene ring not already substituted by where R1, is

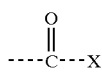

and X is the amino function of a compound selected from the group consisting of 2-hydrazine, 2-hydrazone, or 2-thiosemicarbazone; and the pharmaceutically acceptable acid-addition salts thereof, to a mammal hosting a pathogenic virus, prokaryotic pathogellic organism, or eukaryotic pathogenic cell.

2. A compound having the formula:

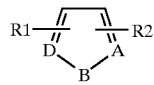

wherein any one of A, B and D is N, one is O and the other is S; R1 and R2 are as defined below, and can be attached to any ring carbon or nitrogen atom, the R1 can be multiply attached to any ring carbon atom; the R1 can be 2-carboxylic, 2-hydrazine, 2-hydrazone, and 2-thiosemicarbazone; wherein RI, which can be singly or multiply substituted in any position of the thiophene ring not already substituted by R2, is selected from the group consisting of hydrogen, alkyl and substituted alkyl wherein the alkyl portion is from 1 to 21 carbon atoms, inclusive, and isomeric forms thereof, cycloalkyls and substituted cycloalkyl, substituted oxygen, substituted nitrogen, halogen, phenyl, and substituted phenyl, —(CH2)n—OH, —(CH2)n—NR3R4. and isomeric forms thereof: wherein n is an integer of from 1 to 21, inclusive, R3 and R4 are H or alkyl of from 1 to 21 carbon atoms, inclusive, and isomeric forms thereof; wherein R2, which can be singly or multiply substituted in any position of the thiophene ring not already substituted by where R1, is

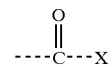

and X is the amino function of a compound selected from the group consisting of 2-hydrazine, 2-hydrazone, or 2-thiosemicarbazone; and the pharmaceutically acceptable acid-addition salts thereof.

3. A compound according to claim 2, wherein said compounds are selected from the group consisting of compounds in which the hydrogen in positions 3 or 4 have been replaced by a fatty acid side chain of 2 to 21 carbons or an amino acid side chain of 2 to 21 amino acids.

4. A compound according to claim 2, wherein the compound is selected from the group consisting of carboxylic acids, hydrazines, or hydrazones having the formulas —COOH, —CONNH2, or —C=NH—NH—C=O—, respectively where —C is attached to position 2.

5. A compound according to claim 2, wherein the compound is selected from the group consisting of thiosemicarbazones having the formula —C=NH—NH—C=S—, where —C is attached to position 2.

6. A compound according to claim 2, wherein the compound is 4-butyl-3-5-dichloro-2-thiophenecarboxylic acid, 4-butyl-3-5-dichloro-2-thiophenecarboxylic acid hydrazine, or 4-butyl-3-5-dichloro-2-thiophenecarboxylic acid hydrazone or 4-butyl-3-5-dichloro-2-thiophenecarboxylic acid thiosemicarbazone.

7. A compound according to claim 2, wherein R1 is in the 4-position and is a fatty acid of from 1 to 21 carbon atoms, inclusive, and isomeric forms thereof; wherein R2 is in the 3 or 5 position and is an halogen.

8. A compound according to claim 2, wherein R1 is in the 4-position and is a peptide of from 1 to 21 amino acids, inclusive, and isomeric forms thereof; wherein R2 is in the 3 or 5 position and is an halogen.

9. A composition comprising at least two compounds from the following compound groups having the formula:

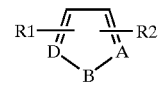

wherein any one of A, B and D is N, one is O and the other is S; R1 and R2 are as defined in claim 2, and can be attached to any ring carbon or nitrogen atom, the R1 can be multiply attached to any ring carbon atom; the R1 can be 2-carboxylic, 2-hydrazine, 2-hydrazone, and 2-thiosemicarbazone.

* * * * *